(12) United States Patent
Reddy et al.

(10) Patent No.: US 7,744,889 B2
(45) Date of Patent: Jun. 29, 2010

(54) ALPHA, BETA-UNSATURATED SULFOXIDES FOR TREATING PROLIFERATIVE DISORDERS

(75) Inventors: E. Premkumar Reddy, Villanova, PA (US); M. V. Ramana Reddy, Upper Darby, PA (US); Stanley C. Bell, Narberth, PA (US)

(73) Assignee: Temple University - Of The Commonwealth System of Higher Education, Philadelphia, PA (US)

( * ) Notice: Subject to any disclaimer, the term of this patent is extended or adjusted under 35 U.S.C. 154(b) by 64 days.

(21) Appl. No.: 10/574,993

(22) PCT Filed: Nov. 8, 2004

(86) PCT No.: PCT/US2004/037293

§ 371 (c)(1),
(2), (4) Date: Apr. 6, 2006

(87) PCT Pub. No.: WO2005/046599

PCT Pub. Date: May 26, 2005

(65) Prior Publication Data

US 2006/0280746 A1 Dec. 14, 2006

Related U.S. Application Data

(60) Provisional application No. 60/520,523, filed on Nov. 14, 2003.

(51) Int. Cl.
*A61K 39/395* (2006.01)
(52) U.S. Cl. .............. 424/155.1; 514/355; 514/461; 514/679; 546/315; 568/63
(58) Field of Classification Search .......... 514/355, 514/461, 679; 546/315; 568/63; 424/115.1
See application file for complete search history.

(56) References Cited

U.S. PATENT DOCUMENTS

| | | | | |
|---|---|---|---|---|
| 3,865,867 | A | 2/1975 | Olin et al. | 260/472 |
| 3,975,435 | A | 8/1976 | Nikawitz | 260/558 |
| 6,117,364 | A | 9/2000 | Vorderbruggen et al. | 252/395 |
| 6,147,250 | A | 11/2000 | Somers | |
| 6,201,154 | B1* | 3/2001 | Reddy et al. | 568/28 |
| 6,359,013 | B1* | 3/2002 | Reddy et al. | 514/710 |
| 6,414,034 | B1* | 7/2002 | Reddy et al. | 514/710 |
| 6,486,210 | B2* | 11/2002 | Reddy et al. | 514/708 |
| 6,541,475 | B2* | 4/2003 | Reddy et al. | 514/252.12 |
| 6,548,553 | B2* | 4/2003 | Reddy et al. | 514/710 |
| 6,576,675 | B1* | 6/2003 | Reddy et al. | 514/710 |
| 6,599,932 | B1* | 7/2003 | Reddy et al. | 514/438 |
| 6,642,410 | B2 | 11/2003 | Reddy et al. | 562/426 |
| 6,646,009 | B2 | 11/2003 | Reddy et al. | 514/604 |
| 6,656,968 | B1 | 12/2003 | Reddy et al. | 514/508 |
| 6,656,973 | B2* | 12/2003 | Cosenza et al. | 514/710 |
| 6,667,346 | B2 | 12/2003 | Reddy et al. | 514/710 |
| 6,762,207 | B1* | 7/2004 | Reddy et al. | 514/709 |
| 6,767,926 | B1 | 7/2004 | Cosenza et al. | 514/710 |
| 6,787,667 | B2 | 9/2004 | Reddy et al. | 562/429 |
| 6,833,480 | B2 | 12/2004 | Reddy et al. | 568/28 |
| 7,053,123 | B2 | 5/2006 | Reddy et al. | 514/710 |
| 7,056,953 | B2 | 6/2006 | Reddy et al. | 514/710 |
| 7,595,347 | B2 | 9/2009 | Cosenza et al. | 514/710 |
| 7,598,232 | B2* | 10/2009 | Reddy et al. | 514/114 |
| 2002/0028818 | A1 | 3/2002 | Reddy et al. | 514/252.12 |
| 2002/0115643 | A1 | 8/2002 | Reddy et al. | 514/127 |
| 2003/0114538 | A1 | 6/2003 | Reddy et al. | 514/709 |
| 2004/0214903 | A1 | 10/2004 | Cosenza et al. | 514/710 |
| 2008/0161252 | A1 | 7/2008 | Reddy et al. | 514/34 |

FOREIGN PATENT DOCUMENTS

WO WO 02/28828 A1 4/2002
WO 2005/089269 A2 9/2005

OTHER PUBLICATIONS

Zhong, et al., {Simple and stereoselective synthetic route to (E)-1-alkenyl sulfoxides via terminal alkynes, Journal of Chemical Research, Synopses (2000), (12), 588-589}.*
Schwan et al., {1-Alkenesulfinyl Chlorides: Synthesis, Characterization, and Some Substitution Reactions, Journal of Organic Chemistry (1998), 63(22), 7825-7832}.*
Schwan et al., {Oxidative fragmentations of selected 1-alkenyl sulfoxides. Chemical and spectroscopic evidence for 1-alkenesulfinyl chlorides, Tetrahedron Letters (1996), 37(14), 2345-8}.*
Tanaka et al., {Intermolecular transfer of the 2,4,6-trinitrophenyl group bound to amino radicals, Nippon Kagaku Zasshi (1962), (83), 895-901}.*
Schwan et al., 1-Alkenesulfinyl Chlorides: Synthesis, Characterization, and Some Substitution Reactions, Journal of Organic Chemistry (1998), 63(22), 7825-7832.*
*Chem. Abs.* 135:122252, abstracting P. Zhong et al., "Simple and stereoselective synthetic route to (E)-1-alkenyl sulfoxides via terminal alkynes", *J. Chem. Res., Synop.*, 2000, (12), 588-89.
*Chem. Abs.* 133:192741, abstracting A. Schwan et al., "The reaction of thiirane S-oxides with methyllithium lithium bromide complex. A surprising preference for deprotonation over desulfurization", *Sulfur Lett.*, 2000, 23(3), 111-19.
T. Kageyama et al., "Sodium bromite: a new selective reagent for the oxidation of sulfides and alcohols", *Synthesis*, 1983, (10), 815-16.
U.S. Appl. No. 12/460,182, filed Jul. 14, 2009, Reddy et al.

* cited by examiner

*Primary Examiner*—Jafar Parsa
*Assistant Examiner*—Chukwuma O Nwaonicha
(74) *Attorney, Agent, or Firm*—Drinker Biddle & Reath LLP

(57) ABSTRACT

αβ-Unsaturated sulfoxides of Formula I:

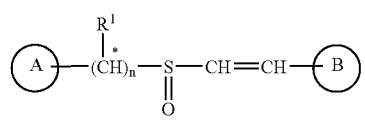

are useful as antiproliferative agents including, for example, anticancer agents, and as radioprotective and chemoprotective agents.

40 Claims, No Drawings

ALPHA, BETA-UNSATURATED SULFOXIDES FOR TREATING PROLIFERATIVE DISORDERS

CROSS-REFERENCE TO RELATED APPLICATION

This application claims the benefit of U.S. Provisional Application Ser. No. 60/520,523, filed Nov. 14, 2003, the entire disclosure of which is incorporated herein by reference.

FIELD OF THE INVENTION

The invention relates to compositions and methods for the treatment of proliferative disorders, including but not limited to cancer. The invention further relates to compositions that afford protection from the cytotoxic effects of ionizing radiation and of cytotoxic chemotherapeutic agents.

BACKGROUND OF THE INVENTION

Ionizing Radiation Health Risks

Ionizing radiation has an adverse effect on cells and tissues, primarily through cytotoxic effects. In humans, exposure to ionizing radiation occurs primarily through therapeutic techniques (such as anticancer radiotherapy) or through occupational and environmental exposure.

Therapeutic Administration of Radiation

A major source of exposure to ionizing radiation is the administration of therapeutic radiation in the treatment of cancer or other proliferative disorders. Depending on the course of treatment prescribed by the treating physician, multiple doses may be received by an individual over the course of several weeks to several months.

Therapeutic radiation is generally applied to a defined area of the individual's body which contains abnormal proliferative tissue, in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment.

There are also some treatments that require exposure of the individual's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Numerous methods have been designed to reduce normal tissue damage while still delivering effective therapeutic doses of ionizing radiation. These techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

For example, one treatment for individuals with metastatic tumors involves harvesting their hematopoietic stem cells and then treating the individual with high doses of ionizing radiation. This treatment is designed to destroy the individual's tumor cells, but has the side effect of also destroying their normal hematopoietic cells. Thus, a portion of the individual's bone marrow (containing the hematopoietic stem cells), is removed prior to radiation therapy. Once the individual has been treated, the autologous hematopoietic stem cells are returned to their body.

However, if tumor cells have metastasized away from the tumor's primary site, there is a high probability that some tumor cells will contaminate the harvested hematopoietic cell population. The harvested hematopoietic cell population may also contain neoplastic cells if the individual suffers from cancers of the bone marrow such as the various French-American-British (FAB) subtypes of acute myelogenous leukemias (AML), chronic myeloid leukemia (CML), or acute lymphocytic leukemia (ALL). Thus, the metastasized tumor cells or resident neoplastic cells must be removed or killed prior to reintroducing the stem cells to the individual. If any living tumorigenic or neoplastic cells are re-introduced into the individual, they can lead to a relapse.

Prior art methods of removing tumorigenic or neoplastic cells from harvested bone marrow are based on a whole-population tumor cell separation or killing strategy, which typically does not kill or remove all of the contaminating malignant cells. Such methods include leukopheresis of mobilized peripheral blood cells, immunoaffinity-based selection or killing of tumor cells, or the use of cytotoxic or photosensitizing agents to selectively kill tumor cells. In the best case, the malignant cell burden may still be at 1 to 10 tumor cells for every 100,000 cells present in the initial harvest (Lazarus et al. *J. of Hematotherapy*, 2(4):457-66, 1993).

Thus, there is needed a purging method designed to selectively destroy the malignant cells present in the bone marrow, while preserving the normal hematopoietic stem cells needed for hematopoietic reconstitution in the transplantation subject.

Occupational/Environmental Radiation Exposure

Exposure to ionizing radiation can also occur in the occupational setting. Occupational doses of ionizing radiation may be received by persons whose job involves exposure (or potential exposure) to radiation, for example in the nuclear power and nuclear weapons industries. Military personnel stationed on vessels powered by nuclear reactors, or soldiers required to operate in areas contaminated by radioactive fallout, risk similar exposure to ionizing radiation. Occupational exposure may also occur in rescue and emergency personnel called in to deal with catastrophic events involving a nuclear reactor or radioactive material. Other sources of occupational exposure may be from machine parts, plastics, and solvents left over from the manufacture of radioactive medical products, smoke alarms, emergency signs, and other consumer goods. Occupational exposure may also occur in persons who serve on nuclear powered vessels, particularly those who tend the nuclear reactors, in military personnel operating in areas contaminated by nuclear weapons fallout, and in emergency personnel who deal with nuclear accidents. Environmental exposure to ionizing radiation may also result from nuclear weapons detonations (either experimental or during wartime), discharges of actinides from nuclear waste storage and processing and reprocessing of nuclear fuel, and from naturally occurring radioactive materials such as radon gas or uranium. There is also increasing concern that the use of ordnance containing depleted uranium results in low-level radioactive contamination of combat areas.

Radiation exposure from any source can be classified as acute (a single large exposure) or chronic (a series of small low-level, or continuous low-level exposures spread over time). Radiation sickness generally results from an acute exposure of a sufficient dose, and presents with a characteristic set of symptoms that appear in an orderly fashion, including hair loss, weakness, vomiting, diarrhea, skin burns and bleeding from the gastrointestinal tract and mucous membranes. Genetic defects, sterility and cancers (particularly bone marrow cancer) often develop over time. Chronic exposure is usually associated with delayed medical problems such as cancer and premature aging. An acute a total body exposure of 125,000 millirem may cause radiation sickness. Localized doses such as are used in radiotherapy may not cause radiation sickness, but may result in the damage or death of exposed normal cells.

For example, an acute total body radiation dose of 100,000-125,000 millirem (equivalent to 1 Gy) received in less than one week would result in observable physiologic effects such as skin burns or rashes, mucosal and GI bleeding, nausea, diarrhea and/or excessive fatigue. Longer term cytotoxic and genetic effects such as hematopoietic and immunocompetent cell destruction, hair loss (alopecia), gastrointestinal, and oral mucosal sloughing, venoocclusive disease of the liver and chronic vascular hyperplasia of cerebral vessels, cataracts, pneumonites, skin changes, and an increased incidence of cancer may also manifest over time. Acute doses of less than 10,000 millirem (equivalent to 0.1 Gy) typically will not result in immediately observable biologic or physiologic effects, although long term cytotoxic or genetic effects may occur.

A sufficiently large acute dose of ionizing radiation, for example 500,000 to over 1 million millirem (equivalent to 5-10 Gy), may kill an individual immediately. Doses in the hundreds of thousands of millirems may kill within 7 to 21 days from a condition called "acute radiation poisoning." Reportedly, some of the Chernobyl firefighters died of acute radiation poisoning, having received acute doses in the range of 200,000-600,000 millirem (equivalent to 2-6 Gy). Acute doses below approximately 200,000 millirem do not result in death, but the exposed individual will likely suffer long-term cytotoxic or genetic effects as discussed above.

Acute occupational exposures usually occur in nuclear power plant workers exposed to accidental releases of radiation, or in fire and rescue personnel who respond to catastrophic events involving nuclear reactors or other sources of radioactive material. Suggested limits for acute occupational exposures in emergency situations were developed by the Brookhaven National Laboratories, and are given in Table 1.

TABLE 1

| Whole Body Conditions for Dose Limit | Activity Required | Conditions for Exposure |
|---|---|---|
| 10,000 millirem* | Protect property | Voluntary, when lower dose not practical |
| 25,000 millirem | Lifesaving Operation; Protect General Public | Voluntary, when lower dose not practical |
| >25,000 millirem | Lifesaving operation; Protect large population | Voluntary, when lower dose not practical, and the risk has been clearly explained |

*100,000 millirem equals one sievert (Sv). For penetrating radiation such as gamma radiation, one Sv equals approximately one Gray (Gy). Thus, the dosage in Gy can be estimated as 1 Gy for every 100,000 millirem.

A chronic dose is a low level (i.e., 100-5000 millirem) incremental or continuous radiation dose received over time. Examples of chronic doses include a whole body dose of ~5000 millirem per year, which is the dose typically received by an adult working at a nuclear power plant. By contrast, the Atomic Energy Commission recommends that members of the general public should not receive more than 100 millirem per year. Chronic doses may cause long-term cytotoxic and genetic effects, for example manifesting as an increased risk of a radiation-induced cancer developing later in life. Recommended limits for chronic exposure to ionizing radiation are given in Table 2.

TABLE 2

| Organ or Subject | Annual Occupational Dose in millirem |
|---|---|
| Whole Body | 5000 |
| Lens of the Eye | 15,000 |
| Hands and wrists | 50,000 |
| Any individual organ | 50,000 |
| Pregnant worker | 500/9 months |
| Minor (16-18) receiving training | 100 |

By way of comparison, Table 3 sets forth the radiation doses from common sources.

TABLE 3

| Sources | Dose In Millirem |
|---|---|
| Television | <1/yr |
| Gamma Rays, Jet Cross Country | 1 |
| Mountain Vacation - 2 week | 3 |
| Atomic Test Fallout | 5 |
| U.S. Water, Food & Air (Average) | 30/yr |
| Wood | 50/yr |
| Concrete | 50/yr |
| Brick | 75/yr |
| Chest X-Ray | 100 |
| Cosmic Radiation (Sea Level) | 40/yr (add 1 millirem/100 ft elev.) |
| Natural Background San Francisco | 120/yr |
| Natural Background Denver | 50/yr |
| Atomic Energy Commission Limit For Workers | 5000/yr |
| Complete Dental X-Ray | 5000 |
| Natural Background at Pocos de Caldras, Brazil | 7000/yr |
| Whole Body Diagnostic X-Ray | 100,000 |
| Cancer Therapy | 500,000 (localized) |
| Radiation Sickness-Nagasaki | 125,000 (single doses) |
| $LD_{50}$ Nagasaki & Hiroshima | 400,000-500,000 (single dose) |

Chronic doses of greater than 5000 millirem per year (0.05 Gy per year) may result in long-term cytotoxic or genetic effects similar to those described for persons receiving acute doses. Some adverse cytotoxic or genetic effects may also occur at chronic doses of significantly less than 5000 millirem per year. For radiation protection purposes, it is assumed that any dose above zero can increase the risk of radiation-induced cancer (i.e., that there is no threshold). Epidemiologic studies have found that the estimated lifetime risk of dying from cancer is greater by about 0.04% per rem of radiation dose to the whole body.

While anti-radiation suits or other protective gear may be effective at reducing radiation exposure, such gear is expensive, unwieldy, and generally not available to public. Moreover, radioprotective gear will not protect normal tissue adjacent a tumor from stray radiation exposure during radiotherapy. What is needed, therefore, is a practical way to protect individuals who are scheduled to incur, or are at risk for incurring, exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., *Semin. Radial. Oncol.* 6:306-320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Maisin, J. R., Bacq and Alexander Award Lecture. "Chemical radioprotection: past, present, and future prospects", *Int J. Radial Biol.* 73:443-50, 1998). Pharmaceutical radiation sensitizers, which are known to preferentially enhance the effects of radiation in cancerous tissues, are clearly unsuited for the general systemic protection of normal tissues from exposure to ionizing radiation.

What are needed are therapeutic agents to protect individuals who have incurred, or are at risk for incurring exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Protection from Toxic Side Effects of Experimental Chemotherapy

Experimental chemotherapy has been the mainstay of treatment offered to patients diagnosed with surgically unresectable advanced cancers, or cancers refractory to standard chemotherapy and radiation therapy. Of the more effective classes of drugs, curative properties are still limited. This is because of their relatively narrow therapeutic index, restricted dosage, delayed treatments and a relatively large proportion of only partial tumor reductions. This state is usually followed by recurrence, increased tumor burden, and drug resistant tumors.

Several cytoprotective agents have been proposed to enhance the therapeutic index of anticancer drugs. For methotrexate toxicity, such agents include asparaginase, leucovorum factor, thymidine, and carbipeptidase. Because of the extensive use of anthracyclines, specific and non-specific cytoprotective agents have been proposed which have varying degrees of efficacy; included are corticosteroids, desrazoxane and staurosporin. The latter is of interest in that it includes a G1/S restriction blockade in normal cells. (Chen et al., *Proc AACR* 39:4436A, 1998).

Cisplatin is widely used and has a small therapeutic index which has spurred investigation and search of cytoprotectants. Among the cytoprotectants for cisplatin with clinical potential are mesna, glutathione, sodium thiosulfate, and amifostine (Griggs, *Leuk. Res.* 22 Suppl 1:S27-33, 1998; List et al., *Semin. Oncol.* 23(4 Suppl 8):58-63, 1996; Taylor et. al., *Eur. J. Cancer* 33(10):1693-8, 1997). None of these or other proposed cytoprotectants such as oxonic acid for fluoropyrimidine toxicity, or prosaptide for paclitaxel PC12 cell toxicity, appears to function by a mechanism which renders normal replicating cells into a quiescent state.

What are needed are new effective cytoprotective agents which are effective in protecting animals, inclusive of humans, from the cytotoxic side effects of chemotherapeutic agents.

$\alpha,\beta$-Unsaturated Sulfone Compounds

Certain $\alpha,\beta$-unsaturated sulfones, particularly styrylbenzyl sulfones have been shown to possess antiproliferative, radioprotective and chemoprotective activity. See, U.S. Pat. Nos. 6,599,932, 6,576,675, 6,548,553, 6,541,475, 6,486,210, 6,414,034, 6,359,013, 6,201,154, 6,656,973 and 6,762,207, the entire disclosures of which are incorporated herein.

Metabolic Sulfoxide Oxidation

Sulfoxide functional groups are metabolically oxidized to the corresponding sulfones via the cytochrome P-450 family of oxidizing enzymes. Cytochrome P-450 enzymes are iron-based proteins that mediate redox reactions wherein a substrate, e.g., a drug molecule, is oxidized and the iron is reduced.

The oxidative metabolism of sulfoxide moieties has been employed by administering sulfoxide compounds that are metabolically converted to active metabolite sulfone compounds. One example of this strategy is the administration of sulindac sulfoxide, a commonly prescribed antiinflammatory drug that has been shown to additionally have cancer chemopreventative activity. See, Thompson et al., *Cancer Research*, 1997, Jan. 15; 57(2), pg. 267-271.

The sulindac sulfoxide possesses no antiinflammatory activity but is rather a prodrug that is converted metabolically to the active sulfide. Once administered, the sulindac sulfoxide is readily reduced to the antiinflammatory sulfide form in the liver and in the colon via bacterial microflora. However, the sulindac sulfoxide is also metabolically oxidized in the liver to the sulfone that is subsequently excreted in the bile and intestine. The sulfone metabolite has no antiinflammatory activity, however the sulfone still retains the ability to inhibit tumor cell growth and induce apoptosis. See S. M. Fischer, *Frontiers in Bioscience*, 2, pg. 482-500, (1997).

DEFINITIONS

General

The term "individual" or "subject", includes human beings and non-human animals. With respect to the disclosed radioprotective and cytoprotective methods, these terms refer, unless the context indicates otherwise, to an organism that is scheduled to incur, or is at risk for incurring, or has incurred, exposure to ionizing radiation or exposure to one or more cytotoxic chemotherapeutic agents.

The expression "effective amount" when used to describe therapy to a patient suffering from a proliferative disorder, refers to the amount of a compound of Formula I that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation. The term "effective amount" is inclusive of amounts of a compound of Formula I that is metabolized to an active metabolite in an amount that inhibits the growth of tumor cells or induces apoptosis of cancer cells.

The term "antibody" is intended to encompass not only intact antigen-binding immunoglobulin molecules, but also to include antigen-binding fragments thereof such as Fab, Fab' and F(ab')$_2$ fragments, or any other fragment retaining the antigen-binding ability of an intact antibody.

The expression "humanized antibody" refers to an antibody that has its complementary determining regions (CDR's) derived from a non-human species immunoglobulin, and the remainder of the antibody molecule derived from a human immunoglobulin.

The expression "chimeric antibody" means an antibody comprising a variable region and a constant region derived from different species.

The expression "humanized chimeric antibody" means a chimeric antibody in which at least the constant region is human-derived.

The expression "monospecific polyclonal antibody" means an antibody preparation comprising multiple antibody species having specificity for a single antigen.

The term "proliferative disorder" means a disorder wherein cells are made by the body at an atypically accelerated rate.

Radioprotection

As used herein, "ionizing radiation" is radiation of sufficient energy that, when absorbed by cells and tissues, induces formation of reactive oxygen species and DNA damage. This type of radiation includes X-rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), wherein 1 rad=0.01 Gy, or in units of dose equivalence, such as the rem or sievert (Sv), wherein 1 rem=0.01 Sv.

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or in reducing the proliferation, of abnormally proliferating cells in an individual. As used with respect to bone marrow purging, "effective amount of ionizing radiation" means an amount of ionizing radiation effective in killing, or in reducing the proliferation, of malignant cells in a bone marrow sample removed from an individual.

By "acute exposure to ionizing radiation" or "acute dose of ionizing radiation" is meant a dose of ionizing radiation absorbed by an individual in less than 24 hours. The acute dose may be localized, as in radiotherapy techniques, or may be absorbed by the individual's entire body. Acute doses are typically above 10,000 millirem (0.1 Gy), but may be lower.

By "chronic exposure to ionizing radiation" or "chronic dose of ionizing radiation" is meant a dose of ionizing radiation absorbed by an individual over a period greater than 24 hours. The dose may be intermittent or continuous, and may be localized or absorbed by the individual's entire body. Chronic doses are typically less than 10,000 millirem (0.1 Gy), but may be higher.

By "at risk of incurring exposure to ionizing radiation" is meant that an individual may intentionally, e.g., by scheduled radiotherapy sessions, or inadvertently be exposed to ionizing radiation in the future. Inadvertent exposure includes accidental or unplanned environmental or occupational exposure.

By "effective amount of a radioprotective compound" is meant an amount of compound of Formula I effective to reduce or eliminate the toxicity associated with radiation in normal cells of the individual, and also to impart a direct cytotoxic effect to abnormally proliferating cells in the individual. As used with respect to bone marrow purging, "effective amount" of the radioprotective compound of Formula I means an amount of compound effective to reduce or eliminate the toxicity associated with radiation in bone marrow removed from an individual, and also to impart a direct cytotoxic effect to malignant cells in the bone marrow removed from the individual.

Cytoprotection

By "effective amount" of the mitotic phase cell cycle inhibitor or topoisomerase inhibitor is meant an amount of said inhibitor effective in killing or reducing the proliferation of cancer cells in a host animal.

By "effective amount" of the cytoprotective compound of Formula I is meant an amount of compound effective to reduce the toxicity of the mitotic phase cell cycle inhibitor or topoisomerase inhibitor on normal cells of the animal.

The expression "cell cycle" refers to the usual description of cell development in terms of a cycle consisting of a series of phases-interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, S and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

By "mitotic phase cell cycle inhibitor" is meant a chemical agent whose mechanism of action includes inhibition of a cell's passage through any portion of the mitotic (M) phase of the cell cycle.

By "topoisomerase inhibitor" is meant a chemical agent whose mechanism of action includes interfering with the function of a topoisomerase.

By "topoisomerase" is meant an enzyme that catalyzes the conversion of DNA from one topological form to another by introducing transient breaks in one or both strands of a DNA duplex.

"Topological isomers" are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA.

Chemical

The term "alkenyl" employed alone or in combination with other terms, means, unless otherwise stated, a stable straight chain, branched chain or cyclic hydrocarbon group having the stated number of carbon atoms and containing at least one carbon-carbon double bond. Examples include vinyl, propenyl(allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

The term "alkyl", by itself or as part of another substituent, e.g., alkoxy, haloalkyl or aminoalkyl, means, unless otherwise stated, a saturated hydrocarbon radical having the number of carbon atoms designated (i.e. $C_1$-$C_6$ means one to six carbons) and includes straight, branched chain, cyclic and polycyclic groups. Examples include: methyl, ethyl, propyl, isopropyl, butyl, isobutyl, tert-butyl, pentyl, neopentyl, hexyl, cyclohexyl, norbornyl and cyclopropylmethyl. Most preferred is ($C_1$-$C_3$)alkyl, particularly ethyl, methyl and isopropyl.

Substituted alkyl or alkenyl means alkyl or alkenyl, as defined above, substituted by one, two or three substituents selected from the group consisting of halogen, —OH, —O($C_1$-$C_4$)alkyl, —NH$_2$, —N(CH$_3$)$_2$, —CO$_2$H, —CO$_2$($C_1$-$C_4$)alkyl, —CF$_3$, —CONH$_2$, —SO$_2$NH$_2$, —C(=NH)NH$_2$, —CN and —NO$_2$, preferably containing one or two substituents selected from halogen, —OH, —NH$_2$, —N(CH$_3$)$_2$, trifluoromethyl and —O$_2$H, more preferably selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle.

Examples of amino groups include: —NH$_2$, methyl amino, diethyl amino, anilino, benzyl amino, piperidinyl, piperazinyl and indolinyl.

The term "aromatic" refers to a carbocycle or heterocycle having one or more polyunsaturated rings having aromatic character ((4n+2) delocalized π(pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-($C_1$-$C_3$)alkyl" means a radical wherein a one to three carbon alkylene chain is attached to an aryl group, e.g., —CH$_2$CH$_2$-phenyl. Preferred is aryl(CH$_2$)— and aryl (CH(CH$_3$))—. The term "substituted aryl-($C_1$-$C_3$)alkyl" means an aryl-$C_1$-$C_3$)alkyl radical in which the aryl group is substituted. Preferred is substituted aryl(CH$_2$)—. Similarly, the term "heteroaryl($C_1$-$C_3$)alkyl" means a radical wherein a one to three carbon alkylene chain is attached to a heteroaryl group, e.g., —CH$_2$CH$_2$-pyridyl. Preferred is heteroaryl (CH$_2$)—. The term "substituted heteroaryl-($C_1$-$C_3$)alkyl" means a heteroaryl-($C_1$-$C_3$)alkyl radical in which the heteroaryl group is substituted. Preferred is substituted heteroaryl(CH$_2$)—.

The term "arylene," by itself or as part of another substituent means, unless otherwise stated, a divalent aryl radical. Preferred are divalent phenyl radicals, particularly 1,4-divalent phenyl radicals.

The term "cycloalkyl" refers to ring-containing alkyl radicals. Examples include cyclohexyl, cyclopentyl, cyclopropyl methyl and norbornyl The terms "halo" or "halogen" by themselves or as part of another substituent, e.g., haloalkyl, mean, unless otherwise stated, a fluorine, chlorine, bromine, or iodine atom, preferably, fluorine, chlorine, or bromine, more preferably, fluorine or chlorine.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group may be the same or different.

The term "heteroalkyl" by itself or in combination with another term means, unless otherwise stated, a stable straight or branched chain radical consisting of the stated number of carbon atoms and one, two three or four heteroatoms selected from the group consisting of O, N, and S, and wherein the sulfur heteroatoms may be optionally oxidized and the nitrogen heteroatoms may be optionally quaternized or oxidized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S-CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S-S-CH$_3$.

The term "heteroalkenyl" by itself or in combination with another term means, unless otherwise stated, a stable straight or branched chain monounsaturated or di-unsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A monocyclic heteroaryl group is a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated. Examples of polycyclic heteroaryl groups containing a partially saturated ring include tetrahydroquinolyl and 2,3-dihydrobenzofuryl. For compounds of Formula I, the attachment point on ring A or ring B is understood to be on an atom which is part of an aromatic monocyclic ring or a ring component of a polycyclic aromatic which is itself an aromatic ring.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: Indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The term "heteroarylene," by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from pyridine, piperazine, pyrimidine, pyrazine, furan, thiophene, pyrrole, thiazole, imidazole and oxazole.

For compounds of the present invention, when an aromatic or heteroaromatic ring is attached to a position and the ring comprises a polycyclic ring which is partially saturated, the attachment point on the aromatic or heteroaromatic ring is on a ring atom of an aromatic ring component of the polycyclic ring. For example on the partially saturated heteroaromatic ring, 1,2,3,4-tetrahydroisoquinoline, attachment points would be ring atoms at the 5-, 6-, 7- and 8-positions.

The aforementioned listing of heterocyclyl and heteroaryl moieties is intended to be representative, not limiting.

The term "hydrocarbyl" refers to any moiety comprising only hydrogen and carbon atoms. Preferred heteroaryl groups are $(C_1-C_{12})$hydrocarbyl, more preferred are $(C_1-C_7)$hydrocarbyl, most preferred are benzyl and $(C_1-C_6)$alkyl.

The expression "carboxy terminally linked peptidyl residue" refers to a peptide radical as a substituent on a molecule of Formula I. The radical is bonded through the carboxyl functionality of the peptidyl residue to form a carboxamide or carboxylic ester as shown in a representative example in Scheme 1 below.

Scheme 1

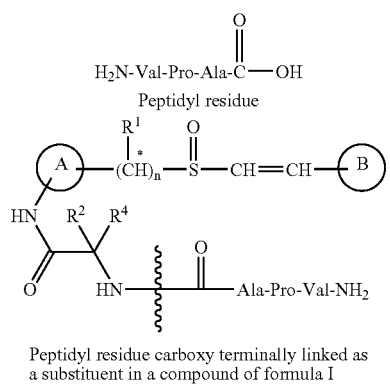

Peptidyl residue carboxy terminally linked as a substituent in a compound of formula I The amino acid residues comprising the amino terminally linked peptidyl residue may comprise natural or unnatural amino acids or a combination thereof. Unnatural amino acids are amino acids other than the twenty essential amino acids. One example of an unnatural amino acid is a D-amino acid, i.e., an amino acid having a stereochemistry opposite the stereochemistry of natural L-amino acids. Another example of an unnatural amino acid is an amino acid having a side chain that differs from the side chains occurring in the natural amino acids, for example α-ethyl glycine or α-phenyl glycine. A third example is an amino acid having a backbone variation. Examples of amino acid backbone variations include β-alanine and β-turn mimetics such as Freidinger's lactam. A fourth example of an unnatural amino acid is an amino acid having two α-substituents, e.g., α,α-dimethyl glycine.

The amino terminus of the carboxy terminally linked peptidyl residue may be an unsubstituted amino group, or may be substituted. Substitutions on the amino terminus include mono- and di-$(C_1-C_6$ alkyl), —C(=O)($C_1-C_6$ alkyl), —C(=O)O($C_1-C_7$)hydrocarbyl) and commonly employed nitrogen protecting groups such as t-butoxycarbonyl (BOC), carbobenxyloxy (CBZ), 2,4-dimethoxybenyl and FMOC.

The expression "amino terminally linked peptidyl residue" refers to a peptide radical as a substituent on a compound of Formula I. The radical is bonded through the terminal amino functionality of the peptidyl residue to form a carboxamide, sulfonamide, urea or thiourea as shown in a representative example in Scheme 2 below.

Scheme 2

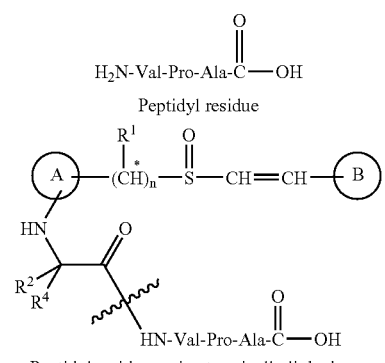

Peptidyl residue amino terminally linked as a substituent in a compound of formula I The carboxy terminus of the amino terminally linked peptidyl residue may be a free carboxyl group or a salt thereof, or may be derivatized as an ester or amide. Suitable esters include alkyl, aryl and arylalkyl esters. Suitable amides include the primary amide and secondary and tertiary amides comprising one or two nitrogen substituents independently selected from ($C_1$-$C_3$)alkyl, preferably methyl or ethyl; aryl, preferably phenyl; and aryl($C_1$-$C_3$)alkyl groups, preferably benzyl or substituted benzyl.

As with the carboxy terminally linked peptidyl residues, the amino acids comprising the amino terminally linked peptidyl residue may comprise natural or unnatural amino acids or a combination thereof.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted carbon may be the any carbon in the chain having at least two substitutable hydrogens, including a terminal $CH_3$ and the proximal carbon through which the difluoro($C_x$-$C_y$)alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

SUMMARY OF THE INVENTION

It is an object of the invention to provide compounds, pharmaceutical compositions and therapeutic methods. The biologically active compounds are in the form of α,β-unsaturated sulfoxides, and salts thereof.

It is an object of the invention to provide compounds, compositions and methods for the treatment and/or prevention of cancer and other proliferative disorders.

It is an object of the invention to provide compounds which are selective in killing tumor cells at therapeutically useful concentrations.

It is an object of the invention to provide compounds, compositions and methods for inducing neoplastic cells to selectively undergo apoptosis.

It is a further object of this invention to provide compounds, compositions and methods which enable prophylactic treatment of proliferative disorders.

It is a further object of this invention to provide compounds, compositions and methods for protecting normal cells and tissues from the cytotoxic and genetic effects of exposure to ionizing radiation, in individuals who have incurred, will in the future incur, or are at risk for incurring exposure to ionizing radiation.

The exposure to ionizing radiation may occur in controlled doses during the treatment of cancer and other proliferative disorders, or may occur in uncontrolled doses beyond the norm accepted for the population at large during high risk activities or environmental exposures.

It is an object of the invention to provide compositions and methods for protecting individuals from the cytotoxic side effects of chemotherapeutic agents, particularly mitotic phase cell cycle inhibitors and topoisomerase inhibitors, used in the treatment of cancer and other proliferative disorders.

It is an object of the invention to provide a method for treating cancer or other proliferative disorder which reduces or eliminates cytotoxic effects on normal cells.

It is an object of the invention to enhance the effects of chemotherapeutic agents, particularly mitotic phase cell cycle inhibitors and topoisomerase inhibitors, used for the treatment of cancer or other proliferative disorders.

It is an object of the present invention to provide a therapeutic program for treating cancer or other proliferative disorder which includes administration of a cytoprotective compound prior to administration of a chemotherapeutic agent, which cytoprotective compound induces a reversible cycling quiescent state in non-tumored tissues.

It is an object of the invention to provide a method for safely increasing the dosage of chemotherapeutic agents, particularly mitotic phase cell cycle inhibitors and topoisomerase inhibitors, used in the treatment of cancer and other proliferative disorders.

According to one aspect, the invention is directed to novel compounds of Formula I:

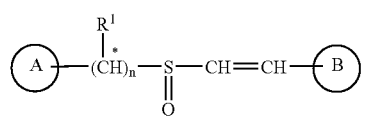

wherein:
A is substituted or unsubstituted aryl, or substituted or unsubstituted heteroaryl;
B is substituted or unsubstituted aryl, or substituted or unsubstituted heteroaryl;
n is 0 or 1; and
$R^1$ is —H; —($C_1$-$C_8$)hydrocarbyl, preferably —($C_1$-$C_6$) alkyl, more preferably —($C_1$-$C_6$)alkyl, most preferably —$CH_3$ or —$C_2H_5$; —CN; —$CO_2$($C_1$-$C_6$)alkyl, preferably —$CO_2$($C_1$-$C_4$)alkyl, most preferably —$CO_2CH_3$, —$CO_2$ (ethyl) or —$CO_2$(t-butyl); or halo($C_1$-$C_6$)alkyl, preferably trifluoro($C_1$-$C_6$)alkyl or difluoro($C_1$-$C_6$)alkyl, more preferably trifluoro($C_1$-$C_3$)alkyl or difluoro($C_1$-$C_3$)alkyl, most preferably —$CF_3$ or —$CHF_2$;

wherein:
the configuration of the substituents on the carbon-carbon double bond is either E- or Z—;
the configuration of the substituents on the sulfoxide sulfur atom is R—, S— or any mixture of R— and S—;
* indicates that, when $R^1$ is other than —H, the configuration of the substituents on the designated carbon atom is R—, S— or any mixture of R— and S—; or a salt thereof;
provided that when A and B are both phenyl, at least one of A or B is substituted.

According to some embodiments, A and B are independently selected from the group consisting of substituted and unsubstituted aryl.

According to other embodiments, A and B are independently selected from the group consisting of substituted and unsubstituted heteroaryl.

According to still other embodiments A is substituted or unsubstituted aryl and B is substituted or unsubstituted heteroaryl.

According to still other embodiments B is substituted or unsubstituted aryl and A is substituted or unsubstituted heteroaryl.

According to some embodiments, the configuration of the substituents on the sulfoxide sulfur atom is a racemic mixture of R— and S—.

According to some embodiments, the configuration of the substituents on the * designated carbon atom is a racemic mixture of R— and S—.

According to some embodiments, n is 1.

According to some embodiments, $R^1$ is —H

According to some sub-embodiments, the compounds of Formula I are compounds of Formula Ie:

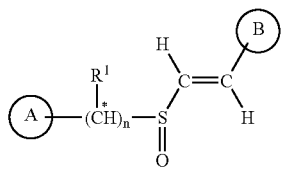

Ie wherein the configuration of the substituents on the two carbons of the carbon-carbon double bond is E-.

According to other sub-embodiments, the compounds of Formula I are compounds of Formula Iz:

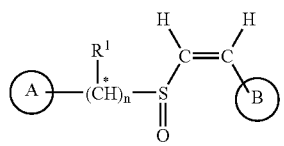

Iz wherein the configuration of the substituents on two carbons of the carbon-carbon double bond is Z—.

Substituents for substituted aryl and heteroaryl groups comprising A and B are preferably independently selected from the group consisting of halogen; —($C_1$-$C_8$)hydrocarbyl, preferably —($C_1$-$C_6$)alkyl, more preferably —($C_1$-$C_3$)alkyl, most preferably —$CH_3$ and —$C_2H_5$; —C(=O)$R^2$; —$NR^2_2$; —NHC(=O)$R^3$; —NHSO$_2R^3$; —NHR$^4$; —NHCR$^2R^4$C(=O)$R^6$; —NHSO$_2R^3$; —C(=O)O$R^2$; —C(=O)NHR$^2$; —NO$_2$; —CN; —O$R^2$; —P(=O)(OH)$_2$; dimethylamino($C_2$-$C_6$ alkoxy); —NHC(=N$R^2$)NHR$^2$; —($C_1$-$C_6$)haloalkyl, preferably trifluoro($C_1$-$C_6$)alkyl and difluoro($C_1$-$C_6$)alkyl, more preferably trifluoro($C_1$-$C_3$)alkyl and difluoro($C_1$-$C_3$)alkyl, most preferably —$CF_3$ and —$CHF_2$; —($C_1$-$C_6$)haloalkoxy, preferably trifluoro($C_1$-$C_6$)alkyl and difluoro($C_1$-$C_6$)alkyl, more preferably trifluoro($C_1$-$C_3$)alkoxy and difluoro($C_1$-$C_3$)alkoxy, most preferably —OCF$_3$ and —OCHF$_2$; and —N=CH—R$^7$;

each $R^3$ is independently selected from the group consisting of —H; —($C_1$-$C_8$)hydrocarbyl, preferably —($C_1$-$C_6$)alkyl, more preferably —($C_1$-$C_3$)alkyl, most preferably —$CH_3$ and —$C_2H_5$; —O($C_1$-$C_8$)hydrocarbyl, preferably —O($C_1$-$C_6$)alkyl, more preferably —O($C_1$-$C_3$)alkyl, most preferably —OCH$_3$ and —OC$_2H_5$; substituted and unsubstituted aryl, preferably substituted and unsubstituted phenyl; substituted heterocyclyl($C_1$-$C_3$)alkyl; heteroaryl($C_1$-$C_3$)alkyl; —($C_2$-$C_{10}$)heteroalkyl; —($C_1$-$C_6$)haloalkyl, preferably trifluoro($C_1$-$C_6$)alkyl or difluoro($C_1$-$C_6$)alkyl, more preferably trifluoro($C_1$-$C_3$)alkyl and difluoro($C_1$-$C_3$)alkyl, most preferably —CF$_3$ and —CHF$_2$; —CR$^2R^4$NHR$^5$; —N(R$^2$)$_2$; —($C_1$-$C_3$)alkyleneNH$_2$; —($C_1$-$C_3$)alkylene-N(CH$_3$)$_2$; —($C_1$-$C_3$)perfluoroalkylene-N(CH$_3$)$_2$; —($C_1$-$C_3$) alkylene-N$^+$((C$_1$-$C_3$)alkyl)$_3$; —($C_1$-$C_3$) alkylene-N$^+$(CH$_2$CH$_2$OH)$_3$; —($C_1$-$C_3$)alkylene-OR$^2$; —($C_1$-$C_4$) alkylene-CO$_2R^2$; —($C_1$-$C_4$)alkylene -C(=O)halogen; —($C_1$-$C_3$)alkylene-C(=O)(C$_1$-$C_3$)alkyl; and —($C_1$-$C_4$)perfluoroalkylene-CO$_2R^2$;

each $R^4$ is independently selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —(CH$_2$)$_4$—NH2, —(CH$_2$)$_2$—S-CH$_3$, phenyl, —CH$_2$-phenyl, —CH$_2$—OH, —CH(OH)—CH$_3$, —CH$_2$-(3-indolyl), and —CH$_2$-(4-hydroxyphenyl);

each $R^5$ is independently selected from the group consisting of —H and a carboxy terminally linked peptidyl residue containing from 1to 3 amino acids in which the terminal amino group of the peptidyl residue is present as a functional group selected from the group consisting of —NH$_2$; —NHC(=O)(C$_1$-$C_6$)alkyl; —NH(C$_1$-$C_6$)alkyl; —NH(C$_1$-$C_6$ alkyl)$_2$ and —NHC(=O)O(C$_1$-$C_7$)hydrocarbyl, preferably —NHC(=O)O(C$_1$-$C_6$)alkyl and —NHC(=O)O-benzyl;

each $R^6$ is independently selected from the group consisting of —OR$^2$ and an N-terminally linked peptidyl residue containing from 1to 3 amino acids in which the terminal carboxyl group of the peptidyl residue is present as a functional group selected from the group consisting of —CO$_2R^2$ and —C(=O)NR$^2_2$; and each $R^7$ is independently selected from the group consisting of substituted and unsubstituted aryl, preferably substituted and unsubstituted phenyl; and substituted and unsubstituted heteroaryl; or a salt of such a compound, preferably a pharmaceutically acceptable salt of such a compound.

Substituents on substituted aryl $R^3$ and $R^7$, and on substituted heteroaryl $R^7$, are preferably selected from halogen, (C$_1$-$C_8$)hydrocarbyl, —NH$_2$, —NO$_2$, N-methylpiperazinyl, —OH and —O(C$_1$-$C_8$)hydrocarbyl.

Substituents on substituted heterocyclyl(C$_1$-$C_3$)alkyl $R^3$ are preferably selected from —(C$_1$-$C_7$)hydrocarbyl, more preferably —(C$_1$-$C_6$)alkyl; —C(=O)(C$_1$-$C_6$)alkyl, more preferably —C(=O)(C$_1$-$C_3$)alkyl, most preferably acetyl; and —(C$_1$-$C_6$)perfluoroalkyl, more preferably —(C$_1$-$C_3$)perfluoroalkyl, most preferably —CF$_3$.

Compounds of Formula IA

According to one embodiment of the compounds of Formula I, there is provided a compound according to Formula IA:

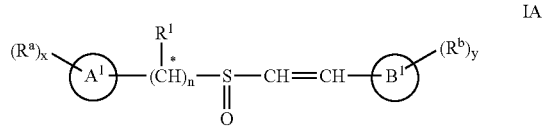

IA wherein:

$A^1$ and $B^1$ are independently aryl or heteroaryl;

x and y are independently 0, 1, 2, 3, 4 or 5;

each $R^a$ is independently selected from the group consisting of halogen; —($C_1$-$C_8$)hydrocarbyl, —C(=O)$R^2$, —$NR^2{}_2$, —NHC(=O)$R^3$, —NHSO$_2R^3$, —NHR$^4$, —NHCR$^2R^4$C(=O)$R^6$, —C(=O)O$R^2$, —C(=O)NH$R^2$; —NO2, —CN, —O$R^2$, —P(=O)(OH)$_2$, dimethylamino($C_2$-$C_6$ alkoxy), —NHC(=NH)NH$R^2$, —($C_1$-$C_6$)haloalkyl, —($C_1$-$C_6$)haloalkoxy and —N=CH—$R^7$;

each $R^b$ is independently selected from the group consisting of —($C_1$-$C_8$)hydrocarbyl, —C(=O)$R^2$, halogen, —NO$_2$, —CN, —O$R^2$, —C(=O)O$R^2$, —$NR^2{}_2$, ($C_1$-$C_6$)haloalkyl and ($C_1$-$C_6$)haloalkoxy; or a salt of such a compound, preferably a pharmaceutically acceptable salt of such a compound;

provided that:

the highest value of x or y is equal to the number of substitutable hydrogen atoms in the ring to which x or y is attached; and when $A^1$ and $B^1$ are both phenyl, the sum of x and y is greater than zero.

According to some embodiments of the compounds of Formula IA, the sum of x and y is greater than zero.

According to other embodiments of the compounds of Formula IA, the sum of x and y is greater than one.

According to yet other embodiments of the compounds of Formula IA, the sum of x and y is greater than two.

According to still other embodiments of the compounds of Formula IA, the sum of x and y is greater than three.

According to some embodiments of the compounds of Formula IA, both x and y are greater than zero.

According to other embodiments of the compounds of Formula IA, both x and y are greater than one.

According to still other embodiments of the compounds of Formula IA, both x and y are greater than two.

A. First Embodiment of Compounds of Formula IA

According to a First Embodiment of the compounds of Formula IA, $A^1$ is an aryl ring.

Preferred compounds include, for example: (1E)-2-(4-fluorophenyl)-1-[(naphthylmethyl)sulfinyl]ethene; (1E)-2-(4-chlorophenyl)-1-[(naphthylmethyl)sulfinyl]ethene; (1E)-2-4-bromophenyl)-1-[(naphthylmethyl)sulfinyl]ethene; (1E)-2-(2-nitrophenyl)-1-[(naphthylmethyl)sulfinyl]ethene; (1E)-2-(3-nitrophenyl)-1-[(naphthylmethyl)sulfinyl]ethene; (1E)-2-(4-nitrophenyl)-1-[(naphthylmethyl)sulfinyl]ethene; and salts thereof.

1. Compounds of Formula IB

According to a sub-embodiment of the First Embodiment of the Compounds of Formula IA, there is provided a compound according to Formula IB:

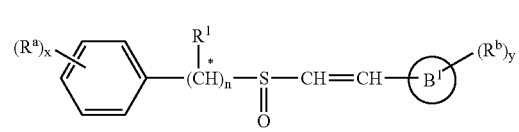

IB or a salt thereof.

Preferably, for compounds of Formula IB, each $R^a$ is independently selected from the group consisting of halogen, ($C_1$-$C_6$)alkyl, ($C_1$-$C_6$)alkoxy, —NO$_2$, —CN, —C(=O)O$R^2$, —OH, —NH$_2$, ($C_1$-$C_6$)trifluoroalkoxy and —CF$_3$.

a. Compounds of Formula IC

According to a sub-embodiment of the compounds according to Formula IB, there is provided a compound according to Formula IC:

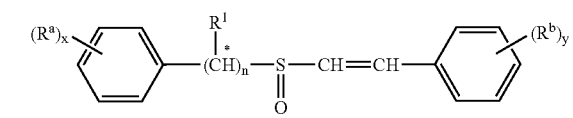

IC or a salt thereof.

Preferably, for compounds of Formula IC, each $R^a$ and $R^b$ are independently selected from the group consisting of halogen, ($C_1$-$C_6$)alkyl, ($C_1$-$C_6$)alkoxy, —NO$_2$, —CN and —CF$_3$.

Preferably, for compounds according to Formula IC, the configuration of the substituents on the carbon-carbon double bond is E-.

Preferably for compounds of Formula IC, x and y are independently 0, 1 or 2.

Preferably for compounds of Formula IC, n is 1.

Preferably for compounds of Formula IC, $R^1$ is —H

Preferred compounds according to Formula IC include, for example: (1E)-1-{[(3-amino-4-methoxyphenyl)methyl]sulfinyl}-2-(2,4,6-trimethoxyphenyl)ethene; (1E)-1-{[(3-hydroxy-4-methoxyphenyl)methyl]sulfinyl}-2-(2,4,6-trimethoxyphenyl)ethene; (1E)-1-{[(4-methoxy-3-nitrophenyl)methyl]sulfinyl}-2-(2,4,6-trimethoxyphenyl)ethene; 2-({[5-({[(1E)-2-(2,4,6-trimethoxyphenyl)vinyl]sulfinyl}-methyl)-2-methoxyphenyl]amino}sulfonyl)acetic acid; 2-{N -[5-({[(1E)-2-(2,4,6-trimethoxyphenyl)vinyl]sulfinyl}-methyl)-2-methoxy -phenyl]carbamoyl}acetic acid; [5-({[(1E)-2-(2,4,6-trimethoxyphenyl)vinyl]sulfinyl}methyl)-2-methoxyphenyl]aminocarboxamidine; 2-{[5-({[(1E)-2-(2,4,6-trimethoxyphenyl)vinyl]sulfinyl}methyl)-2-methoxyphenyl]amino}acetic acid; N-[5-({[(1E)-2-(2,4,6-trimethoxyphenyl)vinyl]sulfinyl}methyl)-2-methoxyphenyl](3,5-dinitrophenyl)carboxamide; N-[5-({[(1E)-2-(2,4,6-trimethoxyphenyl)vinyl]sulfinyl}methyl)-2-methoxyphenyl](3,5-diaminophenyl) carboxamide; N-[5-({[(1E)-2-(2,4,6-trimethoxyphenyl) vinyl]sulfinyl}methyl)-2-methoxyphenyl]-2-chloroacetamide; N-[5-({[(1E)-2-(2,4,6-trimethoxyphenyl) vinyl]sulfinyl}methyl)-2-methoxyphenyl]-2-(4-methylpiperazinyl) -acetamide; N-[5-({[(1E)-2-(2,4,6-trimethoxyphenyl)vinyl]sulfinyl}methyl)-2-methoxyphenyl]benzamide; N-[5-({[(1E)-2-(2,4,6-trimethoxyphenyl)vinyl]sulfinyl}methyl)-2-methoxyphenyl](4-nitrophenyl)carboxamide; N-[5-({[(1E)-2-(2,4,6-trimethoxyphenyl)vinyl]sulfinyl}methyl)-2-methoxyphenyl](4-aminophenyl)carboxamide; (1E) -1-[({3-[(1Z)-1-aza-2-(4-nitrophenyl)vinyl]-4-methoxyphenyl}methyl)sulfinyl]-2-(2,4,6-trimethoxyphenyl)ethene; N-[5-({[(1E)-2-(2,4,6-trimethoxyphenyl)vinyl]sulfinyl}methyl)-2-methoxyphenyl](2R)-2,6-diaminohexanamide; N-[5-(({[(1E)-2-(2,4,6-trimethoxyphenyl) vinyl]sulfinyl}methyl)-2-methoxyphenyl](2R)-2-amino-3-hydroxypropanamide; N-[5-({[(1E)-2-(2,4,6-trimethoxyphenyl)vinyl]sulfinyl}methyl)-2-methoxyphenyl](2S)-2-amino-3-hydroxypropanamide; N-[5-({[(1E)-2-(2,4,6-trimethoxynhenyl)vinyl]sulfinyl}methyl)-2-methoxyphenyl]aminamide; (1E)-1-({[4-methoxy-3-(methylamino)phenyl] methyl}sulfinyl)-2-(2,4,6-trimethoxyphenyl)ethene; N-[5-({[(1E)-2-(2,4,6-trimethoxyphenyl)vinyl]sulfinyl}methyl)-2-methoxyphenyijacetamide; [5-((([(1E)-2-(2,4,6-trimethoxyphenyl)vinyl]sulfinyl}methyl)-2-methoxyphenyl][(2,4-dinitrophenyl)sulfonyl]amine; [5-({[(1E)-2-(2,4,6-trimethoxyphenyl)vinyl]sulfinyl}methyl)-2-methoxyphenyl][(2,4-diaminophenyl)sulfonyl]amine; N-[5-({[(1E)-2-(2,4,6-trimethoxyphenyl)vinyl]sulfinyl}methyl)-2-methoxyphenyl]-2-(dimethylamino)acetamide; 2-{[5-({[(1E)-2-(2,4,6-trimethoxyphenyl)vinyl]sulfinyl}methyl)-2-methoxyphenyl]amino}propanoic acid; N-[5-({[(1E)-2-(2,4,6-trimethoxyphenyl)vinyl]sulfinyl}methyl)-2-methoxyphenyl][4-(4-methyl-piperazinyl) phenyl]carboxamide; N-[5-({[(1E)-2-(2,4,6-trimethoxyphenyl)vinyl]sulfinyl}-methyl)-2-methoxyphenyl]-2-hydroxyacetamide; N-[5-({[(1E)-2-(2,4,6-trimethoxyphenyl)vinyl]sulfinyl}methyl)-2-methoxyphenyl]-2-pyridylacetamide; {N-[5-({[(1E)-2-(2,4,6-trimethoxyphenyl)vinyl]sulfinyl}methyl)-2-methoxyphenyl]carbamoyl}methyl acetate; N-[5-({[(1E)-2-(2,4,6-trimethoxyphenyl)vinyl]sulfinyl}methyl)-2-methoxyphenyl]-2-hydroxypropanamide; N-[5-({[(1E)-2-(2,4,6-trimethoxyphenyl)vinyl]sulfinyl}methyl)-2-methoxyphenyl]-2-(triethylamino)acetamide; N-[5-({[(1E)-2-(2,4,6-trimethoxyphenyl)vinyl]-sulfinyl}methyl)-2-methoxyphenyl]-2-[tris(2-hydroxyethyl)amino]acetamide; N-[5-({[(1E)-2-(2,4,6-trimethoxyphenyl)vinyl]sulfinyl}methyl)-2-methoxyphenyl]-2-hydroxy-2-methyl-propanamide; 1-{N-[5-({[(1E)-2-(2,4,6-trimethoxyphenyl)vinyl]sulfinyl}-methyl)-2-methoxyphenyl]carbamoyl}-isopropyl acetate; N-[5-({[(1E)-2-(2,4,6-trimethoxyphenyl)vinyl]sulfinyl}methyl)-2-methoxyphenyl]-2,2,2-trifluoroacetamide; [5-({[(1E)-2-(2,4,6-trimethoxyphenyl)vinyl]sulfinyl}methyl)-2-methoxyphenyl][(trifluoromethyl)sulfonyl]amine; 3-{N-[5-({[(1E)-2-(2,4,6-trimethoxyphenyl)vinyl]sulfinyl}-methyl)-2-methoxyphenyl]carbamoyl}propanoic acid; 3-(N-[5-({[(1E)-2-(2,4,6-trimethoxyphenyl)vinyl]sulfinyl}-methyl)-2-methoxyphenyl]carbamoyl}propanoyl chloride; 3-[({N-[5-({[(1E)-2-(2,4,6-trimethoxyphenyl)vinyl]sulfinyl}-methyl)-2-methoxyphenyl]carbamoyl}-methyl)oxycarbonyl]propanoic acid; 4-{N-[5-({[(1E)-2-(2,4,6-trimethoxyphenyl)vinyl]sulfinyl}-methyl)-2-methoxyphenyl]carbamoyl}butanoic acid; N-[5-({[(1E)-2-(2,4,6-trimethoxyphenyl)vinyl]sulfinyl}methyl)-2-methoxyphenyl]-2-(phosphonooxy)acetamide, disodium salt; 4-{[5-({[(1E)-2-(2,4,6-trimethoxyphenyl)vinyl]sulfinyl}methyl)-2-methoxyphenyl]amino}butanoic acid; 3-{[5-({[(1E)-2-(2,4,6-trimethoxyphenyl)vinyl]sulfinyl}methyl)-2-methoxyphenyl]amino}propanoic acid; N-[5-({[(1E)-2-(2,4,6-trimethoxyphenyl)vinyl]sulfinyl}methyl)-2-methoxyphenyl]methoxycarboxamide; [5-({[(1E)-2-(2,4,6-trimethoxyphenyl)vinyl]sulfinyl}methyl)-2-methoxyphenyl][(4-methoxyphenyl)sulfonyl]amine; {N-[5-({[(1E)-2-(2,4,6-trimethoxyphenyl)vinyl]sulfinyl}methyl)-2-methoxyphenyl]carbamoyl}ethyl acetate; methyl-3-{N-[5-({[(1E)-2-(2,4,6-trimethoxyphenyl)vinyl]sulfinyl}-methyl)-2-methoxyphenyl]carbamoyl}propanoate; ethyl-2-{N-[5-({[(1E)-2-(2,4,6-trimethoxyphenyl)vinyl]sulfinyl}-methyl)-2-methoxyphenyl]carbamoyl}acetate; N-[5-({[(1E)-2-(2,4,6-trimethoxyphenyl)vinyl]sulfinyl}methyl)-2-methoxyphenyl]-2,2,3,3,3-pentafluoropropanamide; methyl-2-{N-[5-({[(1E)-2-(2,4,6-trimethoxyphenyl)vinyl]-sulfinyl}methyl)-2-methoxyphenyl]carbamoyl}-2,2-difluoroacetate; 3-{N-[5-({[(1E)-2-(2,4,6-trimethoxyphenyl)vinyl]sulfinyl}-methyl)-2-methoxyphenyl]carbamoyl}-2,2,3,3-tetrafluoropropanoic acid; N-[5-({[(1E)-2-(2,4,6-trimethoxyphenyl)vinyl]sulfinyl}methyl)-2-methoxyphenyl]-2-aminoacetamide; 2-{N-[5-({[(1E)-2-(2,4,6-trimethoxyphenyl)vinyl]sulfinyl}-methyl)-2-methoxyphenyl]carbamoyl}-2,2-difluoroacetic acid; N-[5-({[(1E)-2-(2,4,6-trimethoxyphenyl)vinyl]sulfinyl}methyl)-2-methoxyphenyl]-2-(dimethylamino)-2,2-difluoroacetamide, 4-((1E)-2-{[(4-fluorophenyl)methyl]-sulfinyl}vinyl)benzoic acid; 4-({1E)-2-{[(4-iodophenyl)methyl]sulfinyl}vinyl)benzoic acid; 4-({1E)-2-{[(4-chlorophenyl)methyl]sulfinyl}vinyl)benzoic acid; 1-[5-((1E)-2-{[(4-chlorophenyl)methyl]sulfinyl}vinyl)-2-fluoro-phenyl]-2-(dimethylamino)ethan-1-one; (1E)-2-(2,4-difluorophenyl)-1-{[(4-bromophenyl)methyl]sulfinyl}ethene; (1E)-2-(3-amino-4-fluorophenyl)-1-{[(4-chlorophenyl)methyl]sulfinyl}ethene; (1E)-1-{[(4-fluorophenyl)methyl]sulfinyl}-2-(2,3,4,5,6-pentafluorophenyl)ethene; (1E)-1-{[(4-chlorophenyl)methyl]sulfinyl}-2-(2,3,4,5,6-pentafluorophenyl)ethene; (1E)-1-{[(4-bromophenyl)methyl]sulfinyl}-2-(2,3,4,5,6-pentafluorophenyl)ethene; (1E)-2-(4-fluorophenyl)-1-{[(2,3,4,5,6-pentafluorophenyl)-methyl]sulfinyl}ethene; (1E)-2-(4-chlopheny)-1-{[(2,3,4,5,6-pentafluorophenyl)-methyl]sulfinyl}ethene; (1E)-2-(4-bromophenyl)-1-{[(2,3,4,5,6-pentafluorophenyl)-methyl]sulfinyl}ethene; (1E)-1-{[(3,4-dichlorophenyl)methyl]sulfinyl}-2-(2,3,4,5,6-pentafluorophenyl)ethene; (1E)-1-{[(4-iodophenyl)methyl]sulfinyl}-2-(2,3,4,5,6-pentafluorophenyl)ethene; (1E)-1-{[(4-fluorophenyl)methyl]sulfinyl}-2-(2-hydroxy-3,5-dinitrophenyl)ethene; (1E)-1-{[(4-bromophenyl)methyl]sulfinyl}-2-(2-hydroxy-3,5-dinitrophenyl)ethene; (1E)-1-{[(4-chlorophenyl)methyl]sulfinyl}-2-(2-hydroxy-3,5-dinitrophenyl)ethene; (1E)-1-{[(2,4-dichlorophenyl)methyl]sulfinyl}-2-(2-hydroxy-3,5-dinitrophenyl)ethene; (1E)-1-{[(4-methoxyphenyl)methyl]sulfinyl}-2-(2,4,6-trimethoxyphenyl)ethene; (1E)-1-{[(4-methoxyphenyl)methyl]sulfinyl}-2-(3-methyl-2,4-dimethoxyphenyl)ethene; (1E)-1-{[(4-methoxyphenyl)methyl]sulfinyl}-2-(3,4,5-trimethoxyphenyl)ethene; (1E)-1-{[(2-nitro-4,5-dimethoxyphenyl)methyl]sulfinyl}-2-(3,4,5-trimethoxyphenyl)ethene; (1E)-1-{[(2-nitro-4,5-dimethoxyphenyl)methyl]sulfinyl}-2-(2,4,6-trimethoxyphenyl)ethene; (1E)-1-{[(2-nitro-4,5-dimethoxyphenyl)methyl]sulfinyl}-2-(3-methyl-2,4-dimethoxyphenyl)ethene; (1E)-1-{[(4-fluorophenyl)methyl]sulfinyl}-2-(2,3,4-trifluorophenyl)ethene; (1E)-1-{[(4-chlorophenyl)methyl]sulfinyl}-2-(2,3,4-trifluorophenyl)ethene; (1E)-1-{[(4-methoxyphenyl)methyl]sulfinyl}-2-(2,6-methoxy-4-hydroxyphenyl)ethene; (1E)-1-{[(4-methoxyphenyl)methyl]sulfinyl}-2-(2,3,5,6-tetrafluorophenyl)ethene; (1E)-1-{[(4-methoxyphenyl)methyl]sulfinyl}-2-(2,4,5-trimethoxyphenyl)ethene; (1E)-1-{[(4-methoxyphenyl)methyl]sulfinyl}-2-(2,3,4-trimethoxyphenyl)ethene; (1E)-1-{[(4-methoxyphenyl)methyl]sulfinyl}-2-(3-nitro-4-hydroxy-5-methoxyphenyl)ethene; (1E)-1-{[(4-methoxyphenyl)methyl]sulfinyl}-2-(3,4-dimethoxy-6-nitrophenyl)ethene; (1E)-1-{[(4-methoxyphenyl)methyl]sulfinyl}-2-(3,4-dimethoxy-5-iodophenyl)ethene; (1E)-1-{[(4-methoxyphenyl)methyl]sulfinyl}-2-(2,6-dimethoxy-4-fluorophenyl)ethene; (1E)-1-{[(4-methoxyphenyl)methyl]sulfinyl}-2-(2-hydroxy-4,6-dimethoxyphenyl)ethene; (1E)-1-{[(4-methoxyphenyl)methyl]sulfinyl}-2-(2,4,6-trimethylphenyl)ethene; (1E)-1-{[(4-chlorophenyl)methyl]sulfinyl}-2-(2,4,6-trimethoxyphenyl)ethene; (1E)-1-{[(4-chlorophenyl)methyl]sulfinyl}-2-(2,6-dimethoxy-4-fluorophenyl)ethene; (1E)-1-{[(4-chlorophenyl)methyl]sulfinyl}-2-(2-hydroxy-4,6-dimethoxyphenyl)ethene; (1E)-1-{[(4-bromophenyl)methyl]sulfinyl}-2-(2,4,6-trimethoxyphenyl)ethene; (1E)-1-{[(4-bromophenyl)methyl]sulfinyl}-2-(2,6-dimethoxy-4-fluorophenyl)ethene; (1E)-1-{[(2,4,6-trimethoxyphenyl)methyl]sulfinyl}-2-(2,4,6-trimethoxy-phenyl)ethene; (1E)-1-{[(2,3,4-trimethoxyphenyl)methyl]sulfinyl}-2-(2,6-dimethoxyphenyl)ethene; (1E)-1-{[(3,4,5- trimethoxyphenyl)methyl]sulfinyl}-2-(2,4,6-trimethoxyphenyl)ethene; (1E)-1-{[(3,4,5-trimethoxyphenyl)methyl]sulfinyl}-2-(2,6-dimethoxyphenyl)ethene; (1E)-1-{[(3,4,5-trimethoxyphenyl)methyl]sulfinyl}-2-(4-fluorophenyl) ethene; (1E)-2-(4-fluorophenyl)-1-({[4-(trifluoromethyl)phenyl]methyl}-sulfinyl)ethene;(1E)-2-(4-chlorophenyl)-1-({[4-(trifluoromethyl)phenyl]methyl}-sulfinyl)ethene; (1E)-2-(4-bromophenyl)-1-({[4-(trifluoromethyl)phenyl]methyl}-sulfinyl)ethene; (1E)-1-{[(2,4-dichlorophenyl)methyl]sulfinyl}-2-(4-fluoro-phenyl)ethene; (1E) -1-{[(2,4-dichlorophenyl)methyl]sulfinyl}-2-(4-chloro-phenyl)ethene; (1E)-1-{[(3,4-dichloro -phenyl)methyl]sulfinyl}-2-(4-fluoro-phenyl)ethene; (1E)-1-{[(3,4-dichlorophenyl)-methyl]sulfinyl}-2-(4-chloro-phenyl)ethene; (1E)-1-{[(3,4-dichlorophenyl)methyl]sulfinyl}-2-(4-bromo-phenyl)ethene; (1E)-2-(4-fluorophenyl)-1-{[(4-nitrophenyl)methyl]sulfinyl}ethene; 4-({[(1E)-2-(4-fluorophenyl)vinyl]sulfinyl}methyl)benzene-carbonitrile; 4-({[(1E)-2-(4-chlorophenyl)vinyl]sulfinyl}methyl)benzene-carbonitrile; 4-({[(1E)-2-(4-bromophenyl)vinyl]-sulfinyl}methyl)benzene-carbonitrile; (1E)-2-(3,4-difluorophenyl)-1-{[(4-chlorophenyl)methyl]-sulfinyl}ethene; (1E)-2-(3-chloro-4-fluorophenyl)-1-{[(4-chlorophenyl)methyl]-sulfinyl}ethene; (1E)-2-(2-chloro-4-fluorophenyl)-1-{[(4-chlorophenyl)methyl]-sulfinyl}ethene; (1E)-2-(2,4-dichlorophenyl)-1-{[(4-chlorophenyl)methyl]-sulfinyl}ethene; (1E)-2-(3,4-dichlorophenyl)-1-{[(4-chlorophenyl)methyl]-sulfinyl}ethene; (1E)-2-(2,3-dichlorophenyl)-1-{[(4-chloro -phenyl)methyl]-sulfinyl}ethene; (1E)-2-(4-fluorophenyl)-1-{[(4-iodophenyl)methyl]-sulfinyl}ethene; (1E)-1-{[(4-fluorophenyl)methyl]-sulfinyl}-2-(4-iodophenyl)ethene; (1E)-1-{[(4-chlorophenyl)methyl]sulfinyl}-2-(4-iodophenyl)ethene; (1E)-1-{[(4-bromophenyl)methyl]sulfinyl}-2-(4-iodophenyl)ethene; (1E)-1-{[(4-bromophenyl)methyl]sulfinyl}-2-(4-chlorophenyl)ethene; (1E)-2-(4-bromophenyl)-1-{[(4-iodophenyl)methyl]sulfinyl}ethene; (1E)-1-{[(4-iodophenyl)methyl]-sulfinyl}-2-(4-nitrophenyl)ethene; (1E)-1-{[(4-iodophenyl)methyl]sulfinyl}-2-(2-nitrophenyl)ethene; (1E)-2-(4-iodophenyl)-1-{[(4-methoxyphenyl)methyl]sulfinyl}ethene; (1E)-1-{[(2,4-dichlorophenyl) -methyl]sulfinyl}-2-(4-iodophenyl)ethene; (1E)-2-(3,4-dichlorophenyl)-1-{[(4-chloro -phenyl)methyl]-sulfinyl}ethene; (1E)-2-(2-nitrophenyl)-1-{[(4-fluorophenyl) -methyl]sulfinyl}ethene;(1E)-2-(3-nitrophenyl)-1-{[(4-fluorophenyl)methyl]sulfinyl}ethene; (1E)-2-(4-nitrophenyl)-1-{[(4-fluorophenyl)methyl]sulfinyl}ethene; (1E)-2-(2-trifluoromethyiphenyl)-1-{[(4-fluorophenyl)methyl]sulfinyl}ethene; (1E)-2-(3-trifluoromethyiphenyl)-1-{[(4-fluorophenyl)methyl]-sulfinyl}ethene; (1E)-2-(4-trifluoromethyiphenyl)-1-{[(4-fluorophenyl)methyl]-sulfinyl}ethene; (1E)-2-(2-trifluoromethyl -4- fluorophenyl)-1-{[(4-fluorophenyl)methyl]-sulfinyl}ethene; (1E)-2-(2-nitrophenyl)-1-{[(4-chlorophenyl)methyl]sulfinylethene; (1E)-2-(3-nitrophenyl)-1-{[(4-chlorophenyl)methyl]-sulfinyl}ethene; (1E)-2-(4-nitrophenyl)-1-{[(4-chlorophenyl)methyl]-sulfinyl}ethene; (1E)-2-(2-trifluoromethyiphenyl)-1-{[(4-chlorophenyl)methyl]-sulfinyl}ethene; (1E)-2-(3-trifluoromethyiphenyl)-1-{[(4-chlorophenyl)methyl]-sulfinyl}ethene; (1E)-2-(4-trifluoromethyiphenyl)-1-{[(4-chlorophenyl)methyl]-sulfinyl}ethene; (1E)-2-(2-trifluoromethyl -4-fluorophenyl)-1-{[(4-chlorophenyl)methyl]sulfinyl}ethene; (1E)-2-(3-methyl-4-fluorophenyl) -1-{[(4-chlorophenyl)methyl]sulfinyl}ethene; (1E)-2-(2-nitrophenyl)-1-{[(2,4-dichloro-phenyl)methyl]sulfinyl}ethene; (1E)-2-(2-trifluoromethyl-4-fluorophenyl)-1-{[(2,4-dichloro -phenyl)methyl]sulfinyl}ethene; (1E)-2-(2-nitrophenyl)-1-{[(4-bromophenyl)methyl]sulfinyl}ethene;(1E)-2-(3-nitrophenyl)-1-{[(4-bromophenyl) -methyl]sulfinyl}ethene; (1E)-2-(4-nitrophenyl)-1-{[(4-bromophenyl)-methyl]sulfinyl}ethene; (1E)-2-(2-trifluoromethylphenyl)-1-{[(4-bromophenyl)methyl]-sulfinyl}ethene; (1E)-2-(3-trifluoromethyiphenyl)-1-{[(4-fluorophenyl)methyl]-sulfinyl}ethene; (1E)-2-(4-trifluoromethyiphenyl)-1-{[(4-bromophenyl)methyl]-sulfinyl}ethene; (1E)-2-(2-nitrophenyl)-1-{[(4-cyanophenyl)methyl]sulfinyl}ethene; (1E)-2-(3-nitrophenyl)-1-{[(4-cyanophenyl)methyl]-sulfinyl}ethene; (1E)-2-(4-nitrophenyl)-1-{[(4-cyanophenyl)methyl]sulfinyl}ethene; (1E)-2-(4-fluorophenyl)-1-{[(4-methylphenyl)methyl]sulfinyl}ethene; (1E)-2-(4-bromophenyl)-1-{[(4-methylphenyl)methyl]sulfinyl}ethene; (1E)-2-(2-nitrophenyl)-1-{[(4-methylphenyl)methyl]sulfinyl}ethene; (1E)-2-(3-nitrophenyl)-1-{[(4-methylphenyl)methyl]sulfinyl}ethene; (1E)-2-(4-nitrophenyl)-1-{[(4-methylphenyl)methyl]sulfinyl}ethene; (1E)-2-(4-fluorophenyl)-1-{[(4-methoxyphenyl)methyl]sulfinyl}ethene; (1E)-2-(4-chlorophenyl)-1-{[(4-methoxyphenyl)methyl]sulfinyl}ethene; (1E)-2-(4-bromophenyl)-1-{[(4-methoxyphenyl)methyl]-sulfinyl}ethene; (1E)-2-(2-nitrophenyl)-1-{[(4-methoxyphenyl)methyl]-sulfinyl}ethene; (1E)-2-(3-nitrophenyl)-1-{[(4-methoxy -phenyl)methyl]sulfinyl}ethene; (1E)-2-(4-nitrophenyl)-1-{[(4-methoxy -phenyl)methyl]sulfinyl}ethene; (1E)-2-(4-chlorophenyl)-1-{[(4-nitro -phenyl)methyl]sulfinyl}ethene; (1E)-2-(4-fluorophenyl)-1-{[(4-nitrophenyl)methyl]-sulfinyl }-ethene; and salts thereof.

(i) First Preferred Sub-embodiment of Compounds According to Formula IC

According to a one preferred sub-embodiment of the compounds according to Formula IC, there is provided a compound wherein:

$R^a$ is selected from the group consisting of chlorine, fluorine and bromine, and is bonded to the para position of the ring to which it is attached;

x is 0 or 1;

$R^b$ is selected from the group consisting of chlorine, fluorine, bromine, methyl and methoxy, and is bonded to the ortho or para position of the ring to which it is bonded; and y is 0, 1, 2 or 3.

Preferably, the configuration of the substituents on the carbon-carbon double bond is E-.

Compounds according to the above preferred sub-embodiment of compounds according to Formula IC include, for example: (1E)-2-(2-chlorophenyl)-1-[benzylsulfinyl]ethene; (1E)-2-(4-chlorophenyl)-1-[benzylsulfinyl]ethene; (1E)-1-{[(4-chlorophenyl)methyl]sulfinyl}-2-(4-fluorophenyl)-ethene; (1E)-2-(4-chlorophenyl)-1-{[(4-chlorophenyl)methyl]sulfinyl}ethene; (1E)-2-(4-fluorophenyl)-1-{[(4-fluorophenyl)methyl]sulfinyl}ethene; (1E)-2-(2,4-difluorophenyl)-1-{[(4-fluorophenyl)methyl]sulfinyl}ethene; (1E)-1-{[(4-bromophenyl)methyl]sulfinyl}-2-(4-fluorophenyl)-ethene; (1E)-2-(4-bromophenyl)-1-{[(4-bromophenyl)methyl]sulfinyl}ethene; (1E)-2-(4-bromophenyl)-1-{[(4-fluorophenyl)methyl]sulfinyl}ethene; and (1E)-1-{[(4-bromophenyl)methyl]sulfinyl}-2-(4-chlorophenyl)ethane.

(ii) Second Preferred Sub-embodiment of Compounds According to Formula IC

According to a second preferred sub-embodiment of the compounds of Formula IC, there is provided a compound wherein:

each of $R^a$ and $R^b$ are independently selected from the group consisting of $(C_1-C_6)$alkyl, $(C_1-C_6)$alkoxy, halogen and nitro, and are bonded to the ortho or para position of the ring to which they are attached; and x and y are independently 0, 1, 2 or 3.

Preferably, for the second preferred sub-embodiment of compounds according to Formula IC, the configuration of the substituents on the carbon-carbon double bond is Z—.

Preferred compounds according to the second preferred sub-embodiment of compounds of Formula IC include, for example: (1Z)-2-phenyl-1-[benzylsulfinyl]ethene; (1Z)-1-{[(4-chlorophenyl)methyl]sulfinyl}-2-phenylethene; (1Z)-1-{[(2-chlorophenyl)methyl]sulfinyl}-2-phenylethene; (1Z)-1-{[(4-fluorophenyl)methyl]-sulfinyl}-2-phenylethene; (1Z)-2-(4-chlorophenyl)-1-[benzylsulfinyl]ethene; (1Z)-2-(4-chlorophenyl)-1-{[(4-chlorophenyl)methyl]-sulfinyl}ethene; (1Z)-2-(4-chlorophenyl)-1-{[(2-chlorophenyl)methyl]sulfinyl}-ethene; (1Z)-2-(4-chlorophenyl)-1-{[(4-fluorophenyl)methyl]sulfinyl}-ethene; (1Z)-2-(4-fluorophenyl)-1-[benzylsulfinyl]ethene; (1Z)-2-(4-fluorophenyl)-1-{[(4-chlorophenyl)methyl]sulfinyl}ethene; (1Z)-2-(4-fluorophenyl)-1-{[(2-chlorophenyl)methyl]-sulfinyl}ethene; (1Z)-2-(4-fluorophenyl)-1-{[(4-fluorophenyl)methyl]sulfinyl}ethene; (1Z)-2-(4-bromophenyl)-1-[benzylsulfinyl]ethene; (1Z)-2-(4-bromophenyl)-1-{[(4-chlorophenyl)methyl]sulfinyl}ethene; (1Z)-2-(4-bromophenyl)-1-{[(2-chlorophenyl)methyl]sulfinyl}ethene; (1Z)-2-(4-bromophenyl)-1-{[(4-fluorophenyl)methyl]sulfinyl}ethene; (1Z)-2-(4-methylphenyl)-1-[benzylsulfinyl]ethene; (1Z)-2-(4-methylphenyl)-1-{[(4-chlorophenyl)methyl]-sulfinyl}ethene; (1Z)-2-(4-methylphenyl)-1-{[(2-chlorophenyl)methyl]-sulfinyl}ethene; (1Z)-2-(4-methylphenyl)-1-{[(4-fluorophenyl)methyl]-sulfinyl}ethene; (1Z)-2-(4-fluorophenyl)-1-{[(4-iodophenyl)methyl]-sulfinyl}ethene; and salts thereof.

B. Second Embodiment of Compounds of Formula IA

According to a Second Embodiment of the compounds of Formula IA, there is provided a compound of Formula ID:

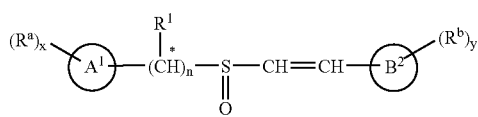

ID wherein $B^2$ is selected from the group consisting of heteroaryl and aryl other than phenyl; or a salt thereof.

Preferably, $B^2$ is selected from the group consisting of furyl, thienyl, pyrrolyl, thiazolyl, pyridyl, thienyl-1-dioxide, anthryl, and naphthyl.

Preferably, for compounds of Formula ID, n is 1.

Preferably, for compounds of Formula ID, $R^1$ is —H

Preferably, for compounds of Formula ID, $R^a$ is independently selected from the group consisting of halogen, ($C_1$-$C_3$) alkoxy, —CN, —NO2, and —CF3.

Preferably, the configuration of the substituents on the carbon-carbon double bond is E-.

Preferred compounds according the second sub-embodiment of compounds of Formula IA include, for example: (1E)-1-{[(4-fluorophenyl)methyl]-sulfinyl}-2-(2-pyridyl)ethene; (1E)-1-{[(4-fluorophenyl)methyl]-sulfinyl}-2-(3-pyridyl)ethene; (1E)-1-{[(4-fluorophenyl)methyl]-sulfinyl}-2-(4-pyridyl)ethene; (1E)-1-{[(4-chlorophenyl)methyl]sulfinyl}-2-(2-pyridyl)ethene; (1E)-1-{[(4-chlorophenyl)methyl]sulfinyl}-2-(3-pyridyl)ethene; (1E)-1-{[(4-chlorophenyl)methyl]-sulfinyl}-2-(4-pyridyl)ethene; (1E)-1-{[(4-bromophenyl)methyl]-sulfinyl}-2-(2-pyridyl)ethene; (1E)-1-{[(4-bromophenyl)methyl]sulfinyl}-2-(3-pyridyl)ethene; (1E)-1-{[(4-bromophenyl)methyl]sulfinyl}-2-(4-pyridyl)ethene; (1E)-1-{[(4-fluorophenyl)methyl]sulfinyl}-2-(2-thienyl)ethene; (1E)-1-{[(4-chlorophenyl)methyl]sulfinyl}-2-(2-thienyl)ethene; (1E)-1-{[4-bromophenyl)methyl]-sulfinyl}-2-(2-thienyl)ethene; (1E)-2-(4-bromo(2-thienyl))-1-{[(4-fluorophenyl)methyl]-sulfinyl}ethene; (1E)-2-(5-bromo(2-thienyl))-1-{[(4-fluorophenyl)methyl]-sulfinyl}ethene; (1E)-2-(5-bromo(2-thienyl))-1-{[(4-chlorophenyl)methyl]-sulfinyl}ethene; (1E)-2-(5-bromo(2-thienyl))-1-{[(4-bromophenyl)methyl]-sulfinyl}ethene; 2-((1E)-2-{[(4-fluoro-phenyl)methyl]-sulfinyl}vinyl)thiole-1,1-dione; 2-((1E)-2-{[(4-chlorophenyl)methyl]-sulfinyl}vinyl)thiole-1,1-dione; 2-((1E)-2-{[(4-bromophenyl)methyl]-sulfinyl}vinyl)thiole-1,1-dione; (1E)-1-{[(4-fluorophenylmethyl]sulfinyl}-2-(3-thienyl)ethene; (1E)-1-{[(4-chlorophenyl)methyl]-sulfinyl}-2-(3-thienyl)ethene; (1E)-1-{[(4-bromophenyl)methyl]-sulfinyl}-2-(3-thienyl)ethene; (1E)-1-{[(4-iodophenyl)methyl]-sulfinyl}-2-(3-thienyl)ethene; (1E)-1-{[(4-methylphenyl)methyl]-sulfinyl}-2-(3-thienyl)ethene; (1E)-1-{[(4-methoxyphenyl)methyl]sulfinyl}-2-(3-thienyl)ethene; (1E)-1-{[(4-trifluoromethylphenylmethyl]sulfinyl}-2-(3-thienyl)-ethene; (1E)-1-{[(2,4-dichlorophenyl)methyl]-sulfinyl}-2-(3-thienyl)-ethene; (1E)-1-{[(3,4-dichlorophenyl)methyl]-sulfinyl}-2-(3-thienyl)ethene; (1E)-1-{[(4-cyanophenyl)methyl]-sulfinyl}-2-(3-thienyl)ethene; (1E)-1-{[(4-nitrophenyl)methyl]-sulfinyl}-2-(3-thienyl)ethene; 3-((1E)-2-{[(4-fluorophenyl)methyl]-sulfinyl}vinyl)thiole-1,1-dione; 3-((1E)-2-{[(4-chlorophenyl)methyl]-sulfinyl}vinyl)thiole-1,1-dione; 3-((1E)-2-{[(4-bromophenyl)methyl]-sulfinyl}vinyl)thiole-1,1-dione; 3-((1E)-2-{[(4-methoxyphenyl)methyl]-sulfinyl}vinyl)thiole-1,1-dione; 3-((1E)-2-{[(2,4-dichlorophenyl)methyl]-sulfinyl}vinyl)thiole-1,1-dione; (1E)-1-{[(4-fluorophenyl)methyl]-sulfinyl}-2-(2-furyl)ethene; (1E)-1-{[(4-chlorophenyl)methyl]-sulfinyl}-2-(2-furyl)ethene; (1E)-1-{[(4-bromophenyl)methyl]-sulfinyl}-2-(2-furyl)ethene; (1E)-1-{[(4-fluorophenyl)methyl]-sulfinyl}-2-(3-furyl)ethene; (1E)-1-{[(4-chlorophenyl)methyl]-sulfinyl}-2-(3-furyl)ethene; (1E)-1-{[(4-bromophenyl)methyl]-sulfinyl}-2-(3-furyl)ethene; (1E)-1-{[(4-iodophenyl)methyl]-sulfinyl}-2-(3-furyl)ethene; (1E)-1-{[(4-methylphenyl)methyl]-sulfinyl}-2-(3-furyl)ethene; (1E)-1-{[(4-methoxyphenyl)methyl]-sulfinyl}-2-(3-furyl)ethene; (1E)-1-{[(4-trifluoromethylphenyl)methyl]-sulfinyl}-2-(3-furyl)ethene; (1E)-1-{[(2,4-dichlorophenyl)methyl]-sulfinyl}-2-(3-furyl)ethene; (1E)-1-{[(3,4-dichlorophenyl)methyl]sulfinyl}-2-(3-furyl)ethene; (1E)-1-{[(4-cyanophenyl)methyl]-sulfinyl}-2-(3-furyl)ethene; (1E)-1-{[(4-nitrophenyl)methyl]-sulfinyl}-2-(3-furyl)ethene; (1E)-1-{[(4-chlorophenyl)methyl]-sulfinyl}-2-(1,3-thiazol-2-yl)ethene; (1E)-1-{[(4-chlorophenyl)methyl]-sulfinyl}-2-pyrrol-2-ylethene; (1E)-1-{[(4-bromophenyl)methyl]-sulfinyl}-2-pyrrol-2-ylethene; (1E)-1-{[(4-chlorophenyl)methyl]sulfinyl}-2-(5-nitro(3-thienyl))ethene; (1E)-1-{[(4-iodophenyl)methyl]-sulfinyl}-2-(5-nitro(3-thienyl))ethene; (1E)-1-{[(2,4-dichlorophenyl)methyl]-sulfinyl}-2-(5-nitro(3-thienyl))ethene; (1E)-1-{[(4-methoxyphenyl)methyl]-sulfinyl}-2-(5-nitro(3-thienyl))ethene; (1E)-1-{[(4-fluorophenyl)methyl]sulfinyl}-2-naphthylethene; (1E)-1-{[(4-fluorophenyl)methyl]-sulfinyl}-2-(2-naphthyl)ethene; (1E)-1-{[(4-chlorophenyl)methyl]-sulfinyl}-2-naphthylethene; (1E)-1-{[(4-chlorophenyl)methyl]-sulfinyl}-2-(2-naphthyl)ethene; (1E)-1-{[(4-bromophenyl)methyl]-sulfinyl}-2-naphthylethene; (1E)-1-{[(4-bromophenyl)methyl]-sulfinyl}-2-(2-naphthyl)ethene; (1E)-2-(9-anthryl)-

1-{[(4-fluorophenyl)methyl]-sulfinyl}-ethene; (1E)-2-(9-anthryl)-1-{[(4-chlorophenyl)methyl]-sulfinyl}ethene; (1E)-2-(9-anthryl)-1-{[(4-bromophenyl)methyl]-sulfinyl}ethene; and salts thereof.

Novel Synthetic Intermediates

The invention is also directed to intermediates, useful in the preparation of compounds of Formula I. Accordingly, there is provided an intermediate compound according to Formula II:

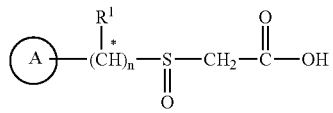

II wherein:

A, n, R¹ and * are as defined herein for compounds of Formula I;

or a salt thereof.

Preferably, for compounds of Formula II, A is other than unsubstituted phenyl.

The Formula II intermediate may be prepared, for example, by reacting an intermediate of Formula IIA:

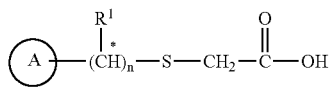

IIA wherein A, n, R¹ and * are as defined herein for compounds of Formula I; or a salt thereof;

with an oxidizing agent capable of oxidizing a sulfide to a sulfoxide; and isolating a compound of Formula II from the reaction products.

The Formula IIA compound may be prepared, for example, by reacting a compound of Formula IIB:

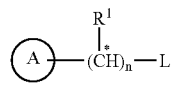

IIB wherein:

L is a leaving group;

with mercaptoacetic acid; and isolating a compound of Formula IIA from the reaction products.

According to another embodiment of the invention, there is provided an intermediate compound according to Formula IV, useful for the preparation of α,β-unsaturated sulfoxides of Formula Iz:

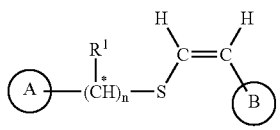

IV wherein A, B, n, R¹ and * are as defined herein for compounds of Formula I, and the configuration of the substituents on the two carbons of the carbon-carbon double bond is E-; or a salt thereof.

Preferably, for compounds of Formula IV, A and B are other than unsubstituted phenyl.

The Formula IV compound may be prepared, for example, by reacting a compound of Formula IVA.

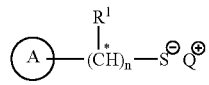

IVA wherein Q⁺ is a counterion preferably selected from the group consisting of alkali metals, alkaline earth metals and transition metals;

with a compound of Formula IVB:

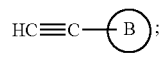

IVB and isolating a compound of Formula IV from the reaction products.

Processes of Preparing Compounds of Formula I

Processes for preparing compounds according to the present invention are provided. According to one such embodiment, a compound of Formula Ie:

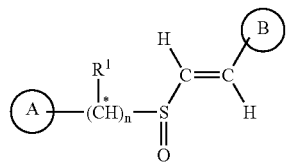

Ie wherein A, B, R¹ and n are as defined herein;

is prepared by reacting a compound of Formula II:

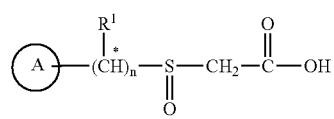

II with a compound of Formula III:

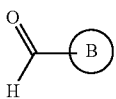

III and isolating a compound of Formula Ie from the reaction products.

According to another such embodiment, a compound of Formula Iz is prepared by reacting a compound of Formula IV:

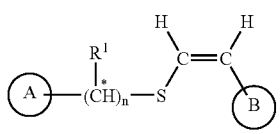

with an oxidizing agent capable of oxidizing a sulfide to a sulfoxide; and isolating a compound of Formula Iz from the reaction products.

Process Wherein a Compound According to Formula I is Employed as a Chemical Intermediate According to another embodiment of the present invention, compounds according to Formula I may be employed as chemical intermediates in the preparation of an α,β-unsaturated sulfones.

According to such an embodiment, a compound according to Formula V:

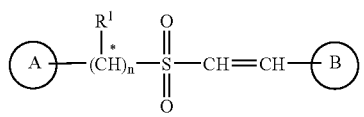

wherein A, B, n, $R^1$, and * are as defined for compounds according to Formula I, and the configuration of the substituents on the carbon-carbon double bond is either E- or Z—, or a salt thereof is prepared by the steps of:

(a) reacting a compound according to Formula I, as defined herein, with at least one oxidizing agent capable of oxidizing a sulfoxide to a sulfone; and (b) isolating a compound according to Formula V from the reaction products.

Pharmaceutical Compositions of Compounds of Formula I

According to another embodiment of the invention, pharmaceutical compositions are provided, comprising a pharmaceutically acceptable carrier and a compound according to Formula I:

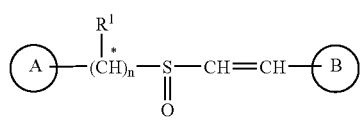

wherein ring A ring B, $R^1$, and * are as described above for Formula I; or a salt of such a compound.

In yet another embodiment of the invention, a conjugate of the Formula I-L-Ab is provided wherein I is a compound of Formula I; Ab is an antibody; and -L- is a single bond or a linking group covalently linking said compound of Formula I to said antibody.

According to sub-embodiments of conjugates thereof, the compound of Formula I, forming the conjugate is a compound of Formula Ie, Iz or IA.

In a preferred sub-embodiment of the aforesaid conjugates, the antibody (Ab) is a monoclonal antibody or a monospecific polygonal antibody.

In more preferred sub-embodiments of the aforesaid conjugates the antibody (Ab) is a tumor-specific antibody.

Pharmaceutical compositions are provided comprising a pharmaceutically acceptable carrier and at least one conjugate according to Formula I-L-Ab.

In yet a further embodiment of the present invention, there is provided a compound of Formula I derivatized as a substrate for a β-lactamase enzyme.

Methods of Treatment

According to another embodiment of the invention, there is provided a method of treating an individual for a proliferative disorder, particularly cancer, comprising administering to the individual an effective amount of at least one compound of Formula I or at least one conjugate of Formula I-L-Ab, alone or in combination with a pharmaceutically acceptable carrier.

According to a further embodiment of the invention, a method of inducing apoptosis of tumor cells in an individual afflicted with cancer is provided, comprising administering to the individual an effective amount of at least one compound of Formula I, or at least one conjugate of Formula I-L-Ab, either alone or in combination with a pharmaceutically acceptable carrier.

According to another embodiment of the invention, a method of inhibiting the growth of tumor cells in an individual afflicted with cancer is provided, comprising administering to the individual an effective amount of at least one compound of Formula I, or at least one conjugate of the Formula I-L-Ab, alone or in combination with a pharmaceutically acceptable carrier.

According to another embodiment of the invention, a method of reducing or eliminating the effects of ionizing radiation on normal calls in an individual who has incurred or is at risk for incurring exposure to ionizing radiation, is provided. This method comprises administering to the individual either prior to, or after the exposure to ionizing radiation, at least one compound of Formula I, alone or in combination with a pharmaceutically acceptable carrier.

According to another embodiment of the invention, there is provided a method of safely increasing the dosage of therapeutic ionizing radiation used in the treatment of cancer or another proliferative disorder, comprising administering an effective amount of at least one radioprotective compound of Formula I, alone or in combination with a pharmaceutically acceptable carrier. This radioprotective compound induces a temporary radioresistant phenotype in the normal tissue of the individual.

According to another embodiment of the invention, there is provided a method for treating an individual who has incurred, or is at risk for incurring, remediable radiation damage from exposure to ionizing radiation. This method comprises administering an effective amount of at least one radioprotective compound of Formula I, alone or in combination with a pharmaceutically acceptable carrier, either prior to, or after the individual incurs remediable radiation damage from exposure to ionizing radiation.

According to other embodiments of the invention, there is provided the use of at least one compound according to Formula I, or at least one conjugate according to Formula I-L-Ab, either alone or as a part of a pharmaceutical composition, for preparation of a medicament for:

(a) treating a proliferative disorder in an individual afflicted with a proliferative disorder;

(b) inhibiting the growth of tumor cells in an individual afflicted with cancer;

(c) inducing apoptosis of tumor cells in an individual afflicted with cancer;

(d) treating an individual who has incurred, or is at risk for incurring remediable radiation damage from exposure to ionizing radiation;

(e) reducing or eliminating the effects of ionizing radiation on normal calls in an individual who has incurred or is at risk for incurring exposure to ionizing radiation;

(f) safely increasing the dosage of therapeutic ionizing radiation used in the treatment of cancer or another proliferative disorder; or (g) protecting an individual from cytotoxic side effects of the administration of a cytotoxic agent.

According to another embodiment of the invention, there is provided a method of treating an individual for a proliferative disorder, particularly cancer, comprising:

(1) administering to the individual an effective amount of at least one radioprotective compound of Formula I, or at least one conjugate of Formula I-L-Ab; and (2) administering an effective amount of therapeutic ionizing radiation.

According to another embodiment of the invention, there is provided a method of reducing the number of malignant cells in the bone marrow of an individual, comprising (1) removing a portion of the individual's bone marrow, (2) administering an effective amount of at least one radioprotective compound of Formula I, to the removed bone marrow; and (3) irradiating the removed bone marrow with an effective amount of ionizing radiation.

In one sub-embodiment of the above method of reducing the number of malignant cells in the bone marrow of an individual, the method further comprises the step of replacing the removed bone marrow with the irradiated bone marrow.

According to another embodiment of the invention, there is provided a method for protecting an individual from cytotoxic side effects of the administration of a cytotoxic agent, particularly a mitotic phase cell cycle inhibitor or a topoisomerase inhibitor, comprising administering to the individual, in advance of the administration of the cytotoxic agent, an effective amount of at least one cytoprotective compound of Formula I; wherein the mitotic phase cell cycle inhibitor or topoisomerase inhibitor is not a compound of Formula I.

Mitotic cell phase inhibitors include, but are not limited to vinca alkaloids, e.g., vincristine and vinblastine, particularly vincristine; taxanes, e.g., paclitaxel and analogs of paclitaxel, particularly paclitaxel; naturally occurring macrolides, e.g., rhizoxin, maytansine, ansamitocin P-3, phomopsin A, dolastatin 10 and halichrondin B; colchicine and derivatives of colchicine.

Paclitaxel is an anti-mitotic drug presently used as an initial treatment for ovarian, breast and lung cancer, with moderate success. Vincrisitin is a well-established anti-mitotic drug widely used for the treatment of breast cancer, Hodgkin's lymphoma and childhood cancers.

Topoisomerase inhibitors may be inhibitors of topoisomerase I, topoisomerase II or both. Topoisomerase I inhibitors include, but are not limited to, adriamycin and etoposide. Topoisomerase II inhibitors include, but are not limited to, camptothecin, irinotecan, topotecan and mitoxanthrone.

According to another embodiment of the invention, there is provided a method of treating an individual for a proliferative disorder, particularly cancer, comprising:

(1) administering to the individual an effective amount of at least one cytoprotective compound of Formula I, or at least one conjugate of Formula I-L-Ab;, and (2) administering an effective amount of at least one mitotic cell phase inhibitor or topoisomerase inhibitor after administration of the at least one cytoprotective compound of Formula I, or at least one conjugate of Formula I-L-Ab;.

DETAILED DESCRIPTION OF THE INVENTION

Treatment of Proliferative Disorders

According to the present invention, $\alpha,\beta$-unsaturated sulfoxides and salts thereof are believed to selectively inhibit proliferation of cancer cells, and kill various tumor cell types without killing (or with reduced killing of) normal cells. It is believed that cells are killed at concentrations where normal cells may be temporarily growth-arrested but not killed.

The compounds of the invention may be administered to individuals (mammals, including animals and humans) afflicted with cancer.

The compounds of the invention are believed to inhibit the proliferation of tumor cells and, for some compounds, to induce cell death. Cell death is believed to result from the induction of apoptosis. The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, and lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's lymphoma, non-Hodgkin's lymphoma [malignant lymphoma]and Waldenström's macroglobulinemia;

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds of the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's fibrosis, Dupuytren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies such as diabetic retinopathies and proliferative vitreoretinopathy (PVR)

Other non-cancer proliferative disorders believed treatable by compounds of the invention include pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

Treatment of tumor cells with the α,β-unsaturated sulfoxide compounds of the invention is believed to lead to inhibition of cell proliferation and induction of apoptotic cell death.

Radioprotective Treatment

The compounds of the invention are also believed to protect normal cells and tissues from the effects of acute and chronic exposure to ionizing radiation.

Individuals may be exposed to ionizing radiation when undergoing therapeutic irradiation for the treatment of proliferative disorders. The compounds are believed effective in protecting normal cells during therapeutic irradiation of abnormal tissues. The compounds are also believed useful in protecting normal cells during radiation treatment for leukemia, especially in the purging of malignant cells from autologous bone marrow grafts with ionizing radiation.

According to the invention, therapeutic ionizing radiation may be administered to an individual on any schedule and in any dose consistent with the prescribed course of treatment, as long as the radioprotectant compound of the invention is administered prior to the radiation. The course of treatment differs from individual to individual, and those of ordinary skill in the art can readily determine the appropriate dose and schedule of therapeutic radiation in a given clinical situation.

Chemoprotective Treatment

In addition, the compounds of the present invention are believed to protect normal cells and tissues from the effects of exposure to cytotoxic agents such as for example, mitotic phase cell cycle inhibitors and topoisomerase inhibitors.

Mitotic Phase Cell Cycle Inhibitors

The usual description of the cell cycle describes the cycle in terms of a series of phases-interphase and M (mitotic) phase—and the subdivision of interphase into the times when DNA synthesis is proceeding, known as the S-phase (for synthesis phase), and the gaps that separate the S-phase from mitosis. G1is the gap after mitosis but before DNA synthesis starts, and G2 is the gap after DNA synthesis is complete before mitosis and cell division. Interphase is thus composed of successive G1, S and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

A mitotic phase cell cycle inhibitor is a chemical agent whose mechanism of action includes inhibition of a cell's passage through any portion of the mitotic (M) phase of the cell cycle. Such agents include, by way of example and not limitation, taxanes, such as paclitaxel and its analogs; vinca alkaloids such as vincristine and vinblastine; colchicine; estramustine; and naturally occurring macrolides such as rhizoxin, maytansine, ansamitocin P-3, phomopsin A, dolastatin 10 and halichrondin B.

Paclitaxel is an anti-mitotic drug presently used as an initial treatment for ovarian, breast and lung cancer, with moderate success. Vincristine is a well-established anti-mitotic drug widely used for the treatment of breast cancer, Hodgkin's lymphoma and childhood cancers.

Topoisomerase Inhibitors

A topoisomerase inhibitor is a chemical agent whose mechanism of action includes interfering with the function of a topoisomerase.

The topoisomerases constitute a group of enzymes that catalyze the conversion of DNA from one topological form to another by introducing transient breaks in one or both strands of a DNA duplex. Topological isomers are molecules that differ only in their state of supercoiling. Topoisomerases serve to relieve torsional stress during replication and transcription. They alter the DNA structure, but not the sequence.

Three different types of topoisomerases have been reported in humans. They are topoisomerase I (91 kDa monomer), and topoisomerase II, which is further subclassified as IIα (170 kDa dimer), and IIβ (180 kDa dimer). The three different types are encoded by genes on three separate chromosomes. Simpler organisms possess only topoisomerase I; however, higher organisms have all three types of topoisomerases. While topoisomerase IIα is present in all eukaryotes, IIβ is present only in vertebrates and appears to be more closely associated with cell differentiation than proliferation. Topoisomerase IIβ appears to be highly homologous to the type IIα.

Topoisomerases act by catalyzing the breakdown and rejoining reactions in the phosphodiester backbone of the DNA molecules. Topoisomerase I reversibly cleaves a single strand in duplex DNA molecule, whereas topoisomerase II breaks and rejoins both DNA strands. These reactions are believed to proceed via transient reaction intermediates, known as "cleavable complexes," where the enzymes (or enzyme subunits) form covalent bonds involving a tyrosine and the cleaved phosphodiester bond of the DNA substrate backbone.

Topoisomerases have become important chemotherapeutic targets for cancer treatment. Camptothecin and its derivatives are reported to act specifically at the level of the topoisomerase I—DNA complex and stimulate DNA cleavage. Agents, such as β-lapachone, act by blocking the formation of the topoisomerase I—DNA complex. Several novel compounds have been developed that can target either topoisomerase I or topoisomerase IIa-/IIβ-isoforms, or all three types of topoisomerases. Inhibition of topoisomerase II is considered to be more challenging due to the complexity of interactions. Most inhibitors of topoisomerase II block the ligation step, leading to stabilized "cleavable complexes" between DNA and the enzyme. Most enzyme inhibitors function by docking into the enzyme active site or nearby allosteric site to block the reaction of the normal substrate. Inhibition of the topoisomerase II involves two parts: the aromatic part of the inhibitor molecule intercalates between DNA base pairs and another more polar portion interacts with topoisomerase. Because topoisomerase II inhibitors (e.g., doxorubicin, and etoposide) act as poisons rather than as classical competitive inhibitors, their action is dependent upon the level of the enzyme in cells. Rapidly proliferating cells, which contain relatively higher levels of topoisomerase II, appear to be more sensitive to these agents. On the other hand, differentiated cells have relatively low topoisomerase II levels and are much more resistant to the action of these inhibitors.

Inhibitors of topoisomerase I include, for example, adriamycin, etoposide, β-lapachone (Calbiochem No. 428022), AG-555 (Calbiochem No. 112270), 10-hydroxycamptothecin (Calbiochem No. 390238), AG-1387 (Calbiochem No. 658520), rebeccamycin (Calbiochem No. 553700), nogalamycin (Calbiochem No. 488200), and topotecan (Calbiochem No. 614800).

Inhibitors of topoisomerase II include, for example, camptothecin, irinotecan and topotecan, amsacrine (Calbiochem No. 171350), aurintricarboxylic acid (Calbiochem No. 189400), bruneomycin (Calbiochem No. 571120), ellipticine (Calbiochem No. 324688), epirubicin (Calbiochem No. 324905), etoposide (Calbiochem No. 341205), genistein (Calbiochem No. 345834), and merbarone (Calbiochem No. 445800).

Inhibitors of topoisomerase I and II include, for example, aclarubicin (Calbiochem No. 112270), congocidine (Calbiochem No. 480676), daunomycin (Calbiochem No. 251800), ellagic acid (Calbiochem No. 324683), and suramin (Calbiochem No. 574625).

α,β-Unsaturated Sulfoxides of the Invention

The compounds of the present invention differ from other known cytoprotective agents in that they are believed to not only protect normal cells, but also to be operationally cytotoxic in tumor cells. In normal cells, the cytoprotective compounds of the invention are believed to induce a reversible resting state rendering the normal cells relatively refractory to the cytotoxic effect of mitotic phase cell cycle inhibitors and topoisomerase inhibitors.

In addition, without wishing to be bound by any theory, the sulfoxides of the present invention may be metabolized to active metabolites, such metabolism including, but not limited to, oxidation of the sulfoxide moiety to a sulfone. The biological activity of α,β-unsaturated sulfones including antiproliferative activity, radioprotection activity and chemoprotectant activity is described in U.S. Pat. Nos. 6,201,154, 6,359,013, 6,414,034, 6,486,210, 6,541,475, 6,548,553, 6,576,675, 6,599,932, and PCT publications: WO 02069892A3, WO 03064616A2, WO 03072062A2 and WO 03072063A2, the entire contents of which are incorporated herein by reference.

The ring systems A and B of the compounds of the invention are optionally substituted. Any degree of substitution is possible on the ring systems A and B of Formula I. The aryl and heteroaryl rings A and B are preferably mono-, di- or tri substituted, but may be fully substituted, i.e., wherein every ring hydrogen atom on A and B is replaced with a substituent.

The pattern of substitution for ring hydrogens of A and B of Formula I may comprise any pattern of substitution. For example, on a phenyl A or B ring, tri-substitution may comprise substitution at positions 2, 3 and 4, positions 2, 4 and 5, positions 3, 4 and 5, positions 2, 5 an 6 or positions 2, 4 and 6. Likewise, the pattern of tetra-substitution of a phenyl A or B ring may comprise, for example, substitution at positions 2, 3, 4 and 5, positions 2, 4, 5 and 6, or positions 2, 3, 5 and 6. Di-substitution of a phenyl A or B ring may comprise substitution, for example, at the 2 and 3 positions, the 2 and 4 positions, the 2 and 5 positions, the 2 and 6, positions, the 3 and 4 positions, the 3 and 5 positions, or the 3 and 6 positions.

The pattern of substitution on a five-membered heteroaryl A or B ring must also account for the number of heteroatoms contained in the heteroaromatic ring and point of attachment of the heteroaryl ring. Substitution on a five membered heteroaromatic ring containing one heteroatom, wherein the heteroaryl ring is bonded via its two position serves to exemplify the variety of substitution patterns. Substitution on the aforesaid five-membered heteroaryl ring may be, for example, at the 3, 4 or 5 position for mono-substitution; and at the 3 and 4, the 3 and 5, or the 4 and 5 positions for di-substitution.

Where a phenyl A or B ring is mono-substituted the substituent is preferably located at the ortho- or para-position. Where a phenyl A or B ring is di-substituted, the substituents are preferably located at the ortho- and para-positions, or the meta- and para-positions.

According to certain preferred embodiments, the meta- and para-position of the aryl or heteroaryl A ring of Formula I is substituted. Preferably, the para substituent is halogen or $(C_1-C_6)$alkoxy, and the meta substituent is amino, alkyl amino, acyl amino or sulfonyl amino in these embodiments Besides the terms "para-", "meta-" and "ortho-", substitution positions on a ring may be denoted by a numbering system. However numbering systems are often not consistent between different ring systems. In six-membered aromatic systems, the spatial arrangements are specified as described above by the common nomenclature "para" for 1,4-substitution, "meta" for 1,3-substitution and "ortho" for 1,2-substitution as shown below in Scheme 3.

Scheme 3

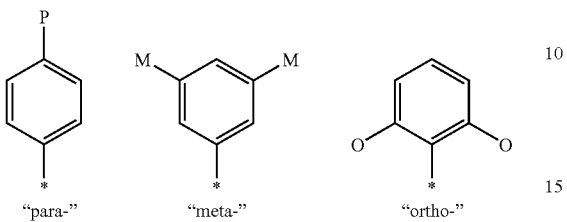

"para-"     "meta-"     "ortho-"

Since aromatic rings are essentially planar, these designations essentially define geometric positions on a six-membered ring that could be communicated geometrically, i.e., the ortho substituent forms a planar angle of 60° with a reference substituent to which it is referred to as being ortho. Likewise, a meta substituent defines a 120° planar angle and a para substituent defines a 180° angle.

To designate substituent patterns in a general way for any planar ring system, the ortho-meta-para nomenclature is only descriptive for six-membered monocycles, i.e., there is no "para" substituent on a five-membered aromatic ring or a bicyclic ring. However, definition of a planar angle or a range of planar angles between two substituents is a convention which readily communicates a particular substitution pattern that is independent of the nature of the particular ring involved. Thus, a para substituent in a six-membered aromatic ring is closely approximated in other planar mono- or bicyclic rings by any substituent which, with the reference substituent, forms a planar angle of between about 144° and about 180°. Likewise, a meta substituent in a six-membered aromatic ring is approximated in other planar mono- or bicyclic rings by any substituent which, with the reference substituent, forms a planar angle of between about 90° and about 144°. Several examples of substituent patterns which could be communicated in this way are depicted in Scheme 4.

Scheme 4

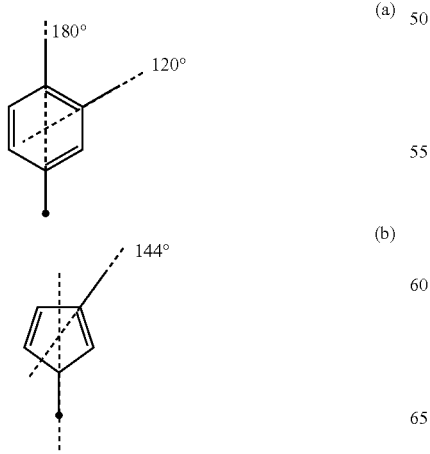

(a)

(b)

-continued

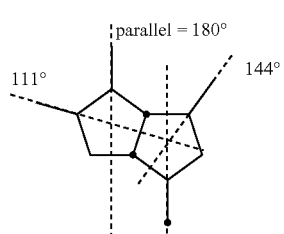

(c)

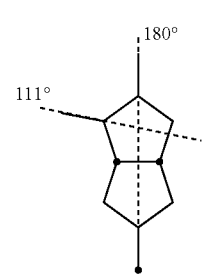

(d)

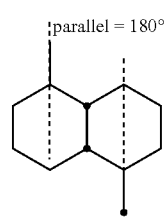

(e)

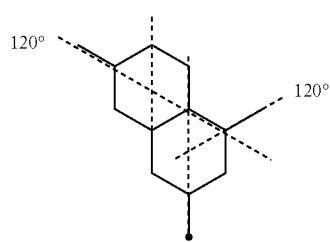

(f)

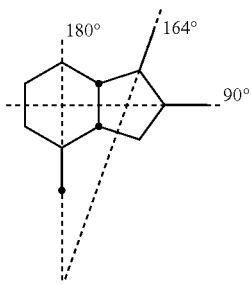

(g)

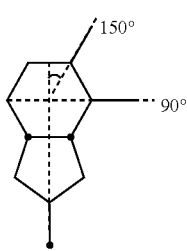

(h)

In some instances, a true angle is not formed between a substituent and a reference substituent. One example of this is a naphthalene system substituted at the 1- and 5-positions as shown in the (e) structure above. In the (e) structure there is no geometric intersection between the lines defined by the 1- and 5-position bonds. However, it is reasonable to regard these "parallel" bonds as defining a 180° angle and thus approximating the para-arrangement of a six-membered planar ring.

Preparation of Compounds of the Invention

α,β-unsaturated sulfoxides of Formula I may be prepared via synthetic organic chemistry methods within the capability of a chemist of ordinary skill. Compounds of Formula Ie and of Formula Iz are preferably prepared via procedures that are selective for the preparation of (E)- or (Z)-olefins respectively.

Preparation of (E)-Compounds of the Invention

One preferred preparation of the (E)-α,β-unsaturated sulfoxides of Formula Ie is by a Knoevenagel condensation of B-aldehydes (iv) with A-(CHR$^1$)$_n$-sulfinyl acetic acids (iii), according to the Scheme 5 below, wherein A, B, n and R$^1$ are defined as for Formula I, above.

(DMSO), tetraglyme, N-methylpyrrolidinone (NMP) or hexamethylphosphoramide (HMPA) at an elevated temperature, preferably greater than 50° C., more preferably greater than 100° C.

Alternatively, for compounds of formula (ii) in Scheme 5 wherein n is zero, the corresponding aryl or heteroaryl sulfide acetic acid may be prepared by addition of a thioglycollic acid ester, preferably a (C$_1$-C$_6$)alkyl ester, more preferably, a methyl, ethyl or t-butyl ester, to an intermediate of formula (i) wherein n is zero and L is a halogen, preferably chlorine or bromine. The reaction may be catalyzed by a zero valent palladium or nickel catalyst, preferably an air-stable palladium catalyst, more preferably dihydrogen dichloro-bis-(di-tert-butylphosphinito(P)dipalladate(2-) [391663-95-7]or dihydrogen di-p-chloro-tetrakis-di-tert-butylphosphinito(P) dipalladate(2-) [391708-31-8]. The reaction is done in the presence of a suitable base, preferably sodium-tert-butoxide. The reaction is preferably done in the presence of a suitable solvent, preferably a solvent having a boiling point greater than 50° C., more preferably a solvent selected from the group consisting of toluene, xylene, mesitylene, DMF, NMP, and THF. See, Li et al., *J. Org. Chem.*, 2001, 66, 8677-8681; and

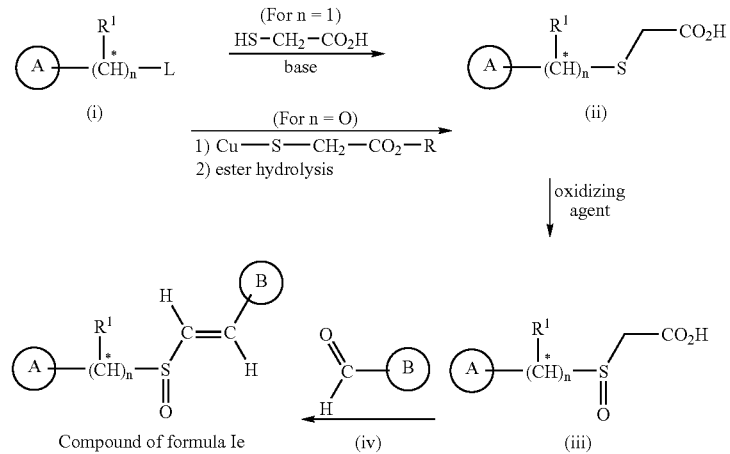

Scheme 5

According to Scheme 5, the A-(CHR$^1$)$_n$-sulfide acetic acid (ii) (for compounds wherein n is 1) is formed by the reaction of suitable salt of thioglycollic acid and a A-(CHR$^1$)$_n$-L compound (i), wherein A, n and R$^1$ are as defined herein and L is a suitable leaving group. Suitable thioglycollate salts include alkali metal salts such as sodium and potassium salts. Suitable leaving groups for (i) include, for example, halogen, tosyl, nosyl, trifyl, or mesyl. The reaction is preferably carried out in a polar solvent, more preferably a (C$_1$-C$_4$) alkyl alcohol, e.g., methanol. The reaction is preferably carried out at higher than ambient temperature, more preferably greater than 50° C., most preferably at the reflux temperature of the solvent.

For compounds of formula (ii) in Scheme 5 wherein n is zero, the corresponding aryl or heteroaryl sulfide acetic acid may be prepared by addition of a copper salt of thioglycollic acid ester, wherein R is an alkyl group, preferably (C$_1$-C$_6$) alkyl, more preferably, methyl, ethyl or t-butyl, to an intermediate of formula (i) wherein n is 1. The reaction is preferably performed in a basic solvent such as, for example pyridine, quinoline or lutidine or a polar aprotic solvent such, for example, dimethyl formamide (DMF), dimethylsulfoxide Li et al., *J. Org. Chem.*, 2002, 67, 3643-3650, the entire disclosures of which are incorporated herein by reference.

The sulfide acetic acid compound (ii) in Scheme 5 may be then oxidized with a suitable oxidizing agent to give a corresponding sulfinyl acetic acid compound (iii). A suitable oxidizing agent is any oxidant capable of selectively oxidizing a sulfide to a sulfoxide. Examples include 3-chloroperbenzoic acid (MCPBA) (Aldrich 27,303-1) and potassium peroxymonosulfate (Aldrich 22,803-6). The oxidation is preferably performed at low temperature, preferably from −40° C. to 0° C. The reaction is preferably carried out in a suitable solvent. Suitable solvents are preferably nonpolar organic solvents, more preferably halogenated solvents, e.g., dichloromethane (DCM).

The sulfide acetic acid compound (ii) in Scheme 5 may be then oxidized with a suitable oxidizing agent to give a corresponding sulfinyl acetic acid compound (iii). A suitable oxidizing agent is any oxidant capable of selectively oxidizing a sulfide to a sulfoxide. Examples include 3-chloroperbenzoic acid (MCPBA) (Aldrich 27,303-1) and potassium peroxymonosulfate (Aldrich 22,803-6) The oxidation is preferably performed at low temperature, preferably from −40° C. to 0° C. The reaction is preferably carried out in a suitable solvent. Suitable solvents are preferably nonpolar organic solvents, more preferably halogenated solvents, e.g., dichloromethane (DCM).

Condensation of (iii) with the B-aldehydes (iv) via a Knoevenagel reaction in the presence of benzylamine and glacial acetic acid yields the desired (E)-α,β-unsaturated sulfoxide of Formula Ie.

The following is a more detailed two-part synthesis procedure for preparing the Formula Ie α,β-unsaturated sulfoxides, (E)-A-CHR$^1$SOCH=CH—B, according to the above Scheme 5 via intermediate sulfonylacetic acid (iii). The following synthesis procedures show syntheses of compounds wherein A and B are both phenyl. However the procedures are exemplary of compounds of Formula I comprising other aryl and heteroaryl A and B rings.

General Procedure 1: Synthesis (E)-α,β Unsaturated Sulfoxides

Step A. Synthesis of Substituted benzylthioacetic acid:

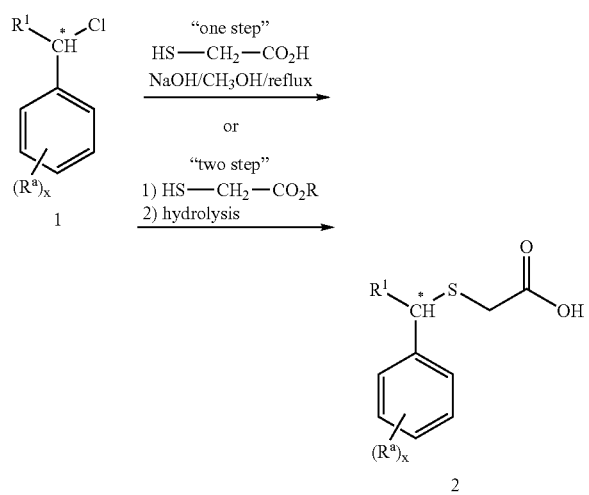

According to Scheme 6, to a cold (0° C.) solution of sodium hydroxide (40 g, 1 mol) in methanol (500 mL), is added thioglycollic acid (46 g, 0.5 mol) slowly over 30 minutes. The precipitated sodium thioglycollate formed thereby is dissolved by stirring and warming the reaction mixture to about 50° C. The solution is then cooled to room temperature. A substituted benzyl chloride 1 (80.5 g, 0.5 mol) is added portionwise in order to attenuate of exothermic nature of the reaction. The resulting reaction mixture is then heated at reflux for 2 hours, then cooled to ambient temperature and poured onto crushed ice (1 Kg) containing concentrated hydrochloric acid (100 mL). A solid white precipitate is formed. The precipitate is filtered, washed with ice cold water and dried under vacuum to yield a benzylthioacetic acid 2.

According to an alternative to step A above, the benzylthioacetic acid intermediates 2 may be generated via the two-step route shown in Scheme 6, by substituting a thioglycollate ester (HS—CH2-CO2R) for thioglycollic acid, wherein R is an alkyl group, typically (C$_1$-C$_6$)alkyl. Reaction of this ester reagent results in the formation of an alkylthioacetate intermediate which may be subsequently hydrolyzed to yield the corresponding benzylthioacetic acid 2.

Step B. Synthesis of Substituted benzylsulfinylacetic acid 3:

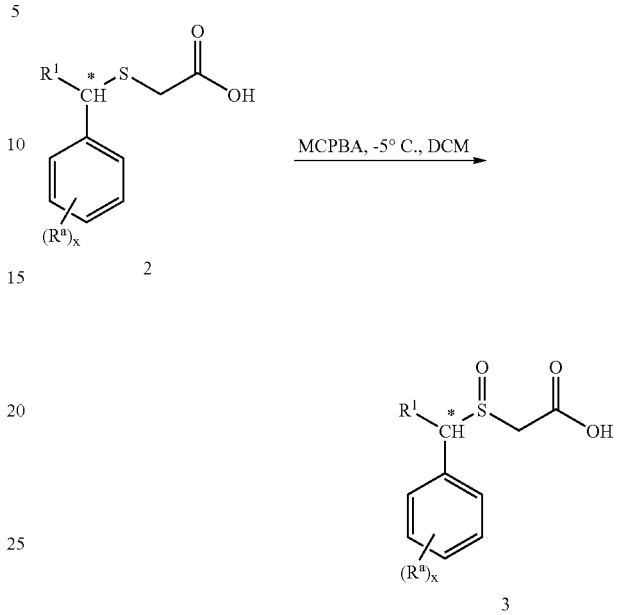

According to Scheme 7, to a cooled solution of a benzylthioacetic acid 2 (10 mmol) in anhydrous dichloromethane (DCM) (15 mL) is added MCPBA (20 mmol, 50% concentration basis, Lancaster). The reaction mixture is stirred at about −5° C. for 6 hours. The precipitated 3-chlorobenzoic acid is removed by filtration. The filtrate is washed with water, dried over magnesium sulfate and concentrated. After removal of the solvent, the substituted benzylsulfinylacetic acid 3 is purified either by crystallization or by silica gel chromatography.

Step C. Synthesis of (E)-Substituted styrylbenzyl sulfoxides 5:

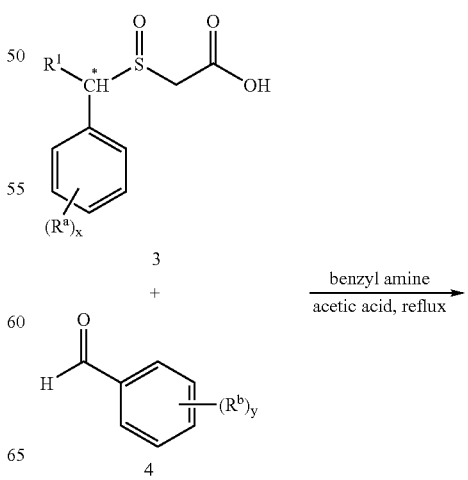

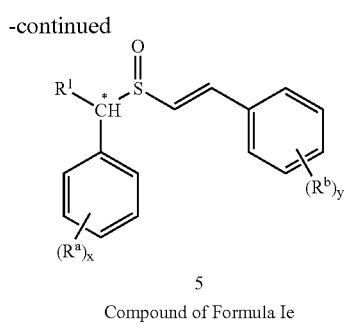

Compound of Formula Ie

According to Scheme 8, a solution of the substituted benzylsulfinylacetic acid 3 (20 mmol) in glacial acetic acid (20 mL) is treated with a substituted benzaldehyde 4 (20 mmol) in the presence of a catalytic amount of benzylamine (0.5 mL). The resulting reaction mixture is heated at reflux for 6 hours and then cooled to ambient temperature. After cooling, ether (100 mL) is added to the reaction mixture. The resulting mixture is washed successively with saturated aqueous sodium hydrogen carbonate (3×30 mL), sodium bisulfite (40 mL), dilute hydrochloric acid (40 mL) and water (60 mL). The ether layer is then dried over anhydrous calcium chloride and concentrated. The resulting solid residue is purified by crystallization or by column chromatography on silica gel to yield an (E)-α,β-unsaturated Sulfoxides of Formula Ie, 5.

Preparation of (Z)-α,β-Unsaturated Sulfoxides of Formula Iz

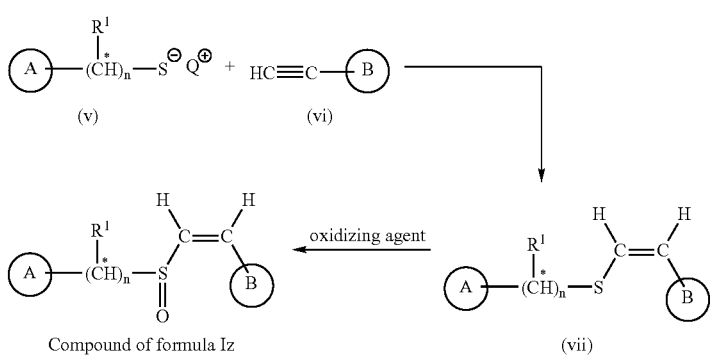

According to Scheme 9, the (Z)-α,β-unsaturated sulfoxides of Formula Iz are preferably prepared by a nucleophilic addition of an appropriate thiol salt (v) to an optionally substituted aryl or heteroarylacetylene (vi), according to the Scheme 9 below. A, B, n and $R^1$ are defined as for Formula I, above, and $Q^+$ is a counterion, preferably an alkali metal, e.g., sodium, lithium or potassium, an alkaline earth metal, e.g., calcium or magnesium, or a transition metal, e.g., zinc or copper. The procedure is analogous to the procedure described by Reddy et al., *Sulfur Letters* 13:83-90 (1991) for the production of (Z)-styryl benzylsulfoxides. The entire disclosure of Reddy et al. is incorporated herein by reference.

The sulfide intermediate (vii) is then oxidized by a suitable oxidizing agent. A suitable oxidizing agent is one capable of oxidizing a sulfide to a sulfoxide of Formula Iz. Suitable oxidizing agents for this reaction are as described above for the oxidation of sulfide acetic acids (ii) to sulfoxide acetic acids (iii) in the preparation of (E)-α,β unsaturated sulfoxides.

The following is a more detailed two-part synthesis for preparing the Formula Iz α,β-unsaturated sulfoxides, (Z)-A-CHR¹SOCH=CH—B. The procedure is illustrated where A and B are both phenyl. However the procedure is applicable to the preparation of compounds of Formula I comprising other aryl and heteroaryl A and B rings.

General Procedure 2: Synthesis (Z)-α,β Unsaturated Sulfoxides

Step A. Preparation of the Intermediate Sulfide

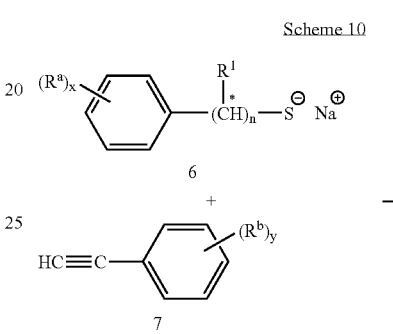

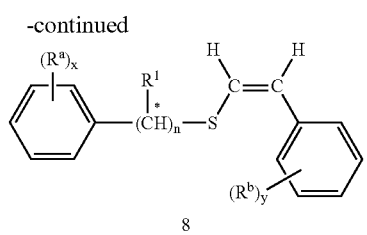

According to Scheme 10, to a refluxing methanolic solution of a substituted or unsubstituted sodium benzylthiolate 6 prepared from 460 mg (0.02 g atom) of (i) sodium, (ii) substituted or unsubstituted benzyl mercaptan (0.02 mol) and (iii) 80 mL of absolute methanol, is added freshly distilled substituted or unsubstituted phenylacetylene 7. The resulting mixture is heated at reflux temperature for 20 hours, then cooled to ambient temperature and poured onto crushed ice. The resulting crude product is filtered, dried and recrystallized from methanol or aqueous methanol to yield a pure (Z)-styryl benzylsulfide 8.

Step B. Oxidation of the sulfide 8 to the Corresponding sulfoxide of Formula Iz

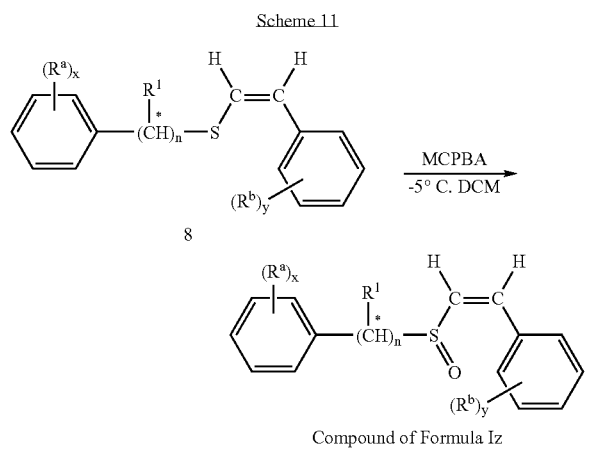

According to Scheme 11, to a cooled solution (−5 to −10° C.) of the (Z)-α,β-unsaturated sulfide 8 (3.0 g) in anhydrous DCM (30 mL) is added MCPBA (20 mmol, 50% concentration basis, Lancaster). The reaction mixture is stirred at −5° C. for 6 hours. The precipitated 3-chlorobenzoic acid is removed by filtration. The filtrate is washed with water, dried over magnesium sulfate and concentrated. After removal of the solvent, the product (Z)-α,β-unsaturated sulfoxide of Formula I is purified either by crystallization or silica gel chromatography.

α,β-Unsaturated Sulfoxides as Intermediates in Preparing α,β-Unsaturated Sulfones Compounds of the invention may be employed as novel intermediates in the synthesis of α,β-unsaturated sulfones as shown in Scheme 12.

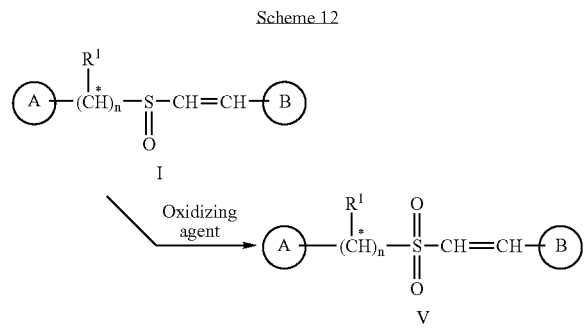

According to Scheme 12, an α,β-unsaturated sulfoxide, according to Formula I may be oxidized to the corresponding sulfone according to Formula V by use of any reagent capable of oxidizing a sulfoxide to a sulfone. Suitable oxidizing reagents include peroxides such as hydrogen peroxide, peracids such as meta-chloroperoxybenzoic acid (MCPBA) or persulfates such as OXONE (potassium peroxymonosulfate). The reaction is preferably carried out in the presence of a suitable solvent. Suitable solvents include, for example, water, acetic acid or non-polar solvents such as dichloromethane (DCM). The reaction may be performed at elevated temperature, for example, from about 30 to about 100° C. with 30% hydrogen peroxide (0.12 mol) in glacial acetic acid (25 mL) by refluxing for 1-2 hours. When the reaction is complete, the reaction mixture may be cooled to ambient temperature and poured onto crushed ice. The product may precipitate and subsequently be collected by filtration and recrystallized from a suitable solvent. Suitable solvents include water and mixtures of water with one or more water-miscible organic solvents such as THF, acetone, methanol, ethanol, isopropanol and acetonitrile.

Derivatization of Compounds of the Invention to Form Conjugates

Preferably, the derivative comprises a carboxylic acid derivative. The carrier may comprise any molecule sufficiently large to be capable of generating an immune response in an appropriate host animal. One such preferred carrier is keyhole limpet haemocyanin (KLH). Additionally, structural components of substituents on the A or B rings of compounds of the invention (e.g., as peptidyl substituents) can potentially provide antigenic activity sufficient to raise antibodies to the styryl sulfones. Antibodies, preferably monoclonal antibodies and monospecific polyclonal antibodies, and most preferably tumor-specific antibodies may be covalently linked to compounds of the present invention.

The covalent linker between a compound of Formula I (or Formulae Ie, Iz or IA) and an antibody may, in its simplest form, comprise a single covalent bond connecting the compound of Formula I to the antibody. More commonly, the compound of Formula I is attached to the antibody using a suitable bifunctional linking reagent. The term "bifunctional linking reagent" refers generally to a molecule that comprises two reactive moieties which are connected by a spacer element. The term "reactive moieties" in this context, refers to chemical functional groups capable of coupling with an antibody or a compound of Formula I by reacting with functional groups on the antibody and the compound of Formula I.

An example of a covalent bond formed as a linker between a compound of Formula I and an antibody is a disulfide bond formed by the oxidation of an antibody and a compound of Formula I, wherein a substituent on A or B of Formula I comprises a peptidyl moiety containing one or more cysteine amino acids. The cysteine residues can be oxidized to form disulfide links by dissolving 1 mg of the a suitable compound of Formula I and 0.5 equivalents of the desired antibody in 1.5 mL of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified by HPLC.

Another example of a suitable covalent bond formed as a linker between a compound of Formula I and an antibody is an amide bond formed by reacting an amino group on a compound of the invention with a carboxylic acid group which forms part of the primary structure of the antibody (Ab) (e.g., for example a glutamic or aspartic amino acid residue). Alternately, an amide bond could be formed if the reacting moieties were reversed, i.e., the compound of Formula I could contain a carboxylic acid functionality and react with an amino functionality within the Ab structure.

Alternatively, a compound of Formula I and an antibody Ab may be covalently linked using a bifunctional linking reagent. In one such embodiment of the present invention, a compound of Formula I, wherein a substituent on A or B of Formula I comprises a peptidyl moiety, is coupled to an antibody using a bifunctional linking reagent.

For example, adducts can be prepared by first preparing S-(-N-hexylsuccinimido)-modified derivatives of an antibody and of a compound of Formula I, according to the method of Cheronis et al., *J. Med. Chem.* 37: 348 (1994) (the entire disclosure of which is incorporated herein by reference). N-hexylmaleimide, a precursor for the modified antibody and compound of Formula I, is prepared from N-(methoxycarbonyl)maleimide and N-hexylamine by mixing the two compounds in saturated $NaHCO_3$ at 0° C. according to the procedure of Bodanszky and Bodanszky, The Practice of Peptide Synthesis; Springer-Verlag, New York, pp. 29-31 (1984) (the entire disclosure of which is incorporated herein by reference). The product of the resulting reaction mixture is isolated by extraction into ethyl acetate, followed by washing with water, dried over $Na_2SO_4$, and is then concentrated in vacuo to produce N-hexylmaleimide as a light yellow oil. S-(N-hexylsuccinimido)-modified antibody and Formula I compound are then prepared from a cysteine-containing peptide and N-hexylmaleimide by mixing one part peptide with 1.5 parts N-hexylmaleimide in DMF (3.3 mL/mM peptide) followed by addition to 30 volumes of 0.1 M ammonium bicarbonate, pH 7.5. The S-alkylation reaction carried out in this manner is complete in 30 min. The resulting S-(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is a Formula I compound wherein a substituent on A or B of Formula I comprises a peptidyl moiety), may be prepared according to the method of Cheronis et al., supra from cysteine-substituted peptides. A mixture of one part bis-maleimidohexane is made with two parts peptide monomer in DMF (3.3 mL/mM peptide) followed by addition to 0.1 ammonium bicarbonate, pH 7.5. The reaction mixture is stirred at room temperature and is usually completed within 30 min. The resulting bis-succinimidohexane peptide dimer is purified by preparative reverse-phase HPLC. After lyophilization the material is a fluffy, white powder.

Covalently linked adducts of the Formula I-L-Ab may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH"). The linking reaction occurs randomly between the Ab and a compound of Formula I having a peptidyl moiety as part of at least on substituent on A or B of Formula I.

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For hetero-bifunctional linking, a compound of Formula I is derivatized with, for example, the N-hydroxysuccinimidyl portion of the bifunctional reagent, and the resulting derivatized compound is purified by chromatography. Next, a suitable tumor-specific Mab is reacted with the second functional group of the bifunctional linking reagent, assuring a directed sequence of binding between components of the desired adduct Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the Mab or the Formula I compound are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either a Mab or to a Formula I compound wherein at least one substituent on A or B comprises a peptidyl moiety, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyridyldithio)-propionate (SPDP), 2-iminothiolane (2-IT), 3-(4-carboxamidophenyldithio)propionthioimidate (CDPT), N-succinimidyl-acetylthioacetate (SATA), ethyl-S-acetyl-propionthioimidate (AMPT) and N-succinimidyl-3-(4-carboxamidophenyldithio)propionate (SCDP). Procedures for preparation of immunoconjugates using these linkers are detailed in Toxin-Targeted Design for Anticancer Therapy. II: Preparation and Biological Comparison of Different Chemically Linked Gelonin-Antibody Conjugates (Cattel, et al, *J. Pharm. Sci.,* 82:7, p699-704, 1993), (the entire disclosure of which is incorporated herein by reference).

According to one embodiment of the invention the antibody comprises a tumor-specific antibody, more preferably a tumor-specific monoclonal antibody or a tumor-specific monospecific polyclonal antibody.

Monoclonal antibodies may be advantageously cleaved by proteolytic enzymes to generate fragments retaining the antigen-binding site. For example, proteolytic treatment of IgG antibodies with papain at neutral pH generates two identical fragments, termed "Fab" fragments, each containing one intact light chain disulfide-bonded to a fragment of the heavy chain (Fd). Each Fab fragment contains one antigen-combining site. The remaining portion of the IgG molecule is a dimer known as "Fc". Similarly, pepsin cleavage at pH 4 results in the fragment, termed a F(ab')2 fragment.

Methods for preparation of such fragments are known to those skilled in the art. See, Goding, Monoclonal Antibodies Principles and Practice, Academic Press (1983), p. 119-123. Fragments of the anti-DBF-MAF monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion.

The effects of sensitization in the therapeutic use of animal origin monoclonal antibodies in the treatment of human disease may be diminished by employing a hybrid molecule generated from the same Fab fragment, but a different Fc fragment, than contained in Mab's previously administered to the same subject. It is contemplated that such hybrid molecules formed from the monoclonal antibodies of the invention may be used in therapy. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci. USA* 81, 6851-6855, 30 1984, both chimeric heavy chain V region exon (VH)-human heavy chain C region genes and chimeric mouse light chain V region exon (V*)-human * light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642-646, 1984. Also see Tan et al., *J. Immunol.* 135, 3564-3567, 1985 for a description of high level expression from a human heavy chain promotor of a human-mouse chimeric * chain after transfection of mouse myeloma cells. As an alternative to combining genomic DNA, cDNA clones of the relevant V and C regions may be combined for production of chimeric antibodies, as described by Whitte et al., *Protein Eng.* 1, 499-505, 1987 and Liu et al., *Proc. Natl. Acad. Sci. USA* 84, 3439-3443, 1987.

For examples of the preparation of chimeric antibodies, see the following U.S. Pat. Nos. 5,292,867; 5,091,313; 5,204, 244; 5,202,238; and 5,169,939. The entire disclosures of these patents, and the publications mentioned in the preceding paragraph, are incorporated herein by reference. Any of these recombinant techniques are available for production of rodent/human chimeric anti-DBP-MAF monoclonal antibodies.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., *Nature* 321, 522-525, 1986; Verhoeyen et al., *Science* 239, 1534-1536, 1988; Reichmann et al., 322, 323-327, 1988; Hale et al., *Lancet* 2, 1394-1399, 1988; Queen et al., *Proc. Natl. Acad. Sci. USA* 86, 10029-10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human antibodies of reduced human immunogenicity. Several such monoclonal antibodies, chimeric animal-human monoclonal antibodies, humanized antibodies and antigen-binding fragments thereof have been made available. Some examples include:

Satumomab Pendetide (by Cytogen, a murine Mab directed against TAG-72); Igovomab (by CIS Bio, a murine Mab fragment Fab2 directed against tumor-associated antigen CA 125); Arcitumomab (by Immunomedics, a murine Mab fragment Fab directed against human carcinoembryonic antigen CEA); Capromab Pentetate (by Cytogen, a murine Mab directed against tumor surface antigen PSMA); Tecnemab KI (by Sorin, murine Mab fragments (Fab/Fab2 mix) directed against HMW-MAA); Nofetumomab (by Boehringer Ingelheim/NeoRx, murine Mab fragments (Fab) directed against carcinoma-associated antigen); Rituximab (by Genentech/IDEC Pharmaceuticals, a chimeric Mab directed against CD20 antigen on the surface of B lymphocytes); Trastuzumab (by Genintech, a humanized antibody directed against human epidermal growth factor receptor 2 (HER 2)); Votumumab (by Organon Teknika, a human Mab directed against cytokeratin tumor-associated antigen); Ontak (by Seragen/Ligand Pharmaceuticals, an IL-2-diphtheria toxin fusion protein that targets cells displaying a surface IL-2 receptor); IMC-C225 (by Imclone, a chimerized monoclonal antibody that binds to EGFR); LCG-Mab (by Cytoclonal Pharmaceutics Monoclonal antibody directed against lung cancer gene LCG) ABX-EGF (by Abgenix, a fully human monoclonal antibody against the epidermal growth factor receptor (EGFr)); and Epratuzumab (by Immunomedics, a humanized, anti-CD22 monoclonal antibody).

Hence, compounds of Formula I can readily be covalently bonded to antibodies, preferably tumor-specific monoclonal antibodies (Nab) via a suitable bifunctional linker (-L-) to yield a conjugate of general Formula, I-L-Ab. In addition, compounds of Formulae Ie, Iz and IA can be covalently bonded to antibodies (Ab), preferably tumor-specific monoclonal antibodies (Mab) via a suitable bifunctional linker (-L-) to yield conjugates of general Formula, Ie-L-Ab, Iz—L-Ab or IA-L-Ab. A general synthetic route for preparing compounds of the present invention of general Formula I-L-Ab is shown in Scheme 13, wherein: ①—NH2 is a compound according to Formula I wherein at least one substituent on the A or B ring is —NH$_2$.

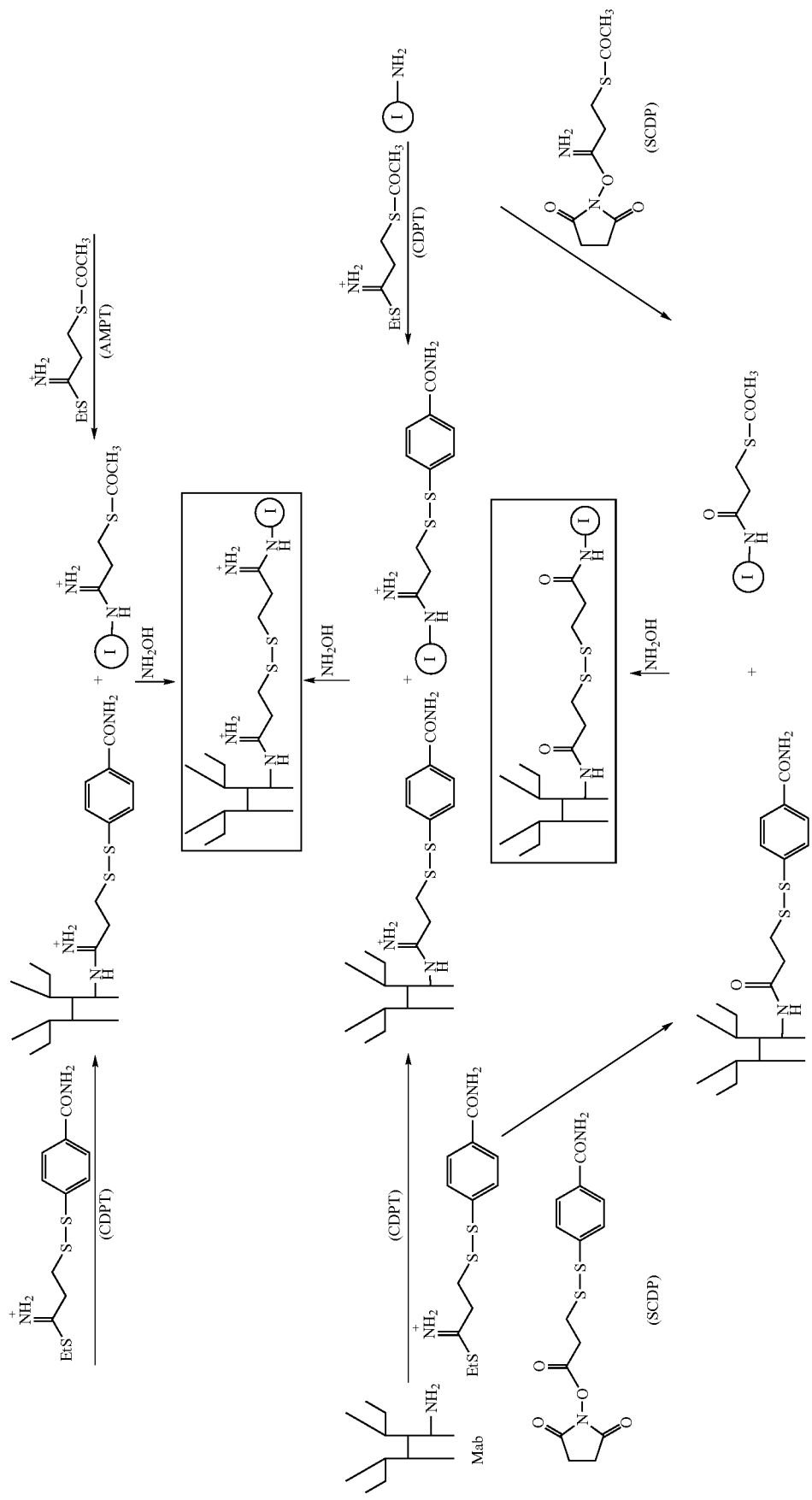

Geometric and Stereo Isomerism in Compounds of the Invention

E-/Z—Isomerism

The α,β-unsaturated sulfoxides of the invention are characterized by isomerism resulting from the presence of an olefinic double bond. This isomerism is commonly referred to as cis-trans isomerism, but the more comprehensive naming convention employs E- and Z—designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus if the four groups on a carbon-carbon double bond are ranked, A being the lowest rank and D being highest, A>B>C>D, the isomers would be named as in Scheme 14.

Scheme 14

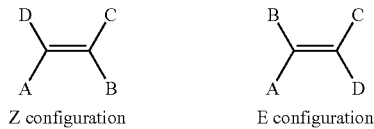

Z configuration    E configuration

Unless otherwise indicated, both configurations, as depicted below in Scheme 15, and mixtures thereof, are included in the scope of "α,β-unsaturated sulfoxides."

Scheme 15

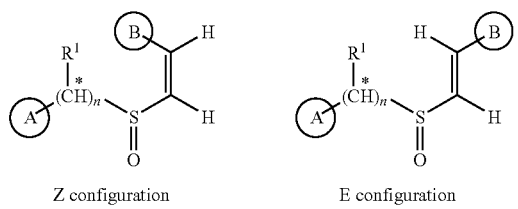

Z configuration    E configuration

B. Optical Isomerism

The present invention is also directed to isolated optical isomers of compounds according to Formula I. The isomers resulting from the presence of a chiral center comprise a pair of nonsuperimposable isomers that are called "enantiomers." Single enantiomers of a pure compound are optically active, i.e., they are capable of rotating the plane of plane polarized light. Single enantiomers are designated according to the Cahn-Ingold-Prelog system. See March, Advanced Organic Chemistry, 4th Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 16, the Cahn-Ingold-Prelog ranking is A>B>C>D. The lowest ranking atom, D is oriented away from the viewer.

Scheme 16

(R) configuration    (S) configuration

Sulfoxides of Formula I have at least one chiral center which is the sulfoxide sulfur atom. In addition compounds of Formula I wherein n is 1 and $R^1$ is other than hydrogen potentially have a second chiral center.

For the sulfoxide chiral center in compounds of the present invention, the lowest priority (an empty orbital) and the highest priority (the sulfoxide oxygen) atoms about the chiral sulfur are fixed. Thus, the absolute configuration of compounds of the invention depends on the priority ranking of the two carbon atoms bonded to the sulfoxide group as shown in Scheme 17.

Scheme 17

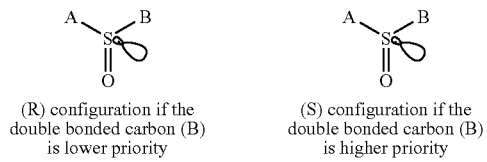

(R) configuration if the         (S) configuration if the
double bonded carbon (B)         double bonded carbon (B)
is lower priority                is higher priority Certain compounds may have more than one chiral center, e.g., n is 1 and $R^1$ is other than —H. If a compound has more than one chiral center, diastereomeric isomerism results, as exemplified in Scheme 18.

Scheme 18

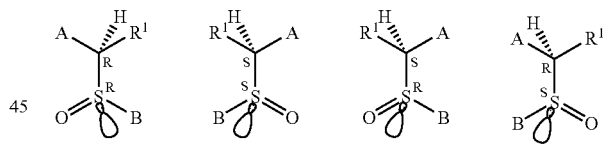

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

By "isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt.% pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

Salts of Compounds of the Invention

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, beta-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. Examples of pharmaceutically unacceptable salts include lithium salts and cyanate salts. All of these salts may be prepared by conventional means from the corresponding α,β-unsaturated sulfoxide by reacting, for example, the appropriate acid or base with the compound of Formula I.

Pharmaceutical Compositions

The sulfoxides of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's fibrosis, Dupuytren's fibrosis, restenosis and cirrhosis.

Administration of Compounds of the Invention

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may be localized in a depot for controlled release to the circulation, or for release to a local site of tumor growth.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. Higher or lower doses are also contemplated.

Radioprotection

The compounds of the invention are further believed useful in the protection of normal cells from the cytotoxic and genetic effects of exposure to radiation, in individuals who have incurred, who will in the future incur and who are at risk for incurring exposure to ionizing radiation.

The specific dose of compound according to the invention to obtain therapeutic benefit for radioprotection will be determined by the particular circumstances of the individual patient including, the size, weight, age and sex of the patient, the type, dose and timing of the ionizing radiation, and the route of administration of the compound of the invention.

For example, a daily dosage of from about 0.05 to about 50 mg/kg/day may be utilized. Higher or lower doses are also contemplated.

Exposure to radiation by an individual may comprise therapeutic radiation administered to the individual or in some indications, to bone marrow removed from the individual.

An individual may also be exposed to ionizing radiation from occupational or environmental sources, as discussed in the background section.

For purposes of the invention, the source of the radiation is not as important as the type (i.e., acute or chronic) and dose level absorbed by the individual. It is understood that the following discussion encompasses ionizing radiation exposures from both occupational and environmental sources.

Individuals suffering from effects of acute or chronic exposure to ionizing radiation that are not immediately fatal are said to have remediable radiation damage. Such remediable radiation damage can be reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

Radioprotection: Therapeutic Ionizing Radiation

For radioprotective administration to individuals receiving therapeutic ionizing radiation, the compounds of the invention should be administered far enough in advance of the therapeutic radiation such that the compound is able to reach the normal cells of the individual in sufficient concentration to exert a radioprotective effect on the normal cells. The pharmacokinetics of specific compounds may be determined by means known in the art and tissue levels of a compound in a particular individual may be determined by conventional analyses.

The compound may be administered as much as about 24 hours, preferably no more than about 18 hours, prior to administration of the radiation. In one embodiment, the therapy is administered at least about 3-12 hours before administration of the therapeutic radiation. Most preferably, the compound is administered once at about 18 hours and again at about 6 hours before the radiation exposure.

One or more $\alpha,\beta$-unsaturated sulfoxides may be administered simultaneously, or different $\alpha,\beta$-unsaturated sulfoxides may be administered at different times during the treatment.

Where the therapeutic radiation is administered in serial fashion, it is preferable to intercalate the administration of one or more radioprotective compounds within the schedule of radiation treatments. As above, different radioprotective compounds of the invention may be administered either simultaneously or at different times during the treatment. Preferably, an about 24-hour period separates administration of the radioprotective compound and the therapeutic radiation. More preferably, the administration of the radioprotective compound and the therapeutic radiation is separated by about 6 to 18 hours. This strategy will yield significant reduction of radiation-induced side effects without affecting the anticancer activity of the therapeutic radiation.

For example, therapeutic radiation at a dose of 0.1 Gy may be given daily for five consecutive days, with a two-day rest, for a total period of 6-8 weeks. One or more $\alpha,\beta$-unsaturated sulfoxides may be administered to the individual 18 hours previous to each round of radiation. It should be pointed out, however, that more aggressive treatment schedules, i.e., delivery of a higher dosage, is contemplated according to the present invention due to the protection of the normal cells afforded by the radioprotective compounds. Thus, the radioprotective effect of the compound increases the therapeutic index of the therapeutic radiation, and may permit the physician to safely increase the dosage of therapeutic radiation above presently recommended levels without risking increased damage to the surrounding normal cells and tissues.

Radioprotection: Radiation-treated Bone Marrow

The radioprotective compounds of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL).

CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The individual who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other individuals suffer from metastatic tumors, and require treatment with total body irradiation (TBI). Because TBI will also kill the individual's hematopoietic cells, a portion of the individual's bone marrow is removed prior to irradiation for subsequent reimplantation. However, metastatic tumor cells are likely present in the bone marrow, and reimplantation often results in a relapse of the cancer within a short time.

Individuals presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the individual is treated with radiation or some other anti-cancer therapy before the autologous purged bone marrow is reimplanted.

Thus, the invention provides a method of reducing the number of malignant cells in bone marrow, comprising the steps of removing a portion of the individual's bone marrow, administering an effective amount of at least one radioprotective compound according to the present invention and irradiating the treated bone marrow with a sufficient dose of ionizing radiation such that malignant cells in the bone marrow are killed. As used herein, "malignant cell" means any uncontrollably proliferating cell, such a tumor cell or neoplastic cell. The radioprotective compounds protect the normal hematopoietic cells present in the bone marrow from the deleterious effects of the ionizing radiation. The compounds also exhibit a direct killing effect on the malignant cells. The number of malignant cells in the bone marrow is significantly reduced prior to reimplantation, thus minimizing the occurrence of a relapse.

Preferably, each α,β-unsaturated sulfoxide is administered to the bone marrow in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar. Higher or lower concentrations may also be used.

The radioprotective compounds may be added directly to the harvested bone marrow, but are preferably dissolved in an organic solvent such as dimethylsulfoxide (DMSO). Pharmaceutical compositions of α,β-unsaturated sulfoxides such as are described in more detail below may also be used.

Preferably, the radioprotective compound is added to the harvested bone marrow about 20 hours prior to radiation exposure, preferably no more than about 24 hours prior to radiation exposure. In one embodiment, the radioprotective compound is administered to the harvested bone marrow at least about 6 hours before radiation exposure. One or more compounds may be administered simultaneously, or different compounds may be administered at different times. Other dosage regimens are also contemplated.

If the individual is to be treated with ionizing radiation prior to reimplantation of the purged bone marrow, the individual may be treated with one or more radioprotective compounds prior to receiving the ionizing radiation dose, as described above.

Radioprotection: Environmental or Occupational Radiation Exposure

The invention also provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective compound. The compound is preferably administered in as short a time as possible following radiation exposure, for example between 0-6 hours following exposure.

Remediable radiation damage may take the form of cytotoxic and genotoxic (i.e., adverse genetic) effects in the individual. In another embodiment, there is therefore provided a method of reducing or eliminating the cytotoxic and genotoxic effects of radiation exposure on normal cells and tissues, comprising administering an effective amount of at least one radioprotective compound prior to acute or chronic radiation exposure. The compound may be administered, for example about 24 hours prior to radiation exposure, preferably no more than about 18 hours prior to radiation exposure. In one embodiment, the compound is administered at least about 6 hours before radiation exposure. Most preferably, the compound is administered at about 18 and again at about 6 hours before the radiation exposure. One or more radioprotective compounds may be administered simultaneously, or different radioprotective compounds may be administered at different times.

When multiple acute exposures are anticipated, the radioprotective compounds of the invention may be administered multiple times. For example, if fire or rescue personnel must enter contaminated areas multiple times, radioprotective compounds of the invention may be administered prior to each exposure. Preferably, an about 24-hour period separates administration of the compound and the radiation exposure. More preferably, the administration of radioprotective compounds and the radiation exposure is separated by about 6 to 18 hours. It is also contemplated that a worker in a nuclear power plant may be administered an effective amount of a radioprotective compound of the invention prior to beginning each shift, to reduce or eliminate the effects of exposure to ionizing radiation.

If an individual is anticipating chronic exposure to ionizing radiation, the radioprotective compound may be administered periodically throughout the duration of anticipated exposure. For example, a nuclear power plant worker or a soldier operating in a forward area contaminated with radioactive fallout may be given the radioprotective compound every 24 hours, preferably every 6-18 hours, in order to mitigate the effects of radiation damage. Likewise, the radioprotective compound may be periodically administered to civilians living in areas contaminated by radioactive fallout until the area is decontaminated or the civilians are removed to a safer environment.

Chemoprotection

The compounds of the invention are believed useful in protecting individuals from the cytotoxic side effects of chemotherapeutic agents, particularly mitotic phase cell cycle inhibitors and topoisomerase inhibitors, used in the treatment of cancer and other proliferative disorders.

The specific dose of a compound according to the invention to obtain therapeutic benefit for chemoprotection will be determined by the particular circumstances of the individual patient including, the size, weight, age and sex of the patient, the type and dose of the administered chemotherapy, the nature and stage and cell damage, and the route of administration of the compound of the invention.

For example, a daily dosage of from about 0.05 to about 50 mg/kg/day may be utilized. Higher or lower doses are also contemplated.

For providing cytoprotection from cytotoxic effects of chemotherapeutic agents, the schedule of administration of the cytotoxic drug, i.e., mitotic phase cell cycle inhibitor or topoisomerase inhibitor, can be any schedule with the stipulation that the α,β-unsaturated sulfoxide is administered prior to the cytotoxic drug. The cytoprotective compound should be administered far enough in advance of the cytotoxic drug such that the former is able to reach the normal cells of the patient in sufficient concentration to exert a cytoprotective effect on the normal cells. Again, individual drug pharmacokinetics and blood levels of a specific drug in a specific patient are factors that may be determined by methods known in the art.

The cytoprotective compound is administered at least about 1 hour, preferably, at least about 2 hours, and more preferably, at least about 4 hours, before administration of the cytotoxic drug. The compound may be administered as much as about 48 hours, preferably no more than about 36 hours, prior to administration of the cytotoxic drug. Most preferably, the compound is administered about 24 hours before the cytotoxic drug. The compound may be administered more or less than 24 hours before the cytotoxic effect, but the protective effect of the compounds is greatest when administered about 24 hours before the cytotoxic drug. One or more cytotoxic drugs may be administered. Similarly, one or more of the α,β-unsaturated sulfoxides may be combined.

Where the cytotoxic drug or drugs is administered in serial fashion, it may prove practical to intercalate cytoprotective compounds of the invention within the schedule with the caveat that a 448 hour period, preferably a 12-36 hour period, most preferably a 24 hour period, separates administration of the two drug types. This strategy will yield partial to complete eradication of cytotoxic drug side effects without affecting anticancer activity.

For example, the mitotic inhibitor may be given daily, or every fourth day, or every twenty-first day. The α,β-unsaturated sulfoxide may be given 24 hours previous to each round of inhibitor administration, both as a cytoprotective agent and as an antitumor agent.

The practice of the invention is illustrated by the following non-limiting examples. In each of the following examples, the sulfinyl acetic acid compound A-$CH_2$—SO—$CH_2$—COOH is made according to Part A of General Procedure 1: Synthesis of (E)-α,β Unsaturated Sulfoxides, above. The (Z)-sulfide intermediates are made according to Part A of General Procedure 2: Synthesis of (Z)-α,β Unsaturated Sulfoxides, above. The final (E)- and (Z)-sulfoxide compounds A-$(CHR^1)_n$—SO—CH=CH—B are recrystallized from 2-propanol and the purity is ascertained by HPLC.

EXAMPLES 1-14

Synthesis of (E) Compounds of the Invention

A solution of a sulfinyl acetic acid X (10 mmol) and a carboxaldehyde Y (10 mmol) from Table 4 is subjected to General Procedure 1, Step C. The resulting product is purified by column chromatography on silica gel to yield the reaction product listed in Table 4.

TABLE 4

| Ex. # | Sulfinyl acetic acid X | carboxaldehyde Y | Reaction Product |
|---|---|---|---|
| 1 | 4-fluorobenzyl-sulfinylacetic acid | 2-pyridine-carboxaldehyde | (1E)-1-{[(4-fluorophenyl)-methyl]sulfinyl}-2-(2-pyridyl)-ethene |
| 2 | 4-fluorobenzyl-sulfinylacetic acid | 3-pyridine-carboxaldehyde | (1E)-1-{[(4-fluorophenyl)-methyl]sulfinyl}-2-(3-pyridyl)-ethene |
| 3 | 4-fluorobenzyl-sulfinylacetic acid | 4-pyridine-carboxaldehyde | (1E)-1-{[(4-fluorophenyl)-methyl]sulfinyl}-2-(4-pyridyl)-ethene |
| 4 | 4-chlorobenzyl-sulfinylacetic acid | 2-pyridine-carboxaldehyde | (1E)-1-{[(4-chlorophenyl)-methyl]sulfinyl}-2-(2-pyridyl)-ethene |
| 5 | 4-chlorobenzyl-sulfinylacetic acid | 3-pyridine-carboxaldehyde | (1E)-1-{[(4-chlorophenyl)-methyl]sulfinyl}-2-(3-pyridyl)-ethene |
| 6 | 4-chlorobenzyl-sulfinylacetic acid | 4-pyridine-carboxaldehyde | (1E)-1-{[(4-chlorophenyl)-methyl]sulfinyl}-2-(4-pyridyl)-ethene |
| 7 | 4-bromobenzyl-sulfinylacetic acid | 2-pyridine-carboxaldehyde | (1E)-1-{[(4-bromophenyl)-methyl]sulfinyl}-2-(2-pyridyl)-ethene |
| 8 | 4-bromobenzyl-sulfinylacetic acid | 3-pyridine-carboxaldehyde | (1E)-1-{[(4-bromophenyl)-methyl]sulfinyl}-2-(3-pyridyl)-ethene |
| 9 | 4-bromobenzyl-sulfinylacetic acid | 4-pyridine-carboxaldehyde | (1E)-1-{[(4-bromophenyl)-methyl]sulfinyl}-2-(4-pyridyl)-ethene |
| 10 | 4-fluorobenzyl-sulfinylacetic acid | 2-thiophene-carboxaldehyde | (1E)-1-{[(4-fluorophenyl)-methyl]sulfinyl}-2-(2-thienyl)-ethene |
| 11 | 4-chlorobenzyl-sulfinylacetic acid | 2-thiophene-carboxaldehyde | (1E)-1-{[(4-chlorophenyl)-methyl]sulfinyl}-2-(2-thienyl)-ethene |
| 12 | 4-bromobenzyl-sulfinylacetic acid | 2-thiophene-carboxaldehyde | (1E)-1-{[(4-bromophenyl)-methyl]sulfinyl}-2-(2-thienyl)-ethene |
| 13 | 4-fluorobenzyl-sulfinylacetic acid | 4-bromo-2-thiophene-carboxaldehyde | (1E)-2-(4-bromo(2-thienyl))-1-{[(4-fluorophenyl)methyl]-sulfinyl}ethene; |
| 14 | 4-chlorobenzyl-sulfinylacetic acid | 4-bromo-2-thiophene-carboxaldehyde | (1E)-2-(4-bromo(2-thienyl))-1-{[(4-chlorophenyl)methyl]-sulfinyl}ethene; |

EXAMPLES 15-28

Synthesis of (Z)-Compounds of the Invention

A solution of an aryl or heteroaryl acetylene A and a mercaptan B (provided in Table 5) are subjected to General Procedure 2, Step A, to form sulfide C. Sulfide C is then oxidized according to General Procedure 2, step B, to yield sulfoxide D, which is purified by column chromatography and/or cyrstallization.

TABLE 5

| Ex. # | acetylene A | mercaptan B | sulfide C | sulfoxide D |
|---|---|---|---|---|
| 15 | 4-chlorophenyl-acetylene | 4-chlorobenzyl mercaptan | (1Z)-2-(4-chlorophenyl)-1-[(4-chloro-phenyl)-methylthio]ethene | (1Z)-2-(4-chlorophenyl)-1-{[(4-chlorophenyl)-methyl]sulfinyl}ethene |
| 16 | 4-chlorophenyl-acetylene | 2-chlorobenzyl mercaptan | (1Z)-2-(4-chlorophenyl)-1-[(2-chloro-phenyl)-methylthio]ethene | (1Z)-2-(4-chloro-phenyl)-1-{[(2-chlorophenyl)-methyl]sulfinyl}ethene |
| 17 | 4-chlorophenyl-acetylene | 4-fluorobenzyl mercaptan | (1Z)-2-(4-chlorophenyl)-1-[(2-fluoro-phenyl)-methylthio]ethene | (1Z)-2-(4-chlorophenyl)-1-{[(2-fluorophenyl)-methyl]sulfinyl}ethene |
| 18 | 4-fluorophenyl-acetylene | benzyl mercaptan | (1Z)-2-(4-fluorophenyl)-1-(benzyllthio)ethene | (1Z)-2-(4-fluorophenyl)-1-[benzylsulfinyl]ethene |
| 19 | 4-fluorophenyl-acetylene | 4-chlorobenzyl mercaptan | (1Z)-2-(4-fluorophenyl)-1-[(4-chloro-phenyl)-methylthio]ethene | (1Z)-2-(4-fluorophenyl)-1-{[(4-chlorophenyl)-methyl]sulfinyl}ethene |
| 20 | 4-fluorophenyl-acetylene | 2-chlorobenzyl mercaptan | (1Z)-2-(4-fluorophenyl)-1-[(2-chloro-phenyl-)methylthio]ethene | (1Z)-2-(4-fluorophenyl)-1-{[(2-chlorophenyl)-methyl]sulfinyl}ethene |
| 21 | 4-fluorophenyl-acetylene | 4-fluorobenzyl mercaptan | (1Z)-2-(4-fluorophenyl)-1-[(4-fluoro-phenyl)-methylthio]ethene | (1Z)-2-(4-fluorophenyl)-1-{[(2-fluorophenyl)-methyl]sulfinyl}ethene |
| 22 | 4-bromophenyl-acetylene | benzyl mercaptan | (1Z)-2-(4-bromophenyl)-1-(benzyllthio)-ethene | (1Z)-2-(4-bromophenyl)-1-[benzylsulfinyl]ethene |
| 23 | 4-bromophenyl-acetylene | 4-chlorobenzyl mercaptan | (1Z)-2-(4-bromophenyl)-1-[(4-chlorophenyl)-methylthio]ethene | (1Z)-2-(4-bromophenyl)-1-{[(4-chloro-phenyl)-methyl]sulfinyl}-ethene |
| 24 | 4-bromophenyl-acetylene | 2-chlorobenzyl mercaptan | (1Z)-2-(4-bromophenyl)-1-[(2-chloro-phenyl)-methylthio]ethene | (1Z)-2-(4-bromophenyl)-1-{[(2-chlorophenyl)-methyl]sulfinyl}-ethene |
| 25 | 4-bromophenyl-acetylene | 4-fluorobenzyl mercaptan | (1Z)-2-(4-bromophenyl)-1-[(4-fluoro-phenyl)-methylthio]ethene | (1Z)-2-(4-bromophenyl)-1-{[(4-fluorophenyl)-methyl]sulfinyl}-ethene |
| 26 | 4-methylphenyl-acetylene | benzyl mercaptan | (1Z)-2-(4-methylphenyl)-1-(benzyllthio)-ethene | (1Z)-2-(4-methylphenyl)-1-[benzylsulfinyl]ethene |
| 27 | 4-methylphenyl-acetylene | 4-chlorobenzyl mercaptan | (1Z)-2-(4-methylphenyl)-1-[(4-chloro-phenyl)-methylthio]ethene | (1Z)-2-(4-methylphenyl)-1-{[(4-chloro-phenyl)-methyl]sulfinyl}-ethene |
| 28 | 4-methylphenyl-acetylene | 2-chlorobenzyl mercaptan | (1Z)-2-(4-methylphenyl)-1-[(2-chloro-phenyl)-methylthio]ethene | (1Z)-2-(4-methylphenyl)-1-{[(2-chloro-phenyl)-methyl]sulfinyl}-ethene |

EXAMPLES 29-32

Preparation of Additional (E)-Compounds of the Invention

Further (E)-compounds of the invention are prepared according to Scheme 19. Compounds prepared according to Scheme 19 are listed in Table 6 below.

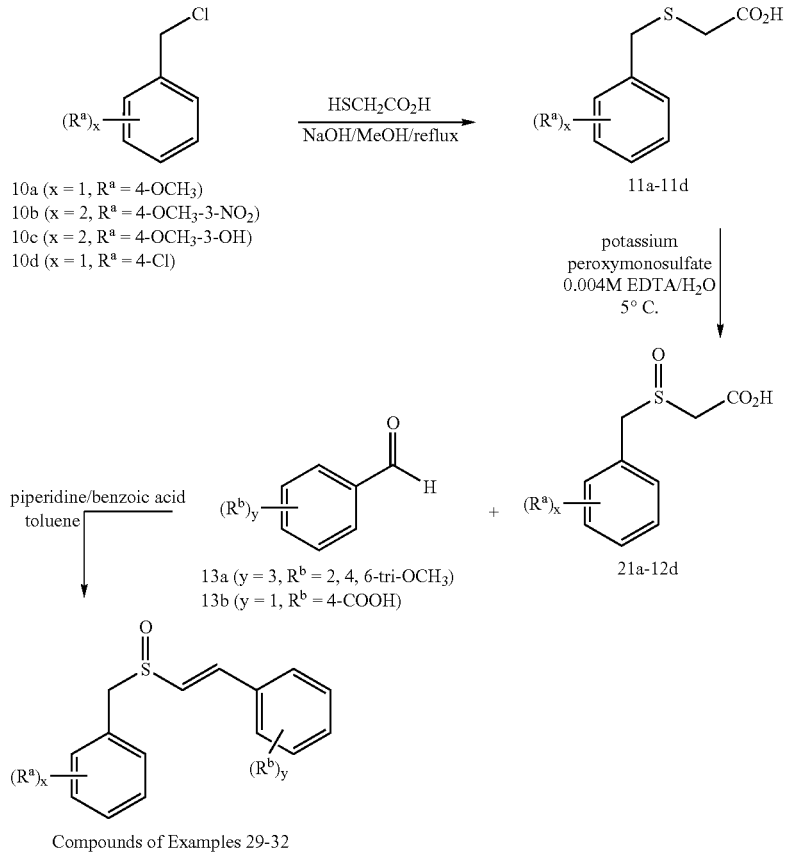

Compounds of Examples 29-32

Step A. General Preparation of Benzylthioacetic acids 11a-d.

To a cold (about 0° C.) solution of sodium hydroxide (40 g, 1mol) in methanol (500 mL) was added thioglycollic acid (46 g, 0.5 mol) slowly over 30 minutes. A solid precipitate of sodium thioglycollate formed. The precipitate was dissolved by stirring and warming the mixture to about 50° C. After dissolution of the precipitated sodium thioglycollate, the resulting solution was cooled to room temperature (25° C.). To the cooled solution was added the substituted benzyl chloride (10a, 10b, 10c or 10d) (0.5 mol) portionwise at a rate wherein the temperature of the resulting mixture was kept below 40° C. during the addition. When the addition of the substituted benzyl chloride was complete, the resulting mixture was warmed to reflux and maintained at reflux temperature for 2 hours. The hot mixture was then cooled to room temperature (25° C.) and poured onto crushed ice (1 Kg) containing hydrochloric acid (12M, 100 mL). A white precipitate formed. The precipitate was filtered, washed with ice cold water (3×100 mL) and dried under vacuum to yield the desired benzylthioacetic acid (11a, 11b, 11c or 11d).

Step B. General Preparation of Benzylsulfinylacetic acids 12a-12d.

To a vigorously stirred solution of sodium hydroxide (3 g, 0.076 mol) in deionized water (150 mL) was added a substituted benzylthioacetic acid (11a, 11b, 11c or 11d) prepared according to Step A (0.058 mol). The resulting suspension was stirred for 10 minutes at room temperature (25° C.). To the stirred solution was added sodium bicarbonate (39.25 g, 0.467 mol) and acetone (49 mL). The resulting mixture was cooled to about 1° C. To the cooled solution was added a solution of potassium peroxymonosulfate (0.038 mol) dissolved in aqueous ethylenediaminetetraacetic acid (EDTA) (123 mL of 0.004M solution) over 10 min to form a reaction mixture as a suspension. The reaction temperature was kept below 5° C. during the addition of the potassium peroxymonosulfate solution. The reaction mixture was stirred for 5 min. The reaction was then quenched by the addition of aqueous sodium bisulfite (14.7 g in 30 mL water) at 2° C. The quenched reaction mixture was acidified by addition of aqueous HCl (6N, 88 mL). Sodium chloride (73.6 g) was added to the acidified reaction mixture and the resulting mixture was extracted with ethyl acetate (2×75 mL). The ethyl acetate extracts were combined and washed with deionized water (50 mL) and brine (50 mL), and then dried over anhydrous $MgSO_4$. The dried extract was filtered and concentrated under vacuum to yield the desired substituted benzyl sulfonylacetic acid compounds (yield 64-73%).

Compound 12a: m.p=110-111° C. Compound 12b: m.p.=142-146° C.

Compound 12c: m.p.=144-146 ° C. Compound 12d: m.p.=124-126° C.

Step C. General Preparation of Compounds of Examples 29-32.

To a solution of a substituted benzylsulfinylacetic acid (12a, 12b, 12c or 12d) prepared according to Step B (10 mmol) in toluene (100 mL, 25° C.) was added catalytic amounts of piperidine (0.1 mL) and benzoic acid (134 mg). To the resulting mixture was added a substituted benzaldehyde 13a or 13b (10 mmol) to form a reaction mixture. The reaction mixture was warmed to reflux temperature and maintained at reflux for 6 hours in a reaction vessel equipped with Dean-Stark trap. After 6 hours, the reaction mixture was cooled to room temperature (25° C.). The cooled reaction mixture was washed successively with saturated aqueous sodium hydrogen carbonate (3×30 mL), saturated aqueous sodium bisulfite (1×40 mL), aqueous hydrochloric acid (1N, 1×40 mL), and water (1×60 mL). The toluene layer was dried over anhydrous sodium sulfate, filtered and concentrated under vacuum to yield a solid residue. The solid residue obtained after concentration was purified by crystallization or by silica gel column chromatography to yield the following desired compounds as listed in Table 6.

TABLE 6

| Example # | Yield | M.P. ° C. | Structure |
|---|---|---|---|
| 29 | 27% | 92–94 | (structure) |
| 30 | 33% | 140–146 | (structure) |
| 31 | 18% | 112–115 | (structure) |

TABLE 6-continued

| Example # | Yield | M.P. ° C. | Structure |
|---|---|---|---|
| 32 | 43% | 270–274 | (structure) |
| 33 | 24 | 136–140 | (structure) |

EXAMPLE 33

Preparation of (E)-2,4,6-trimethoxystyryl-4-methoxy-3-aminobenzylsulfoxide by Reduction of (E)-2,4,6-trimethoxystyryl-4-methoxy-3-nitrobenzylsulfoxide (E)-2,4,6-Trimethoxystyryl-4-methoxy-3-nitrobenzylsulfoxide (1.3 mmol) was dissolved in a 2 to 1mixture of acetone and water (50 mL). The resulting mixture was heated to 50° C. After heating at 50° C. for 30 min, sodium dithionite (26.3 mmol) was added to the heated reaction mixture (portionwise over 20 minutes). The resulting mixture was maintained at 50° C. for 1hour, then cooled to room temperature (25° C.). Water (50 mL) was added to the cooled mixture. The resulting mixture was extracted with ethyl acetate (3×50 mL). The ethyl acetate extracts were combined and washed with saturated aqueous NaHCO$_3$. The ethyl acetate extract was dried over anhydrous sodium sulfate, filtered and concentrated under reduced pressure to yield the crude product. The crude product was recrystallized from 2-propanol to afford the desired (E)-2,4,6-trimethoxy styryl-3-amino-4-methoxybenzylsulfoxide, as listed in Table 6.

EXAMPLE 34

Oxidation of (E)-2,4,6-trimethoxystyryl-4-methoxybenzl sulfoxide (a Compound of the Invention) to Prepare (E)-2,4,6-trimethoxystyryl-4-methoxybenzyl sulfone (E)-2,4,6-trimethoxystyryl-4-methoxybenzyl sulfoxide (3 g) is dissolved in glacial acetic acid (30 mL) and cooled to 0° C. To the cooled solution is added hydrogen peroxide (7.5 mL of a 30% solution) to form a reaction mixture. The reaction mixture is heated to reflux temperature and maintained at reflux for 1 hour. After 1 hour, the heated reaction mixture is poured onto crushed water ice (200 g). A solid precipitate is formed. The precipitate is separated by filtration, dried, and recrystallized from 2-propanol to yield the desired (E)-2,4,6-trimethoxystyryl-4-methoxybenzyl sulfone.

EXAMPLE 35

Effect of α,β-Unsaturated Sulfoxides on Tumor Cell Lines

A. Cells.

B. Treatment with Sulfoxides and Viability Assay

The effect of the α,β-unsaturated sulfoxides according to Formula I on tumor cells of prostate, colon, lung and breast origin was examined by utilizing the following cell lines: prostate tumor cell line DU-145; colorectal carcinoma cell line DLD-1; non-small cell lung carcinoma cell line H157; and breast tumor cell line BT-20. BT-20 is an estrogen-unresponsive cell line. BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH/3T3 (normal murine fibroblasts) and HFL-1 cells (normal diploid human lung fibroblasts) were grown in DMEM containing 10% calf serum supplemented with penicillin and streptomycin.

Cells were plated at density levels of $1.0\times10^5$ cells per well in six-well plates. Cell cultures were maintained at 37° C. in a humidified atmosphere of 5% $CO_2$.

Cells were treated with compounds of the invention at doses ranging from 10 nM to 5 µM concentration, and cell viability was determined after 96 hours by the Trypan blue exclusion method.

The results are set forth in Table 7. Values are reported as the $GI_{50}$, i.e., the concentration (µM) required for 50% growth inhibition as compared to vehicle (DMSO) treated cells. The values reported in Table 7 are: *=10-100 nM; =100 nM-1µM; and *=>1µM.

Cells were treated with the test compound at concentrations in the range from 10 nM to 5 µM, and cell viability was determined after 96 hours by the Trypan blue exclusion method.

TABLE 7

| Example # | $GI_{50}$ for DU145, BT20, H157, DLD1 |
|---|---|
| 29 | ** |
| 30 | * |
| 31 | *** |
| 32 | Not tested |
| 33 | *** |

EXAMPLE 36

Radioprotective Effect of α,β-Unsaturated Sulfoxides on Cultured Normal Human Cells The radioprotective effect of α,β-unsaturated sulfoxides on cultured normal cells is evaluated as follows.

HFL-1 cells are plated into 24 well dishes at a cell density of 3000 cells per 10 $mm^2$ in DMEM completed with 10% fetal bovine serum and antibiotics. α,β-Unsaturated sulfoxide test compound is added to the cells 24 hours later at concentrations 0.25, 0.5, 1.0 and 2.0 micromolar, using DMSO as a solvent. Control cells are treated with DMSO alone. The cells are exposed to the test compound or DMSO for 24 hrs. The cells are then irradiated with either 10 Gy or 15 Gy of ionizing radiation (IR) using a J. L. Shepherd Mark 1, Model 30-1 Irradiator equipped with [137]cesium as a source.

After irradiation, the medium on the test and control cells is removed and replaced with fresh growth medium without the test compounds or DMSO. The irradiated cells are incubated for 96 hours and duplicate wells are trypsinized and replated onto 100 $mm^2$ tissue culture dishes. The replated cells are grown under normal conditions with one change of fresh medium for 3 weeks. The number of colonies from each 100 $mm^2$ culture dish, which represents the number of surviving cells, is determined by staining the dishes as described below.

To visualize and count the colonies derived from the clonal outgrowth of individual radioprotected cells, the medium is removed and the plates are washed one time with ambient temperature phosphate buffered saline. The cells are stained with a 1:10 diluted Modified Giemsa staining solution (Sigma) for 20 minutes. The stain is removed, and the plates are washed with tap water. The plates are air-dried, the number of colonies from each plate is counted and the average from duplicate plates is determined.

EXAMPLE 37

Effect of Exposure to Ionizing Radiation on Normal and Malignant Hematopoietic Progenitor Cell Growth After Pretreatment with α,β-Unsaturated Sulfoxides of the Invention The effect of ionizing radiation on normal and malignant hematopoietic progenitor cells which are pretreated with α,β-unsaturated sulfoxides of the invention is determined by assessing cloning efficiency and development of the pretreated cells after irradiation.

To obtain hematopoietic progenitor cells, human bone marrow cells (BMC) or peripheral blood cells (PB) are obtained from normal healthy, or acute or chronic myelogenous leukemia (AML, CML), volunteers by Ficoll-Hypaque density gradient centrifugation, and are partially enriched for hematopoietic progenitor cells by positively selecting $CD34^+$ cells with immunomagnetic beads (Dynal A. S., Oslo, Norway). The $CD34^+$ cells are suspended in supplemented alpha medium and incubated with mouse anti-HPCA-I antibody in 1:20 dilution, 45 minutes, at 4° C. with gentle inverting of tubes. Cells are washed ×3 in supplemented alpha medium, and then incubated with beads coated with the Fc fragment of goat anti-mouse $IgG_1$ (75 µl of immunobeads/107 $CD34^+$ cells). After 45 minutes of incubation (4° C.), cells adherent to the beads are positively selected using a magnetic particle concentrator as directed by the manufacturer.

$2\times10^4$ $CD34^+$ cells are incubated in 5 mL polypropylene tubes (Fisher Scientific, Pittsburgh, Pa.) in a total volume of 0.4 mL of Iscove's modified Dulbecco's medium (IMDM) containing 2% human AB serum and 10 mM Hepes buffer. α,β-Unsaturated sulfoxide test compounds are added to the cells; in four different concentrations (0.25 µM, 0.5 µM, 1.0 µM and 2.0 µM). Control cells receive DMSO alone. The cells are incubated for 20-24 hours and irradiated with 5 Gy or 10 Gy of ionizing radiation.

Immediately after irradiation, the medium is removed and replaced with fresh medium without the test compound or DMSO. Twenty-four hours after irradiation, the treatment and control cells are prepared for plating in plasma clot or methylcellulose cultures. Cells ($1\times10^4$ $CD34^+$ cells per dish) are not washed before plating.

Assessment of the cloning efficiency and development of the treated hematopoietic progenitor cells are carried out essentially as reported in Gewirtz et al., *Science* 242, 1303-1306 (1988), the disclosure of which is incorporated herein by reference.

EXAMPLE 38

Bone Marrow Purging with Ionizing Radiation After Pretreatment with α,β-Unsaturated Sulfoxides of the Invention Bone marrow is harvested from the iliac bones of an individual under general anesthesia in an operating room using standard techniques. Multiple aspirations are taken into heparinized syringes. Sufficient marrow is withdrawn so that the individual will be able to receive about $4 \times 10^8$ to about $8 \times 10^8$ processed marrow cells per kg of body weight. Thus, about 750 to 1000 mL of marrow is withdrawn. The aspirated marrow is transferred immediately into a transport medium (TC-199, Gibco, Grand Island, N.Y.) containing 10,000 units of preservative-free heparin per 100 mL of medium. The aspirated marrow is filtered through three progressively finer meshes to obtain a cell suspension devoid of cellular aggregates, debris and bone particles. The filtered marrow is then processed further into an automated cell separator (e.g., Cobe 2991Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure is carried out as follows. Cells in the buffy coat preparation are adjusted to a cell concentration of about $2 \times 10^7$/mL in TC-199 containing about 20% autologous plasma. α,β-Unsaturated sulfoxides of the invention, for example, at concentrations of from 0.25 μM to 2.0 μM are added to the transfer packs containing the cell suspension and incubated in a 37° C. waterbath for 20-24 hours with gentle shaking. The transfer packs are then exposed to 5-10 Gy ionizing radiation. Recombinant human hematopoietic growth factors, e.g., rH IL-3 or rH GM-CSF, may be added to the suspension to stimulate growth of hematopoietic neoplasms and thereby increase their sensitivity to ionizing radiation.

The cells may then either be frozen in liquid nitrogen or washed once at 4° C. in TC-199 containing about 20% autologous plasma. Washed cells are then infused into the individual. Care must be taken to work under sterile conditions wherever possible and to maintain scrupulous aseptic techniques at all times.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound of Formula IA:

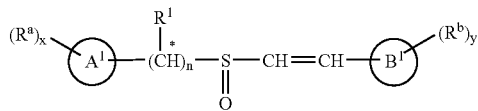

IA wherein:
$A^1$ is aryl or heteroaryl and x is 0, 1, 2, 3, 4 or 5;
either $B^1$ is aryl and y is 1, 2, 3, 4 or 5, or $B^1$ is heteroaryl and y is 0, 1, 2, 3, 4 or 5;
provided that x does not exceed the number of substitutable positions of the ring to which each $R^a$ is attached; and y does not exceed number of substitutable positions of the ring to which each $R^b$ is attached;
n is 1;
$R^1$ is —H, —($C_1$-$C_8$)hydrocarbyl, —CN, —$CO_2$($C_1$-$C_6$)alkyl or halo($C_1$-$C_6$)alkyl;
the configuration of the substituents on the carbon-carbon double bond is either E- or Z—;
the configuration of the substituents on the sulfoxide sulfur atom is R—, S— or any mixture of R— and S—;
each $R^a$ is independently selected from the group consisting of halogen; —($C_1$-$C_8$)hydrocarbyl, —C(=O)$R^2$, —$NR^2_2$, —NHC(=O)$R^3$, —NHSO$_2R^3$, —NH$R^4$, —NHC$R^2R^4$C(=O)$R^6$, —C(=O)O$R^2$, —C(=O)NH$R^2$, —NO$_2$, —CN, —O$R^2$, —P(=O)(OH)$_2$, dimethylamino($C_2$-$C_6$ alkoxy), —NHC(=NH)NH$R^2$, —($C_1$-$C_6$)haloalkyl, —($C_1$-$C_6$)haloalkoxy and —N=CH—$R^7$;
each $R^b$ attached to aryl is independently selected from the group consisting of —C(=O)$R^2$, halogen, —NO$_2$, —CN, —O$R^2$, —C(=O)O$R^2$, —$NR^2_2$, ($C_1$-$C_6$)haloalkyl and ($C_1$-$C_6$)haloalkoxy;
each $R^b$ attached to heteroaryl is independently selected from the group consisting of —($C_1$-$C_8$)hydrocarbyl, —C(=O)$R^2$, halogen, —NO$_2$, —CN, —O$R^2$, —C(=O)O$R^2$, —$NR^2_2$, ($C_1$-$C_6$)haloalkyl and ($C_1$-$C_6$) haloalkoxy;
each $R^2$ is independently selected from the group consisting of —H and —($C_1$-$C_8$)hydrocarbyl;
each $R^3$ is independently selected from the group consisting of —H, —($C_1$-$C_8$)hydrocarbyl, —O($C_1$-$C_8$)hydrocarbyl, substituted and unsubstituted aryl, substituted heterocyclyl($C_1$-$C_3$)alkyl, heteroaryl($C_1$-$C_3$)alkyl, —($C_2$-$C_{10}$)heteroalkyl, —($C_1$-$C_6$)haloalkyl, —C$R^2R^4$NH$R^5$, —N($R^2$)$_2$, —($C_1$-$C_3$)alkyleneNH$_2$, —($C_1$-$C_3$)alkylene-N(CH$_3$)$_2$, —($C_1$-$C_3$)perfluoroalkylene-N(CH$_3$)$_2$, —($C_1$-$C_3$)alkylene-N$^+$(($C_1$-$C_3$)alkyl)$_3$, —($C_1$-$C_3$)alkylene-N$^+$(CH$_2$CH$_2$OH)$_3$, —($C_1$-$C_3$)alkylene-O$R^2$, —($C_1$-$C_4$)alkylene-CO$_2R^2$, —($C_1$-$C_4$)alkylene-C(=O)halogen, halo($C_1$-$C_3$)alkyl-, —($C_1$-$C_3$) alkylene-C(=O)($C_1$-$C_3$)alkyl, and —($C_1$-$C_4$) perfluoroalkylene-CO$_2R^2$;
each $R^4$ is independently selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), and —CH$_2$-(4-hydroxyphenyl);
each $R^5$ is independently selected from the group consisting of —H and a carboxy terminally linked peptidyl residue containing from 1 to 3 amino acids in which the terminal amino group of the peptidyl residue is present as a functional group selected from the group consisting of —NH$_2$ and —NHC(=O)($C_1$-$C_6$)alkyl, —NH($C_1$-$C_6$)alkyl, —N($C_1$-$C_6$alkyl)$_2$ and —NHC(=O)O($C_1$-$C_7$)hydrocarbyl;
each $R^6$ is independently selected from the group consisting of —O$R^2$ and an N-terminally linked peptidyl residue containing from 1 to 3 amino acids in which the terminal carboxyl group of the peptidyl residue is present as a functional group selected from the group consisting of —CO$_2R^2$ and —C(=O)N$R^2_2$; and each $R^7$ is independently selected from the group consisting of substituted and unsubstituted aryl and substituted and unsubstituted heteroaryl;

* indicates that, when $R^1$ is other than —H, the configuration of the substituents on the designated carbon atom is R—, S— or any mixture of R— and S—; or a salt of such a compound.

2. A compound according to claim 1 of Formula IAz:

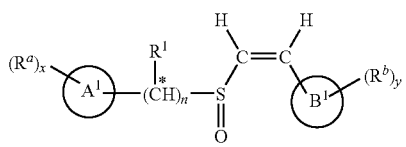

or a salt thereof.

3. A compound according to claim 1 of the Formula IAe:

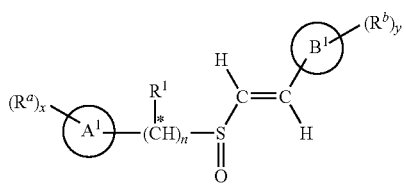

or a salt thereof.

4. A compound according to claim 1, or a salt thereof, wherein the sum of x and y is greater than zero.

5. A compound according to claim 4, or a salt thereof, wherein $A^1$ is an aryl radical.

6. A compound according to claim 5 selected from the group consisting of: (1E)-2-(4-fluorophenyl)-1-[(naphthylmethyl)sulfinyl]ethene; (1E)-2-(4-chlorophenyl)-1-[(naphthylmethyl)sulfinyl]ethene; (1E)-2-(4-bromophenyl)-1-[(naphthylmethyl)sulfinyl]ethene; (1E)-2-(2-nitrophenyl)-1-[(naphthylmethyl)sulfinyl]-ethene; (1E)-2-(3-nitrophenyl)-1-[(naphthylmethyl)sulfinyl]ethene; and (1E)-2-(4-nitrophenyl)-1-[(naphthylmethyl)sulfinyl]ethene.

7. A compound according to claim 5, of Formula IB:

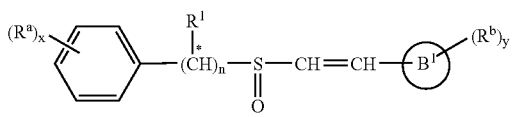

or a salt thereof.

8. A compound according to claim 7, or a salt thereof, wherein each $R^a$ is independently selected from the group consisting of halogen, $(C_1-C_6)$alkyl, $(C_1-C_6)$alkoxy, —$NO_2$, —CN, —C(=O)$OR^2$, —OH, —$NH_2$, $(C_1-C_6)$trifluoroalkoxy and —$CF_3$.

9. A compound according to claim 7, of Formula IC:

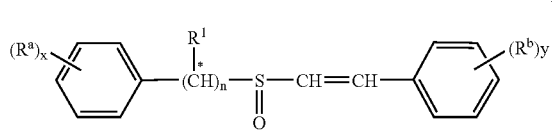

or a salt thereof.

10. A compound according to claim 9 wherein each $R^a$ is independently selected from the group consisting of halogen, $(C_1-C_6)$alkyl, $(C_1-C_6)$alkoxy, —$NO_2$, —CN and —$CF_3$, and each $R^b$ is independently selected from the group consisting of halogen, $(C_1-C_6)$alkoxy, —$NO_2$, —CN and —$CF_3$.

11. A compound according to claim 9, or a salt thereof, wherein the configuration of the substituents on the carbon-carbon double bond is E-.

12. A compound according to claim 11, or a salt thereof, wherein x is 0, 1 or 2 and y is 1 or 2.

13. A compound according to claim 11 selected from the group consisting of: (1E)-1-{[(3-amino-4-methoxyphenyl)methyl]sulfinyl}-2-(2,4,6-trimethoxyphenyl)ethene; (1E)-1-{[(3-hydroxy-4-methoxyphenyl)methyl]sulfinyl}-2-(2,4,6-trimethoxyphenyl)ethene; (1E)-1-{[(4-methoxy-3-nitrophenyl)methyl]sulfinyl}-2-(2,4,6-trimethoxyphenyl)ethene; 2-({[5-({[(1E)-2-(2,4,6-trimethoxyphenyl)vinyl]sulfinyl}-methyl)-2-methoxyphenyl]amino}sulfonyl)acetic acid; 2-{N-[5-({[(1E)-2-(2,4,6-trimethoxyphenyl)vinyl]sulfinyl}-methyl)-2-methoxyphenyl]carbamoyl}acetic acid; [5-({[(1E)-2-(2,4,6-trimethoxyphenyl)vinyl]sulfinyl}methyl)-2-methoxyphenyl]aminocarboxamidine; 2-{[5-({[(1E)-2-(2,4,6-trimethoxyphenyl)vinyl]sulfinyl}methyl)-2-methoxyphenyl]amino}acetic acid; N-[5-({[(1E)-2-(2,4,6-trimethoxyphenyl)vinyl]sulfinyl}methyl)-2-methoxyphenyl](3,5-dinitro-phenyl)carboxamide; N-[5-({[(1E)-2-(2,4,6-trimethoxyphenyl)vinyl]sulfinyl}methyl)-2-methoxyphenyl](3,5-diaminophenyl)carboxamide; N-[5-({[(1E)-2-(2,4,6-trimethoxy-phenyl)vinyl]sulfinyl}methyl)-2-methoxyphenyl]-2-chloroacetamide; N-[5-({[(1E)-2-(2,4,6-trimethoxyphenyl)vinyl]sulfinyl}methyl)-2-methoxyphenyl]-2-(4-methyl-piperazinyl)acetamide; N-[5-({[(1E)-2-(2,4,6-trimethoxyphenyl)vinyl]sulfinyl}methyl)-2-methoxyphenyl]benzamide; N-[5-({[(1E)-2-(2,4,6-trimethoxyphenyl)vinyl]sulfinyl}-methyl)-2-methoxyphenyl](4-nitrophenyl)carboxamide; N-[5-({[(1E)-2-(2,4,6-trimethoxyphenyl)vinyl]sulfinyl}methyl)-2-methoxyphenyl](4-aminophenyl)carboxamide; N-[5-({[(1E)-2-(2,4,6-trimethoxyphenyl)-vinyl]sulfinyl}methyl)-2-methoxyphenyl](2R)-2,6-diaminohexanamide; N-[5-({[(1E)-2-(2,4,6-trimethoxyphenyl)vinyl]sulfinyl}methyl)-2-methoxyphenyl](2R)-2-amino-3-hydroxypropanamide; N-[5-({[(1E)-2-(2,4,6-trimethoxyphenyl)vinyl]sulfinyl}methyl)-2-methoxyphenyl](2S)-2-amino-3-hydroxypropanamide; N-[5-({[(1E)-2-(2,4,6-trimethoxyphenyl)vinyl]sulfinyl}methyl)-2-methoxyphenyl]aminamide; (1E)-1-({[4-methoxy-3-(methylamino)phenyl]methyl}sulfinyl)-2-(2,4,6-trimethoxyphenyl)ethene; N-[5-({[(1E)-2-(2,4,6-trimethoxyphenyl)vinyl]sulfinyl}methyl)-2-methoxyphenyl]acetamide; [5-({[(1E)-2-(2,4,6-trimethoxyphenyl)vinyl]sulfinyl}methyl)-2-methoxyphenyl][(2,4-dinitrophenyl)sulfonyl]amine; [5-({[(1E)-2-(2,4,6-trimethoxyphenyl)vinyl]sulfinyl}methyl)-2-methoxyphenyl][(2,4-diaminophenyl)sulfonyl]amine; N-[5-({[(1E)-2-(2,4,6-trimethoxyphenyl)vinyl]sulfinyl}methyl)-2-methoxyphenyl]-2-(dimethylamino)-acetamide; 2-{[5-({[(1E)-2-(2,4,6-trimethoxyphenyl)vinyl]sulfinyl}methyl)-2-methoxy-phenyl]amino}propanoic acid; N-[5-({[(1E)-2-(2,4,6-trimethoxyphenyl)vinyl]sulfinyl}-methyl)-2-methoxyphenyl][4-(4-methylpiperazinyl)phenyl]carboxamide; N-[5-({[(1E)-2-(2,4,6-trimethoxyphenyl)vinyl]sulfinyl}methyl)-2-methoxyphenyl]-2-hydroxyacetamide; N-[5-({[(1E)-2-(2,4,6-trimethoxyphenyl)vinyl]sulfinyl}methyl)-2-methoxyphenyl]-2-pyridylacetamide; {N-[5-({[(1E)-2-(2,4,6-trimethoxyphenyl)vinyl]sulfinyl}methyl)-2-methoxyphenyl]carbamoyl}methyl acetate; N-[5-({[(1E)-2-(2,4,6-trimethoxy-phenyl)vinyl]sulfinyl}methyl)-2-methoxyphenyl]-2-hydroxypropanamide; N-[5-({[(1E)-2-(2,4,6-trimethoxyphenyl)vinyl]sulfinyl}methyl)-2-methoxyphenyl]-2-(triethylamino)acetamide; N-[5-({[(1E)-2-(2,4,6-trimethoxyphenyl)vinyl]sulfinyl}-methyl)-2-methoxyphenyl]-2-[tris(2-hydroxyethyl)amino]acetamide; N-[5-({[(1E)-2-(2,4,6-trimethoxyphenyl)vinyl]sulfinyl}methyl)-2-methoxyphenyl]-2-hydroxy-2-methylpropanamide; 1-{N-[5-({[(1E)-2-(2,4,6-trimethoxyphenyl)vinyl]sulfinyl}-methyl)-2-methoxyphenyl]carbamoyl}-isopropyl acetate; N-[5-({[(1E)-2-(2,4,6-trimethoxyphenyl)vinyl]sulfinyl}methyl)-2-methoxyphenyl]-2,2,2-trifluoroacetamide; [5-({[(1E)-2-(2,4,6-trimethoxyphenyl)vinyl]sulfinyl}methyl)-2-methoxyphenyl][(trifluoro-methyl)sulfonyl]amine; 3-{N-[5-({[(1E)-2-(2,4,6-trimethoxyphenyl)vinyl]-sulfinyl}methyl)-2-methoxyphenyl]carbamoyl}propanoic acid; 3-{N-[5-({[(1E)-2-(2,4,6-trimethoxyphenyl)vinyl]sulfinyl}-methyl)-2-methoxyphenyl]carbamoyl}propanoyl chloride; 3-[({N-[5-({[(1E)-2-(2,4,6-trimethoxyphenyl)vinyl]sulfinyl}-methyl)-2-methoxyphenyl]carbamoyl}methyl)oxycarbonyl]propanoic acid; 4-{N-[5-({[(1E)-2-(2,4,6-trimethoxyphenyl)vinyl]sulfinyl}-methyl)-2-methoxyphenyl]carbamoyl}butanoic acid; N-[5-({[(1E)-2-(2,4,6-trimethoxyphenyl)vinyl]sulfinyl}methyl)-2-methoxyphenyl]-2-(phosphonooxy)acetamide, disodium salt; 4-{[5-({[(1E)-2-(2,4,6-trimethoxy-phenyl)vinyl]sulfinyl}methyl)-2-methoxyphenyl]amino}butanoic acid; 3-{[5-({[(1E)-2-(2,4,6-trimethoxyphenyl)vinyl]sulfinyl}methyl)-2-methoxyphenyl]amino}propanoic acid; N-[5-({[(1E)-2-(2,4,6-trimethoxyphenyl)vinyl]sulfinyl}methyl)-2-methoxyphenyl]methoxycarboxamide; [5-({[(1E)-2-(2,4,6-trimethoxy-phenyl)vinyl]sulfinyl}methyl)-2-methoxyphenyl][(4-methoxyphenyl)sulfonyl]amine; {N-[5-({[(1E)-2-(2,4,6-trimethoxyphenyl)vinyl]sulfinyl}methyl)-2-methoxyphenyl]carbamoyl}ethyl acetate; methyl-3-{N-[5-({[(1E)-2-(2,4,6-trimethoxyphenyl)vinyl]-sulfinyl}-methyl)-2-methoxyphenyl]carbamoyl}propanoate; ethyl-2-{N-[5-({[(1E)-2-(2,4,6-trimethoxyphenyl)vinyl]sulfinyl}-methyl)-2-methoxyphenyl]carbamoyl}acetate; N-[5-({[(1E)-2-(2,4,6-trimethoxyphenyl)vinyl]sulfinyl}methyl)-2-methoxyphenyl]-2,2,3,3,3-pentafluoropropanamide; methyl-2-{N-[5-({[(1E)-2-(2,4,6-trimethoxyphenyl)vinyl]sulfinyl}methyl)-2-methoxyphenyl]carbamoyl}-2,2-difluoroacetate; 3-{N-[5-({[(1E)-2-(2,4,6-trimethoxyphenyl)vinyl]sulfinyl}-methyl)-2-methoxyphenyl]carbamoyl}-2,2,3,3-tetrafluoropropanoic acid; N-[5-({[(1E)-2-(2,4,6-trimethoxy-phenyl)vinyl]sulfinyl}methyl)-2-methoxyphenyl]-2-aminoacetamide; 2-{N-[5-({[(1E)-2-(2,4,6-trimethoxyphenyl)vinyl]sulfinyl}-methyl)-2-methoxyphenyl]carbamoyl}-2,2-difluoroacetic acid; N-[5-({[(1E)-2-(2,4,6-trimethoxyphenyl)vinyl]sulfinyl}methyl)-2-methoxyphenyl]-2-(dimethylamino)-2,2-difluoroacetamide, 4-((1E)-2-{[(4-fluorophenyl)methyl]sulfinyl}vinyl)benzoic acid; 4-((1E)-2-{[(4-iodophenyl)methyl]-sulfinyl}vinyl)benzoic acid; 4-((1E)-2-{[(4-chlorophenyl)methyl]sulfinyl}vinyl)benzoic acid; 1-[5-((1E)-2-{[(4-chlorophenyl)methyl]sulfinyl}vinyl)-2-fluorophenyl]-2-(dimethylamino)ethan-1-one; (1E)-2-(2,4-difluorophenyl)-1-{[(4-bromophenyl)methyl]-sulfinyl}ethene; (1E)-2-(3-amino-4-fluorophenyl)-1-{[(4-chlorophenyl)methyl]sulfinyl}-ethene; (1E)-1-{[(4-fluorophenyl)methyl]sulfinyl}-2-(2,3,4,5,6-pentafluorophenyl)-ethene; (1E)-1-{[(4-chlorophenyl)methyl]sulfinyl}-2-(2,3,4,5,6-pentafluoro-phenyl)ethene; (1E)-1-{[(4-bromophenyl)methyl]sulfinyl}-2-(2,3,4,5,6-pentafluoro-phenyl)ethene; (1E)-2-(4-fluorophenyl)-1-{[(2,3,4,5,6-pentafluorophenyl)-methyl]sulfinyl}ethene; (1E)-2-(4-chlorophenyl)-1-{[(2,3,4,5,6-pentafluorophenyl)-methyl]sulfinyl}ethene; (1E)-2-(4-bromophenyl)-1-{[(2,3,4,5,6-pentafluorophenyl)-methyl]sulfinyl}ethene; (1E)-1-{[(3,4-dichlorophenyl)methyl]sulfinyl}-2-(2,3,4,5,6-pentafluorophenyl)ethene; (1E)-1-{[(4-iodophenyl)methyl]sulfinyl}-2-(2,3,4,5,6-pentafluorophenyl)ethene; (1E) 1-{[(4-fluorophenyl)methyl]sulfinyl}-2-(2-hydroxy-3,5-dinitrophenyl)ethene; (1E)-1-{[(4-bromophenyl)methyl]sulfinyl}-2-(2-hydroxy-3,5-dinitrophenyl)ethene; (1E)-1-{[(4-chlorophenyl)methyl]sulfinyl}-2-(2-hydroxy-3,5-dinitrophenyl)ethene; (1E)-1-{[(2,4-dichlorophenyl)methyl]sulfinyl}-2-(2-hydroxy-3,5-dinitrophenyl)ethene; (1E)-1-{[(4-methoxyphenyl)methyl]sulfinyl}-2-(2,4,6-trimethoxy-phenyl)ethene; (1E)-1-{[(4-methoxyphenyl)methyl]sulfinyl}-2-(3,4,5-trimethoxy-phenyl)ethene; (1E)-1-{[(2-nitro-4,5-dimethoxyphenyl)methyl]sulfinyl}-2-(3,4,5-trimethoxyphenyl)ethene; (1E)-1-{[(2-nitro-4,5-dimethoxyphenyl)methyl]sulfinyl}-2-(2,4,6-trimethoxyphenyl)ethene; (1E)-1-{[(4-fluorophenyl)methyl]sulfinyl}-2-(2,3,4-trifluorophenyl)ethene; (1E)-1-{[(4-chlorophenyl)methyl]sulfinyl}-2-(2,3,4-trifluorophenyl)ethene; (1E)-1-{[(4-methoxyphenyl)methyl]sulfinyl}-2-(2,6-methoxy-4-hydroxyphenyl)ethene; (1E)-1-{[(4-methoxyphenyl)methyl]sulfinyl}-2-(2,3,5,6-tetrafluorophenyl)ethene; (1E)-1-{[(4-methoxyphenyl)methyl]sulfinyl}-2-(2,4,5-trimethoxyphenyl)ethene; (1E)-1-{[(4-methoxyphenyl)methyl]sulfinyl}-2-(2,3,4-trimethoxyphenyl)ethene; (1E)-1-{[(4-methoxyphenyl)methyl]sulfinyl}-2-(3-nitro-4-hydroxy-5-methoxyphenyl)ethene; (1E)-1-{[(4-methoxyphenyl)methyl]sulfinyl}-2-(3,4-dimethoxy-6-nitrophenyl)ethene; (1E)-1-{[(4-methoxyphenyl)methyl]sulfinyl}-2-(3,4-dimethoxy-5-iodophenyl)ethene; (1E)-1-{[(4-methoxyphenyl)methyl]sulfinyl}-2-(2,6-dimethoxy-4-fluorophenyl)ethene; (1E)-1-{[(4-methoxyphenyl)methyl]sulfinyl}-2-(2-hydroxy-4,6-dimethoxyphenyl)ethene; (1E)-1-{[(4-chlorophenyl)methyl]sulfinyl}-2-(2,4,6-trimethoxyphenyl)ethene; (1E)-1-{[(4-chlorophenyl)methyl]sulfinyl}-2-(2,6-dimethoxy-4-fluorophenyl)ethene; (1E)-1-{[(4-chlorophenyl)methyl]sulfinyl}-2-(2-hydroxy-4,6-dimethoxyphenyl)ethene; (1E)-1-{[(4-bromophenyl)methyl]sulfinyl}-2-(2,4,6-trimethoxyphenyl)ethene; (1E)-1-{[(4-bromophenyl)methyl]sulfinyl}-2-(2,6-dimethoxy-4-fluorophenyl)ethene; (1E)-1-{[(2,4,6-trimethoxyphenyl)methyl]sulfinyl}-2-(2,4,6-trimethoxyphenyl)ethene; (1E)-1-{[(2,3,4-trimethoxyphenyl)methyl]sulfinyl}-2-(2,6-dimethoxyphenyl)ethene; (1E)-1-{[(3,4,5-trimethoxyphenyl)methyl]sulfinyl}-2-(2,4,6-trimethoxyphenyl)ethene; (1E)-1-{[(3,4,5-trimethoxyphenyl)methyl]sulfinyl}-2-(2,6-dimethoxyphenyl)ethene; (1E)-1-{[(3,4,5-trimethoxyphenyl)methyl]sulfinyl}-2-(4-fluorophenyl)ethene; (1E)-2-(4-fluorophenyl)-1-({[4-(trifluoromethyl)phenyl]methyl}-sulfinyl)ethene; (1E)-2-(4-chlorophenyl)-1-({[4-(trifluoromethyl)phenyl]methyl}-sulfinyl)ethene; (1E)-2-(4-bromophenyl)-1-({[4-(trifluoromethyl)phenyl]methyl}-sulfinyl)ethene; (1E)-1-{[(2,4-dichlorophenyl)methyl]sulfinyl}-2-(4-fluorophenyl)ethene; (1E)-1-{[(2,4-dichlorophenyl)methyl]sulfinyl}-2-(4-chloro-phenyl)ethene; (1E)-1-{[(3,4-dichlorophenyl)methyl]sulfinyl}-2-(4-fluoro-phenyl)ethene; (1E)-1-{[(3,4-dichloro-phenyl)methyl]sulfinyl}-2-(4-chloro-phenyl)ethene; (1E)-1-{[(3,4-dichloro-phenyl)methyl]sulfinyl}-2-(4-bromo-phenyl)ethene; (1E)-2-(4-fluorophenyl)-1-{[(4-nitrophenyl)methyl]sulfinyl}-ethene; 4-({[(1E)-2-(4-fluorophenyl)vinyl]-sulfinyl}methyl)benzene-carbonitrile; 4-({[(1E)-2-(4- chlorophenyl)vinyl]sulfinyl}-methyl)benzene-carbonitrile; 4-({[(1E)-2-(4-bromophenyl)vinyl]sulfinyl}-methyl)benzene-carbonitrile; (1E)-2-(3,4-difluorophenyl)-1-{[(4-chlorophenyl)methyl]-sulfinyl}ethene; (1E)-2-(3-chloro-4-fluorophenyl)-1-{[(4-chlorophenyl)methyl]-sulfinyl}ethene; (1E)-2-(2-chloro-4-fluorophenyl)-1-{[(4-chlorophenyl)methyl]-sulfinyl}ethene; (1E)-2-(2,4-dichlorophenyl)-1-{[(4-chlorophenyl)methyl]-sulfinyl}ethene; (1E)-2-(3,4-dichlorophenyl)-1-{[(4-chlorophenyl)-methyl]sulfinyl}ethene; (1E)-2-(2,3-dichlorophenyl)-1-{[(4-chlorophenyl)methyl]-sulfinyl}ethene; (1E)-2-(4-fluorophenyl)-1-{[(4-iodophenyl)methyl]-sulfinyl}ethene; (1E)-1-{[(4-fluorophenyl)methyl]sulfinyl}-2-(4-iodophenyl)-ethene; (1E)-1-{[(4-chlorophenyl)methyl]sulfinyl}-2-(4-iodophenyl)-ethene; (1E)-1-{[(4-bromophenyl)methyl]sulfinyl}-2-(4-iodophenyl)-ethene; (1E)-1-{[(4-bromophenyl)methyl]sulfinyl}-2-(4-chlorophenyl)-ethene; (1E)-2-(4-bromophenyl)-1-{[(4-iodophenyl)methyl]sulfinyl}ethene; (1E)-1-{[(4-iodophenyl)methyl]sulfinyl}-2-(4-nitrophenyl)-ethene; (1E)-1-{[(4-iodophenyl)methyl]sulfinyl}-2-(2-nitrophenyl)-ethene; (1E)-2-(4-iodophenyl)-1-{[(4-methoxyphenyl)methyl]sulfinyl}-ethene; (1E)-1-{[(2,4-dichlorophenyl)methyl]sulfinyl}-2-(4-iodophenyl)-ethene; (1E)-2-(3,4-dichlorophenyl)-1-{[(4-chlorophenyl)methyl]-sulfinyl}ethene; (1E)-2-(2-nitrophenyl)-1-{[(4-fluorophenyl)methyl]sulfinyl}-ethene; (1E)-2-(3-nitrophenyl)-1-{[(4-fluorophenyl)methyl]-sulfinyl}-ethene; (1E)-2-(4-nitrophenyl)-1-{[(4-fluorophenyl)methyl]sulfinyl}-ethene; (1E)-2-(2-trifluoromethylphenyl)-1-{[(4-fluorophenyl)methyl]sulfinyl}ethene; (1E)-2-(3-trifluoromethylphenyl)-1-{[(4-fluorophenyl)methyl]-sulfinyl}-ethene; (1E)-2-(4-trifluoromethylphenyl)-1-{[(4-fluorophenyl)methyl]-sulfinyl}ethene; (1E)-2-(2-trifluoro-methyl-4-fluorophenyl)-1-{[(4-fluorophenyl)-methyl]sulfinyl}ethene; (1E)-2-(2-nitrophenyl)-1-{[(4-chlorophenyl)methyl]sulfinyl}-ethene; (1E)-2-(3-nitrophenyl)-1-{[(4-chlorophenyl)methyl]sulfinyl}-ethene; (1E)-2-(4-nitrophenyl)-1-{[(4-chlorophenyl)-methyl]sulfinyl}-ethene; (1E)-2-(2-trifluoromethylphenyl)-1-{[(4-chlorophenyl)methyl]-sulfinyl}ethene; (1E)-2-(3-trifluoromethylphenyl)-1-{[(4-chlorophenyl)methyl]-sulfinyl}ethene; (1E)-2-(4-trifluoromethylphenyl)-1-{[(4-chlorophenyl)-methyl]sulfinyl}ethene; (1E)-2-(2-trifluoromethyl-4-fluorophenyl)-1-{[(4-chlorophenyl)-methyl]sulfinyl}ethene; (1E)-2-(2-nitrophenyl)-1-{[(2,4-dichlorophenyl)methyl]sulfinyl}-ethene; (1E)-2-(2-trifluoromethyl-4-fluorophenyl)-1-{[(2,4-dichloro-phenyl)methyl]sulfinyl}ethene; (1E)-2-(2-nitrophenyl)-1-{[(4-bromophenyl)methyl]sulfinyl}ethene; (1E)-2-(3-nitrophenyl)-1-{[(4-bromophenyl)methyl]sulfinyl}ethene; (1E)-2-(4-nitrophenyl)-1-{[(4-bromophenyl)methyl]sulfinyl}ethene; (1E)-2-(2-trifluoromethylphenyl)-1-{[(4-bromophenyl)methyl]sulfinyl}ethene; (1E)-2-(3-trifluoromethylphenyl)-1-{[(4-fluorophenyl)methyl]sulfinyl}ethene; (1E)-2-(4-trifluoromethylphenyl)-1-{[(4-bromophenyl)methyl]sulfinyl}ethene; (1E)-2-(2-nitrophenyl)-1-{[(4-cyanophenyl)methyl]sulfinyl}ethene; (1E)-2-(3-nitrophenyl)-1-{[(4-cyanophenyl)-methyl]sulfinyl}ethene; (1E)-2-(4-nitrophenyl)-1-{[(4-cyanophenyl)-methyl]sulfinyl}ethene; (1E)-2-(4-fluorophenyl)-1-{[(4-methylphenyl)methyl]sulfinyl}-ethene; (1E)-2-(4-bromophenyl)-1-{[(4-methylphenyl)methyl]sulfinyl}ethene; (1E)-2-(2-nitrophenyl)-1-{[(4-methylphenyl)methyl]sulfinyl}ethene; (1E)-2-(3-nitrophenyl)-1-{[(4-methylphenyl)methyl]sulfinyl}ethene; (1E)-2-(4-nitrophenyl)-1-{[(4-methylphenyl)methyl]sulfinyl}ethene; (1E)-2-(4-fluorophenyl)-1-{[(4-methoxyphenyl)methyl]sulfinyl}ethene; (1E)-2-(4-chlorophenyl)-1-{[(4-methoxyphenyl)methyl]-sulfinyl}ethene; (1E)-2-(4-bromophenyl)-1-{[(4-methoxyphenyl)methyl]-sulfinyl}ethene; (1E)-2-(2-nitrophenyl)-1-{[(4-methoxyphenyl)methyl]sulfinyl}ethene; (1E)-2-(3-nitrophenyl)-1-{[(4-methoxyphenyl)methyl]sulfinyl}ethene; (1E)-2-(4-nitrophenyl)-1-{[(4-methoxyphenyl)methyl]sulfinyl}ethene; (1E)-2-(4-chlorophenyl)-1-{[(4-nitrophenyl)methyl]-sulfinyl}ethene; (1E)-2-(4-fluorophenyl)-1-{[(4-nitrophenyl)methyl]sulfinyl}ethene; and salts thereof.

14. A compound according to claim 9 wherein:
   $R^a$ is selected from the group consisting of chlorine, fluorine and bromine, and said $R^a$ is bonded to the para position of the ring to which it is attached;
   x is 0 or 1;
   $R^b$ is selected from the group consisting of chlorine, fluorine, bromine, and methoxy, and said $R^b$ is bonded to the ortho or para position of the ring to which it is bonded; and
   y is 1, 2 or 3.

15. A compound according to claim 14 wherein the configuration of the substituents on the carbon-carbon double bond is E-.

16. A compound according to claim 15 selected from the group consisting of: (1E)-2-(2-chlorophenyl)-1-[benzylsulfinyl]ethene; (1E)-2-(4-chlorophenyl)-1-[benzylsulfinyl]ethene; (1E)-1-{[(4-chlorophenyl)methyl]sulfinyl}-2-(4-fluorophenyl)ethene; (1E)-2-(4-chlorophenyl)-1-{[(4-chlorophenyl)methyl]sulfinyl}-ethene; (1E)-2-(4-fluorophenyl)-1-{[(4-fluorophenyl)methyl]sulfinyl}ethene; (1E)-2-(2,4-difluorophenyl)-1-{[(4-fluorophenyl)methyl]sulfinyl}ethene; (1E)-1-{[(4-bromophenyl)methyl]sulfinyl}-2-(4-fluorophenyl)ethene; (1E)-2-(4-bromophenyl)-1-{[(4-bromophenyl)methyl]sulfinyl}ethene; (1E)-2-(4-bromophenyl)-1-{[(4-fluorophenyl)methyl]sulfinyl}ethene; and (1E)-1-{[(4-bromophenyl)methyl]sulfinyl}-2-(4-chlorophenyl)ethene.

17. A compound according to claim 9, wherein:
   each $R^a$ is independently selected from the group consisting of halogen, $(C_1$-$C_6)$alkyl, $(C_1$-$C_6)$alkoxy, —$NO_2$, —CN and —$CF_3$, and each $R^b$ is independently selected from the group consisting of $(C_1$-$C_6)$alkoxy, halogen and nitro, and is bonded to the ortho or para position of the ring to which it is attached;
   x is 0, 1, 2 or 3; and
   y is 1, 2 or 3.

18. A compound according to claim 17, wherein the configuration of the substituents on the carbon-carbon double bond is Z—.

19. A compound according to claim 18 selected from the group consisting of: (1Z)-2-(4-chlorophenyl)-1-[benzylsulfinyl]ethene; (1Z)-2-(4-chlorophenyl)-1-{[(4-chlorophenyl)methyl]sulfinyl}-ethene; (1Z)-2-(4-chlorophenyl)-1-{[(2-chlorophenyl)methyl]sulfinyl}-ethene; (1Z)-2-(4-chlorophenyl)-1-{[(4-fluorophenyl)methyl]sulfinyl}ethene; (1Z)-2-(4-fluorophenyl)-1-[benzylsulfinyl]ethene; (1Z)-2-(4-fluorophenyl)-1-{[(4-chlorophenyl)methyl]sulfinyl}ethene; (1Z)-2-(4-fluoro-phenyl)-1-{[(2-chlorophenyl)methyl]sulfinyl}ethene; (1Z)-2-(4-fluorophenyl)-1-{[(4-fluorophenyl)methyl]sulfinyl}ethene; (1Z)-2-(4-bromophenyl)-1-[benzylsulfinyl]ethene; (1Z)-2-(4-bromophenyl)-1-{[(4-chlorophenyl)methyl]sulfinyl}ethene; (1Z)-2-(4-bromophenyl)-1-{[(2-chlorophenyl)methyl]sulfinyl}ethene; (1Z)-2-(4-bromophenyl)-1-{[(4-fluorophenyl)methyl]sulfinyl}ethene; and (1Z)-2-(4-fluorophenyl)-1-{[(4-iodophenyl)methyl]sulfinyl}ethene.

20. A compound according to claim 4, of Formula ID:

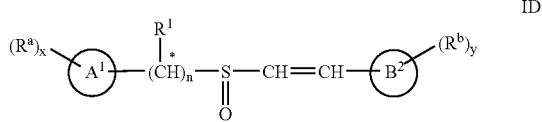

wherein B² is selected from the group consisting of heteroaryl and aryl other than phenyl or a salt thereof.

21. A compound according to claim 20, or a salt thereof, wherein B² is heteroaryl.

22. A compound according to claim 20, or a salt thereof, wherein B² is selected from the group consisting of furyl, thienyl, pyrrolyl, thiazolyl, pyridyl, thienyl-1,1-dioxide, anthryl, and naphthyl.

23. A compound according to claim 22, or a salt thereof, wherein the configuration of the substituents on the carbon-carbon double bond is E-.

24. A compound according to claim 23, or a salt thereof, wherein $R^a$ is independently selected from the group consisting of halogen, ($C_1$-$C_3$)alkoxy, —CN, —$NO_2$, and —$CF_3$.

25. A compound of claim 24 selected from the group consisting of: (1E)-1-{[(4-fluorophenyl)methyl]sulfinyl}-2-(2-pyridyl)ethene; (1E)-1-{[(4-fluorophenyl)methyl]-sulfinyl}-2-(3-pyridyl)ethene; (1E)-1-{[(4-fluorophenyl)methyl]sulfinyl}-2-(4-pyridyl)ethene; (1E)-1-{[(4-chlorophenyl)methyl]sulfinyl}-2-(2-pyridyl)ethene; (1E)-1-{[(4-chlorophenyl)methyl]sulfinyl}-2-(3-pyridyl)ethene; (1E)-1-{[(4-chlorophenyl)methyl]sulfinyl}-2-(4-pyridyl)ethene; (1E)-1-{[(4-bromophenyl)methyl]sulfinyl}-2-(2-pyridyl)ethene; (1E)-1-{[(4-bromophenyl)methyl]-sulfinyl}-2-(3-pyridyl)ethene; (1E)-1-{[(4-bromophenyl)methyl]sulfinyl}-2-(4-pyridyl)ethene; (1E)-1-{[(4-fluorophenyl)methyl]sulfinyl}-2-(2-thienyl)ethene; (1E)-1-{[(4-chlorophenyl)methyl]sulfinyl}-2-(2-thienyl)ethene; (1E)-1-{[(4-bromophenyl)methyl]sulfinyl}-2-(2-thienyl)ethene; (1E)-2-(4-bromo(2-thienyl))-1-{[(4-fluorophenyl)methyl]-sulfinyl}ethene; (1E)-2-(5-bromo(2-thienyl))-1-{[(4-fluorophenyl)methyl]-sulfinyl}ethene; (1E)-2-(5-bromo(2-thienyl))-1-{[(4-chlorophenyl)methyl]-sulfinyl}ethene; (1E)-2-(5-bromo(2-thienyl))-1-{[(4-bromophenyl)methyl]-sulfinyl}ethene; 2-((1E)-2-{[(4-fluorophenyl)methyl]sulfinyl}vinyl)thiole-1,1-dione; 2-((1E)-2-{[(4-chlorophenyl)-methyl]sulfinyl}vinyl)thiole-1,1-dione; 2-((1E)-2-{[(4-bromophenyl)methyl]-sulfinyl}vinyl)thiole-1,1-dione; (1E)-1-{[(4-fluorophenyl)methyl]sulfinyl}-2-(3-thienyl)ethene; (1E)-1-{[(4-chlorophenyl)methyl]sulfinyl}-2-(3-thienyl)ethene; (1E)-1-{[(4-bromophenyl)methyl]sulfinyl}-2-(3-thienyl)ethene; (1E)-1-{[(4-iodophenyl)methyl]sulfinyl}-2-(3-thienyl)ethene; (1E)-1-{[(4-methylphenyl)methyl]sulfinyl}-2-(3-thienyl)ethene; (1E)-1-{[(4-methoxyphenyl)-methyl]sulfinyl}-2-(3-thienyl)ethene; (1E)-1-{[(4-trifluoromethylphenyl)methyl]-sulfinyl}-2-(3-thienyl)-ethene; (1E)-1-{[(2,4-dichlorophenyl)methyl]sulfinyl}-2-(3-thienyl)-ethene; (1E)-1-{[(3,4-dichlorophenyl)methyl]sulfinyl}-2-(3-thienyl)-ethene; (1E)-1-{[(4-cyanophenyl)methyl]sulfinyl}-2-(3-thienyl)ethene; (1E)-1-{[(4-nitrophenyl)methyl]sulfinyl}-2-(3-thienyl)ethene; 3-((1E)-2-{[(4-fluorophenyl)methyl]sulfinyl}vinyl)thiole-1,1-dione; 3-((1E)-2-{[(4-chlorophenyl)methyl]sulfinyl}vinyl)thiole-1,1-dione; 3-((1E)-2-{[(4-bromophenyl)methyl]sulfinyl}vinyl)thiole-1,1-dione; 3-((1E)-2-{[(4-methoxyphenyl)-methyl]sulfinyl}vinyl)thiole-1,1-dione; 3-((1E)-2-{[(2,4-dichlorophenyl)methyl]-sulfinyl}vinyl)thiole-1,1-dione; (1E)-1-{[(4-fluorophenyl)methyl]sulfinyl}-2-(2-furyl)ethene; (1E)-1-{[(4-chlorophenyl)methyl]sulfinyl}-2-(2-furyl)ethene; (1E)-1-{[(4-bromophenyl)methyl]sulfinyl}-2-(2-furyl)ethene; (1E)-1-{[(4-fluorophenyl)methyl]sulfinyl}-2-(3-furyl)ethene; (1E)-1-{[(4-chlorophenyl)-methyl]sulfinyl}-2-(3-furyl)ethene; (1E)-1-{[(4-bromophenyl)methyl]sulfinyl}-2-(3-furyl)ethene; (1E)-1-{[(4-iodophenyl)methyl]sulfinyl}-2-(3-furyl)ethene; (1E)-1-{[(4-methylphenyl)methyl]sulfinyl}-2-(3-furyl)ethene; (1E)-1-{[(4-methoxyphenyl)methyl]sulfinyl}-2-(3-furyl)ethene; (1E)-1-{[(4-trifluoromethylphenyl)methyl]sulfinyl}-2-(3-furyl)-ethene; (1E)-1-{[(2,4-dichlorophenyl)methyl]sulfinyl}-2-(3-furyl)ethene; (1E)-1-{[(3,4-dichlorophenyl)-methyl]sulfinyl}-2-(3-furyl)ethene; (1E)-1-{[(4-cyanophenyl)methyl]sulfinyl}-2-(3-furyl)ethene; (1E)-1-{[(4-nitrophenyl)methyl]sulfinyl}-2-(3-furyl)ethene; (1E)-1-{[(4-chlorophenyl)methyl]sulfinyl}-2-(1,3-thiazol-2-yl)-ethene; (1E)-1-{[(4-chlorophenyl)methyl]sulfinyl}-2-pyrrol-2-ylethene; (1E)-1-{[(4-bromophenyl)methyl]sulfinyl}-2-pyrrol-2-ylethene; (1E)-1-{[(4-chlorophenyl)-methyl]sulfinyl}-2-(5-nitro(3-thienyl))ethene; (1E)-1-{[(4-iodophenyl)methyl]sulfinyl}-2-(5-nitro(3-thienyl))ethene; (1E)-1-{[(2,4-dichlorophenyl)methyl]sulfinyl}-2-(5-nitro (3-thienyl))ethene; (1E)-1-{[(4-methoxyphenyl)methyl]sulfinyl}-2-(5-nitro(3-thienyl))ethene; (1E)-1-{[(4-fluorophenyl)methyl]sulfinyl}-2-naphthylethene; (1E)-1-{[(4-fluorophenyl)methyl]sulfinyl}-2-(2-naphthyl)ethene; (1E)-1-{[(4-chlorophenyl)methyl]sulfinyl}-2-naphthylethene; (1E)-1-{[(4-chlorophenyl)methyl]sulfinyl}-2-(2-naphthyl) ethene; (1E)-1-{[(4-bromophenyl)methyl]sulfinyl}-2-naphthylethene; (1E)-1-{[(4-bromophenyl)methyl]-sulfinyl}-2-(2-naphthyl)ethene; (1E)-2-(9-anthryl)-1-{[(4-fluorophenyl)-methyl]sulfinyl}ethene; (1E)-2-(9-anthryl)-1-{[(4-chlorophenyl)methyl]sulfinyl}ethene; (1E)-2-(9-anthryl)-1-{[(4-bromophenyl)methyl]sulfinyl}ethene; and salts thereof.

26. A pharmaceutical composition comprising a pharmaceutically acceptable carrier and a compound according to claim 1 or a pharmaceutically acceptable salt thereof.

27. A conjugate of the Formula, IC-L-Ab;

wherein:
IC is a compound according to claim 9 or a pharmaceutically acceptable salt thereof;
Ab is an antibody; and
-L- is a single covalent bond or a linking group covalently linking said compound to said antibody.

28. A conjugate according to claim 27 wherein said antibody Ab is a monoclonal antibody or a monospecific polyclonal antibody.

29. A conjugate according to claim 28 wherein said antibody Ab is a tumor-specific antibody.

30. A pharmaceutical composition comprising a pharmaceutically acceptable carrier and at least one conjugate according to claim 27.

31. A method of treating an individual for breast cancer, prostate cancer, lung cancer or colorectal cancer comprising administering to said individual in need of such treatment an effective amount of a compound according to claim 9, or a pharmaceutically acceptable salt thereof.

32. A method of treating an individual for a cancer selected from the group consisting of breast, prostate, lung, and colorectal cancers, comprising administering to said individual an effective amount of a compound according to claim 9, or a pharmaceutically acceptable salt thereof, and administering an effective amount of therapeutic ionizing radiation to the individual.

33. A method of inducing apoptosis of tumor cells in an individual afflicted with breast cancer, prostate cancer, lung cancer or colorectal cancer comprising administering to said individual an effective amount of a compound according to claim 9, or a pharmaceutically acceptable salt thereof.

34. A method of treating an individual afflicted with breast cancer, prostate cancer, lung cancer or colorectal cancer, comprising administering to said individual an effective amount of at least one conjugate according to claim 27.

35. A process for preparing a compound according to claim 3 comprising:

(a) reacting a compound of Formula II':

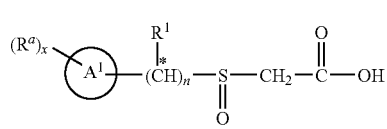

wherein $A^1$, n, $R^1$, $R^a$ and x are defined as in claim 1 with a compound of Formula III':

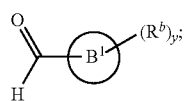

wherein $B^1$, $R^b$ and y are defined as in claim 1; and (b) isolating a compound of claim 3 from the reaction products.

36. A process according to claim 35 wherein the compound of Formula II' is prepared by:

(a) reacting a compound of Formula IIA':

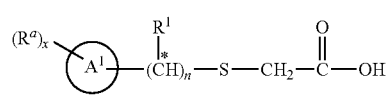

with an oxidizing agent capable of oxidizing a sulfide to a sulfoxide; and (b) isolating a compound of Formula II' from the reaction products.

37. A process according to claim 36 wherein the compound of Formula IIA' is prepared by:

(a) reacting a compound of Formula IIB':

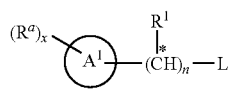

wherein:

L is a leaving group;

with mercaptoacetic acid; and (b) isolating a compound of Formula IIA' from the reaction products.

38. A process for preparing a compound according to claim 2 comprising:

(a) reacting a compound of Formula IV':

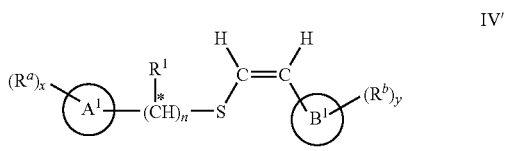

wherein $A^1$, $B^1$, n, $R^1$, $R^a$, $R^b$, x and y are defined as in claim 1;

with an oxidizing agent capable of oxidizing a sulfide to a sulfoxide; and (b) isolating a compound of claim 2 from the reaction products.

39. A process according to claim 38 wherein the compound of Formula IV' is prepared by:

(a) reacting a compound of Formula IVA':

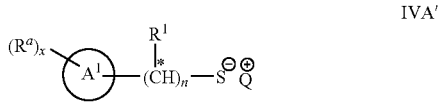

wherein $Q^+$ is a counterion selected from the group consisting of alkali metals, alkaline earth metals and transition metals;

with a compound of Formula IVB':

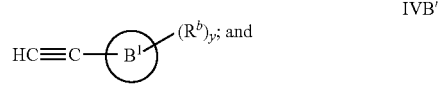

(b) isolating a compound of Formula IV' from the reaction products.

40. An isolated optical isomer of a compound according to claim 1, or a salt thereof.

* * * * *